US009278985B2

(12) United States Patent
Eckelbarger et al.

(10) Patent No.: US 9,278,985 B2
(45) Date of Patent: **\*Mar. 8, 2016**

(54) 4-AMINO-6-(HETEROCYCLIC)PICOLINATES AND 6-AMINO-2-(HETEROCYCLIC) PYRIMIDINE-4-CARBOXYLATES AND THEIR USE AS HERBICIDES

(71) Applicant: Dow AgroSciences, LLC, Indianapolis, IN (US)

(72) Inventors: Joseph D. Eckelbarger, Carmel, IN (US); Jeffrey B. Epp, Noblesville, IN (US); Stephen Craig Fields, Indianapolis, IN (US); Lindsey G. Fischer, Indianapolis, IN (US); Natalie C. Giampietro, Carmel, IN (US); Katherine A. Guenthenspberger, Daleville, IN (US); Christian T. Lowe, Westfield, IN (US); Jeff Petkus, Indianapolis, IN (US); Joshua Roth, Carmel, IN (US); Norbet M. Satchivi, Carmel, IN (US); Paul R. Schmitzer, Indianapolis, IN (US); Thomas L. Siddall, Zionsville, IN (US); Nick X. Wang, Westfield, IN (US)

(73) Assignee: Dow AgroSciences LLC, Indianapolis, IN (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/540,547

(22) Filed: Nov. 13, 2014

(65) Prior Publication Data

US 2015/0126366 A1     May 7, 2015

Related U.S. Application Data

(63) Continuation of application No. 13/839,000, filed on Mar. 15, 2013.

(51) Int. Cl.

| | |
|---|---|
| *A01N 43/40* | (2006.01) |
| *A01N 43/80* | (2006.01) |
| *A01N 43/56* | (2006.01) |
| *A01N 43/76* | (2006.01) |
| *A01N 43/78* | (2006.01) |
| *A01N 43/54* | (2006.01) |
| *C07F 7/08* | (2006.01) |
| *A01N 43/52* | (2006.01) |
| *A01N 43/647* | (2006.01) |
| *C07D 401/04* | (2006.01) |
| *C07D 403/04* | (2006.01) |
| *C07D 405/04* | (2006.01) |
| *C07D 409/04* | (2006.01) |
| *C07D 413/04* | (2006.01) |
| *C07D 417/04* | (2006.01) |
| *A01N 55/00* | (2006.01) |

(52) U.S. Cl.
CPC .............. *C07F 7/0803* (2013.01); *A01N 43/40* (2013.01); *A01N 43/52* (2013.01); *A01N 43/54* (2013.01); *A01N 43/56* (2013.01); *A01N 43/647* (2013.01); *A01N 43/76* (2013.01); *A01N 43/78* (2013.01); *A01N 43/80* (2013.01); *A01N 55/00* (2013.01); *C07D 401/04* (2013.01); *C07D 403/04* (2013.01); *C07D 405/04* (2013.01); *C07D 409/04* (2013.01); *C07D 413/04* (2013.01); *C07D 417/04* (2013.01)

(58) Field of Classification Search
None
See application file for complete search history.

(56) References Cited

U.S. PATENT DOCUMENTS

| | | | |
|---|---|---|---|
| 6,297,197 B1 | 10/2001 | Fields et al. | |
| 6,784,137 B2 | 8/2004 | Balko et al. | |
| 7,300,907 B2 | 11/2007 | Epp et al. | |
| 7,314,849 B2 | 1/2008 | Balko et al. | |
| 7,498,468 B2 | 3/2009 | Balko et al. | |
| 7,538,214 B2 | 5/2009 | Epp et al. | |
| 7,642,220 B2 | 1/2010 | Epp et al. | |
| 7,888,287 B2 | 2/2011 | Epp et al. | |
| 8,288,318 B2 | 10/2012 | Epp et al. | |
| 8,426,591 B2 | 4/2013 | Guenthenspberger et al. | |
| 8,536,331 B2 | 9/2013 | Eckelbarger et al. | |
| 8,609,592 B2 | 12/2013 | Guenthenspberger et al. | |
| 8,754,229 B2 | 6/2014 | Epp et al. | |
| 2003/0114311 A1 | 6/2003 | Balko et al. | |
| 2008/0045734 A1 | 2/2008 | Balko et al. | |
| 2008/0234262 A1 | 9/2008 | Zask et al. | |
| 2009/0088322 A1 | 4/2009 | Epp et al. | |
| 2009/0264429 A1 | 10/2009 | Apodaca et al. | |

(Continued)

FOREIGN PATENT DOCUMENTS

| | | |
|---|---|---|
| CA | 2842830 | 1/2013 |
| WO | 03/011853 | 2/2003 |

(Continued)

OTHER PUBLICATIONS

International Search Report and Written Opinion, dated Jul. 7, 2014, in International Application No. PCT/US2014/024745, (9 pages).

(Continued)

*Primary Examiner* — Mina Haghighatian
*Assistant Examiner* — Erin Hirt
(74) *Attorney, Agent, or Firm* — Michael J. Terapane; Meunier Carlin & Curfman, LLC

(57) ABSTRACT

4-Amino-6-(heterocyclic)picolinic acids and their derivatives; 6-amino-2-(heterocyclic)pyrimidine-4-carboxylates and their derivatives; and methods of using the same as herbicides.

19 Claims, No Drawings

(56) References Cited

U.S. PATENT DOCUMENTS

| | | |
|---|---|---|
| 2010/0137137 A1 | 6/2010 | Rosinger et al. |
| 2010/0179127 A1 | 7/2010 | Floersheim et al. |
| 2011/0136666 A1 | 6/2011 | Whittingham et al. |
| 2011/0281873 A1 | 11/2011 | Chiang et al. |
| 2012/0115724 A1 | 5/2012 | Whittingham et al. |
| 2012/0190549 A1 | 7/2012 | Eckelbarger et al. |
| 2012/0288492 A1 | 11/2012 | Kuo et al. |
| 2012/0292905 A1 | 11/2012 | Slot |
| 2013/0345240 A1 | 12/2013 | Whitten et al. |
| 2014/0274695 A1* | 9/2014 | Eckelbarger et al. ......... 504/103 |
| 2014/0274701 A1 | 9/2014 | Eckelbarger et al. |
| 2015/0005165 A1 | 1/2015 | Hoffman et al. |

FOREIGN PATENT DOCUMENTS

| | | |
|---|---|---|
| WO | 2005/063721 | 7/2005 |
| WO | 2006121648 | 11/2006 |
| WO | 2007/080382 A1 | 7/2007 |
| WO | 2007/082076 | 7/2007 |
| WO | 2007/082098 | 7/2007 |
| WO | 2009/007751 A2 | 1/2009 |
| WO | 2009/023438 | 2/2009 |
| WO | 2009/029735 | 3/2009 |
| WO | 2009/081112 | 7/2009 |
| WO | 2009/138712 | 11/2009 |
| WO | 2010/060581 A2 | 6/2010 |
| WO | 2010092339 | 8/2010 |
| WO | 2010/125332 A1 | 11/2010 |
| WO | 2011080568 | 7/2011 |
| WO | 2012080187 | 6/2012 |
| WO | 2012149528 | 11/2012 |
| WO | 2013/014165 | 1/2013 |
| WO | 2013003740 | 1/2013 |

OTHER PUBLICATIONS

International Search Report and Written Opinion, dated Jul. 10, 2014, in International Application No. PCT/US2014/024749, (9 pages).
International Search Report and Written Opinion, dated Jul. 7, 2014, in International Application No. PCT/US2014/024752, (9 pages).
Abell, et al. "Target-Site Directed Herbicide Design in, pest control with enhanced environmental safety 15-37", 1993.
Knight, et al. "Annual Review of Phytopathology", 1997.
Ruegg, et al. "Weed Research", 2006.
International Search Report and Written Opinion of the EP International Searching Authority from International Application No. PCT/EP2012/064519 mailed Sep. 28, 2012.

* cited by examiner

4-AMINO-6-(HETEROCYCLIC)PICOLINATES AND 6-AMINO-2-(HETEROCYCLIC) PYRIMIDINE-4-CARBOXYLATES AND THEIR USE AS HERBICIDES

CROSS-REFERENCE TO RELATED APPLICATIONS

This application is a continuation of application Ser. No. 13/839,000, filed Mar. 15, 2013.

FIELD

The invention relates to herbicidal compounds and compositions and to methods for controlling undesirable vegetation.

BACKGROUND

The occurrence of undesirable vegetation, e.g., weeds, is a constant problem facing farmers in crops, pasture, and other settings. Weeds compete with crops and negatively impact crop yield. The use of chemical herbicides is an important tool in controlling undesirable vegetation.

There remains a need for new chemical herbicides that offer a broader spectrum of weed control, selectivity, minimal crop damage, storage stability, ease of handling, higher activity against weeds, and/or a means to address herbicide-tolerance that develops with respect to herbicides currently in use.

SUMMARY OF THE INVENTION

Provided herein are compounds of Formula (I):

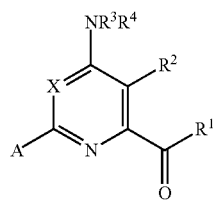

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1'''}$ and $R^{1''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is one of groups A1 to A36

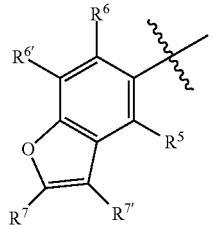

A1

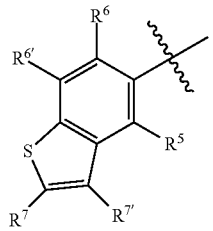

A2

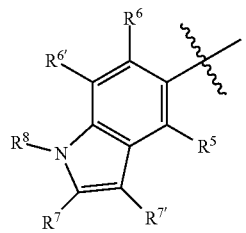

A3

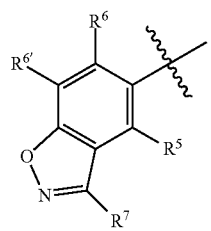

A4

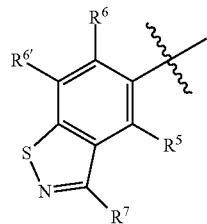

A5

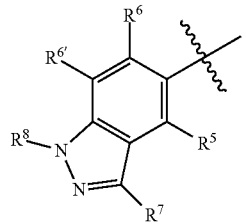

A6

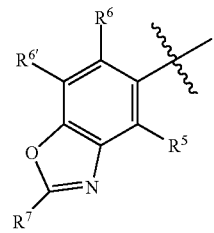
A7
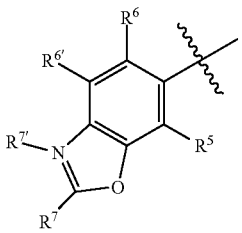
A13
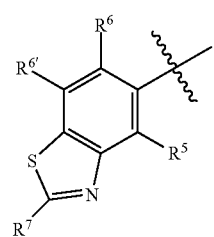
A8
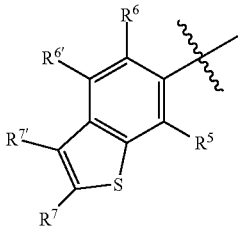
A14
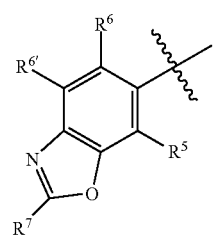
A9
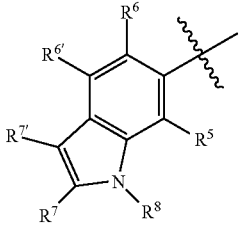
A15
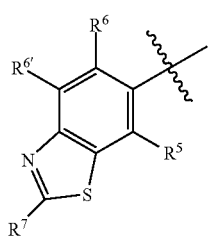
A10
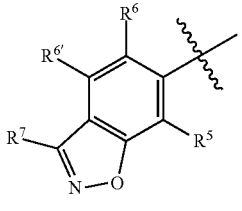
A16
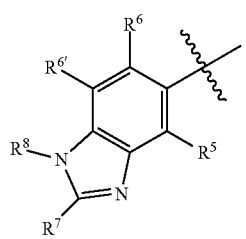
A11
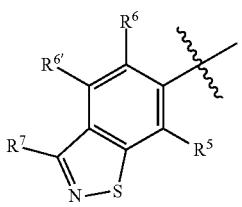
A17
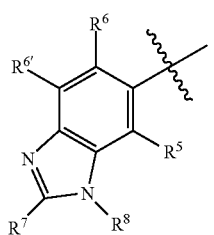
A12
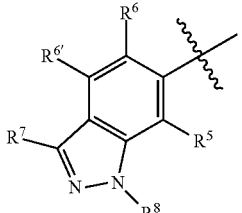
A18
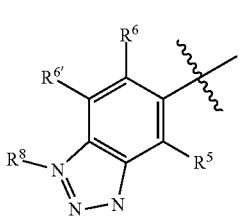
A19

-continued
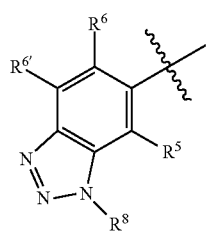 A20
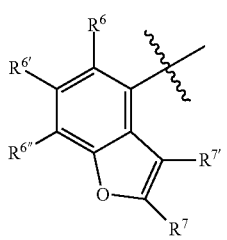 A21
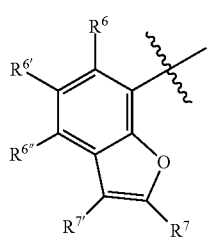 A22
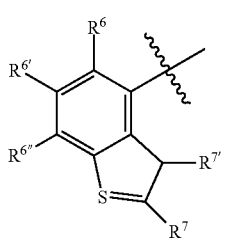 A23
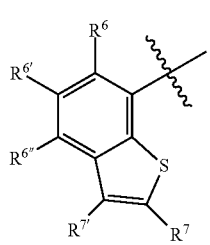 A24
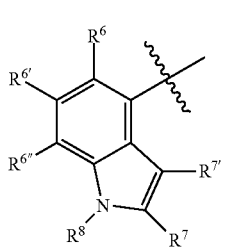 A25
-continued
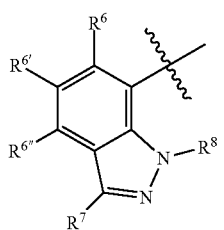 A26
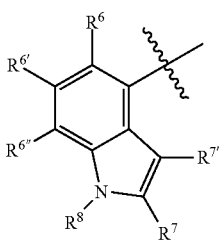 A27
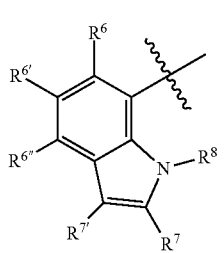 A28
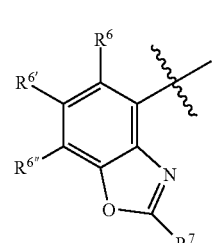 A29
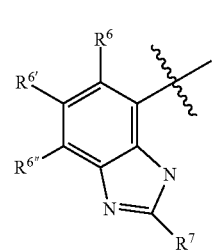 A30
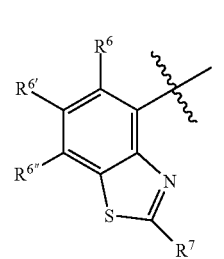 A31

A32 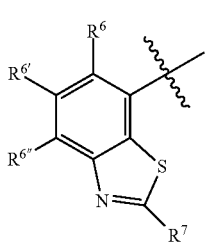

A33 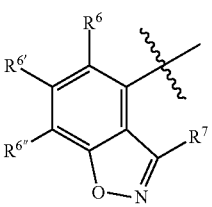

A34 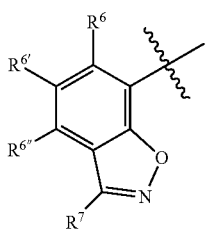

A35 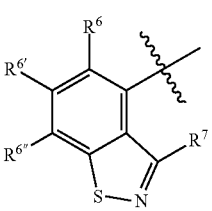

A36 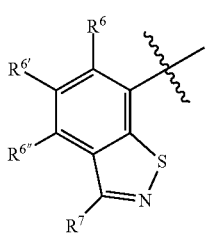

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alknyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an N-oxide or agriculturally acceptable salt thereof.

Also provided are methods of controlling undesirable vegetation comprising (a) contacting the undesirable vegetation or area adjacent to the undesirable vegetation or (b) pre-emergently contacting soil or water a herbicidally effective amount of at least one compound of Formula (I) or agriculturally acceptable derivative thereof.

Also provided are novel precursors of Formula (II):

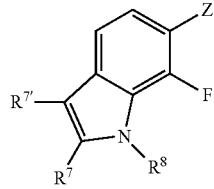

wherein:

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alknyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

Z is $B(OR^{22})_2$, $BF_3M$, or $Sn(R^{23})_3$, wherein each $R^{22}$ is independently hydrogen or $C_1$-$C_4$ alkyl, or the two $OR^{22}$ moieties combine to form —O—C(CH$_3$)$_2$—C(CH$_3$)$_2$—O— or —O—CH$_2$—C(CH$_3$)$_2$—CH$_2$—O—; M is a metal cation, e.g. sodium or potassium, and $R^{23}$ is $C_1$-$C_4$ alkyl; provided the following compound is excluded:

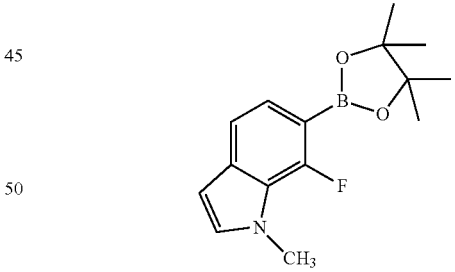

DETAILED DESCRIPTION

Definitions

As used herein, herbicide and herbicidal active ingredient mean a compound that controls undesirable vegetation when applied in an appropriate amount.

As used herein, control of or controlling undesirable vegetation means killing or preventing the vegetation, or causing some other adverse modifying effect to the vegetation e.g., deviations from natural growth or development, regulation, desiccation, retardation, and the like.

As used herein, a herbicidally effective or vegetation controlling amount is an amount of herbicidal active ingredient the application of which controls the relevant undesirable vegetation.

As used herein, applying an herbicide or herbicidal composition means delivering it directly to the targeted vegetation or to the locus thereof or to the area where control of undesired vegetation is desired. Methods of application include, but are not limited to, pre-emergently contacting soil or water, post-emergently contacting the undesirable vegetation or area adjacent to the undesirable vegetation.

As used herein, plants and vegetation include, but are not limited to, dormant seeds, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Suitable salts include those derived from alkali or alkaline earth metals and those derived from ammonia and amines. Preferred cations include sodium, potassium, magnesium, and aminium cations of the formula:

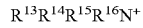

wherein $R^{13}$, $R^{14}$, $R^{15}$ and $R^{16}$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^{13}$, $R^{14}$, $R^{15}$ and $R^{16}$ are sterically compatible. Additionally, any two $R^{13}$, $R^{14}$, $R^{15}$ and $R^{16}$ together may represent an aliphatic difunctional moiety containing one to twelve carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide. Amine salts are often preferred forms of the compounds of Formula I because they are water-soluble and lend themselves to the preparation of desirable aqueous based herbicidal compositions.

Compounds of the formula (I) include N-oxides. Pyridine N-oxides can be obtained by oxidation of the corresponding pyridines. Suitable oxidation methods are described, for example, in Houben-Weyl, Methoden der organischen Chemie [Methods in organic chemistry], expanded and subsequent volumes to the 4th edition, volume E 7b, p. 565 f.

As used herein, unless otherwise specified, acyl refers to formyl, $C_1$-$C_3$ alkylcarbonyl, and $C_1$-$C_3$ haloalkylcarbonyl. $C_1$-$C_6$ acyl refers to formyl, $C_1$-$C_5$ alkylcarbonyl, and $C_1$-$C_5$ haloalkylcarbonyl (the group contains a total of 1 to 6 carbon atoms).

As used herein, alkyl refers to saturated, straight-chained or branched saturated hydrocarbon moieties. Unless otherwise specified, $C_1$-$C_{10}$ alkyl groups are intended. Examples include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl.

As used herein, "haloalkyl" refers to straight-chained or branched alkyl groups, where in these groups the hydrogen atoms may partially or entirely be substituted with halogen atoms. Unless otherwise specified, $C_1$-$C_8$ groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl.

As used herein, alkenyl refers to unsaturated, straight-chained, or branched hydrocarbon moieties containing a double bond. Unless otherwise specified, $C_2$-$C_8$ alkynyl are intended. Alkynyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. Vinyl refers to a group having the structure —CH═CH$_2$, 1-propenyl refers to a group with the structure —CH═CH—CH$_3$; and 2-propenyl refers to a group with the structure —CH$_2$—CH═CH$_2$.

As used herein, alkynyl represents straight-chained or branched hydrocarbon moieties containing a triple bond. Unless otherwise specified, $C_2$-$C_8$ alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butinyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3- dimethyl-1-butynyl, 1-ethyl-2-butynyl, 1-ethyl-3-butynyl, 2-ethyl-3-butynyl, and 1-ethyl-1-methyl-2-propynyl.

As used herein, alkoxy refers to a group of the formula R—O—, where R is alkyl as defined above. Unless otherwise specified, alkoxy groups wherein R is a $C_1$-$C_8$ alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, haloalkoxy refers to a group of the formula R—O—, where R is haloalkyl as defined above. Unless otherwise specified, haloalkoxy groups wherein R is a $C_1$-$C_8$ alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro, 2-difluoroethoxy, 2,2-dichloro-2-fluoroethoxy, 2,2,2-trichloroethoxy, pentafluoroethoxy, and 1,1,1-trifluoroprop-2-oxy.

As used herein, alkylthio refers to a group of the formula R—S— where R is alkyl as defined above. Unless otherwise specified, alkylthio groups wherein R is a $C_1$-$C_8$ alkyl group are intended. Examples include methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dio-methylpropylthio, 1-ethylpropylthio, hexylthio, 1,1-dimethyl propylthio, 1,2-dimethyl propylthio, 1-methylpentylthio, 2-methylpentylthio, 3-methyl-pentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethyl-butylthio, 1,1,2-trimethyl propylthio, 1,2,2-trimethyl propylthio, 1-ethyl-1-methyl propylthio, and 1-ethyl-2-methylpropylthio.

As used herein, haloalkylthio refers to an alkylthio group as defined above wherein the carbon atoms are partially or entirely substituted with halogen atoms. Unless otherwise specified, haloalkylthio groups wherein R is a $C_1$-$C_8$ alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, aryl, as well as derivative terms such as aryloxy, refers to a phenyl, indanyl or naphthyl group with phenyl being preferred. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein alkylcarbonyl refers to an alkyl group bonded to a carbonyl group. $C_1$-$C_3$ alkylcarbonyl and $C_1$-$C_3$ haloalkylcarbonyl refer to groups wherein a $C_1$-$C_3$ alkyl group is bonded to a carbonyl group (the group contains a total of 2 to 4 carbon atoms).

As used herein, alkoxycarbonyl refers to a group of the formula

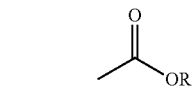

wherein R is alkyl.

As used herein, arylalkyl refers to an alkyl group substituted with an aryl group. $C_7$-$C_{10}$ arylalkyl refers to a group wherein the total number of carbon atoms in the group is 7 to 10.

As used herein alkylamino refers to an amino group substituted with one or two alkyl groups, which may be the same or different.

As used herein haloalkylamino refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ alkyl, and $C_1$-$C_6$ dialkylaminocarbonyl refers to a group of the formula $R_2NC(O)$— wherein each R is independently $C_1$-$C_6$ alkyl.

As used herein alkylcarbamyl refers to a carbamyl group substituted on the nitrogen with an alkyl group.

As used herein alkylsulfonyl refers to a group of the formula

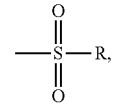

where R is alkyl

As used herein carbamyl (also referred to as carbamoyl and aminocarbonyl) refers to a group of the formula

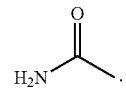

As used herein dialkylphosponyl refers to a group of the formula

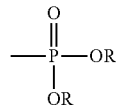

where R is independently alkyl in each occurrence.

As used herein, $C_1$-$C_6$ trialkylsilyl refers to a group of the formula —$SiR_3$ wherein each R is independently a $C_1$-$C_6$ alkyl group (the group contains a total of 3 to 18 carbon atoms).

As used herein Me refers to a methyl group; OMe refers to a methoxy group; i-Pr refers to an isopropyl group.

As used herein, the term "halogen" including derivative terms such as "halo" refers to fluorine, chlorine, bromine and iodine.

As used herein, plants and vegetation include, but are not limited to, germinant seeds, emerging seedlings, plants emerging from vegetative propagules, immature vegetation, and established vegetation.

Compounds of Formula (I)

The invention provides compounds of Formula (I) as defined above and N-oxides and agriculturally acceptable salts thereof.

In some embodiments, the compound is the carboxylic acid or an agriculturally acceptable ester or salt. In some embodiments, the compound is the carboxylic acid or its methyl ester.

In some embodiments:

A is one of groups A1 to A20;
$R^1$ is $OR^{1'}$, wherein $R^{1'}$ is hydrogen or $C_1$-$C_4$ alkyl;
$R^2$ is chlorine;
$R^3$ and $R^4$ are hydrogen;
X is N, CH, CF, CCl, or CBr;
$R^5$ is hydrogen, halogen, OH, NH2, CN, $C_1$-$C_3$ alkyl, $C_1$-$C_3$ alkoxy, $C_1$-$C_3$ alkylamino, or cyclopropyl;
$R^6$, $R^{6'}$, and $R^{6''}$ are independently hydrogen, halogen, OH, $NH_2$, CN, $C_1$-$C_3$ alkyl, $C_1$-$C_3$ alkoxy, cyclopropyl, or vinyl;
$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, or $C_1$-$C_3$ alkylamino, or phenyl; and
$R^8$ is hydrogen, $C_1$-$C_3$ alkyl, phenyl, or $C_1$-$C_3$ alkylcarbonyl.

In some embodiments, $R^1$ is $OR^{1'}$, wherein $R^{1'}$ is hydrogen, $C_1$-$C_8$ alkyl, or $C_7$-$C_{10}$ arylalkyl. In some embodiments, $R^{1'}$ is hydrogen or $C_1$-$C_8$ alkyl. In some embodiments, $R^{1'}$ is hydrogen.

In some embodiments, $R^2$ is halogen, $C_1$-$C_4$ alkyl, $C_1$-$C_4$ haloalkyl, $C_2$-$C_4$ alkynyl, $C_2$-$C_4$-alkenyl, $C_2$-$C_4$ haloalkenyl, or $C_1$-$C_4$-alkoxy, or $C_1$-$C_4$ haloalkoxy. In some embodiments, $R^2$ is halogen, $C_2$-$C_4$-alkenyl, $C_2$-$C_4$ haloalkenyl, or $C_1$-$C_4$-alkoxy. In some embodiments, $R^2$ is halogen. In some embodiments, $R^2$ is $C_2$-$C_4$-alkenyl or $C_2$-$C_4$ haloalkenyl. In some embodiments, $R^2$ is $C_1$-$C_4$ alkoxy. In some embodiments, $R^2$ is Cl, OMe, vinyl, or 1-propenyl. In some embodiments, $R^2$ is Cl. In some embodiments, $R^2$ is OMe. In some embodiments, $R^2$ is vinyl or 1-propenyl.

In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alknyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alknyl, $C_1$-$C_6$ alkoxy, or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, or $R^3$ and $R^4$ taken together represent •$CR^{3'}(R^{4'})$, wherein $R^{3'}$ and $R^{4'}$ are independently hydrogen, $C_1$-$C_6$ alkyl, $C_1$-$C_6$ alkoxy or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, or $C_1$-$C_3$ haloalkylcarbonyl. In some embodiments, at least one of $R^3$ and $R^4$ are hydrogen. In some embodiments, $R^3$ and $R^4$ are both hydrogen.

In some embodiments, X is N, CH or CF. In some embodiments, X is N. In some embodiments, X is CH. In some embodiments, X is CF.

In some embodiments, A is A1, A2, A3, A4, A5, A6, A7, A8, A9, A10, A11, A12, A13, A14, A15, A16, A17, A18, A19, or A20.

In some embodiments, A is one of A21, A22, A23, A24, A25, A26, A27, A28, A29, A30, A31, A32, A33, A34, A35, and A36.

In some embodiments, A is one of groups A1, A2, A3, A7, A8, A9, A10, A13, A14, and A15. In some embodiments, A is one of groups A1, A2, A3, A13, A14, and A15. In some embodiments, A is one of groups A13, A14, and A15. In some embodiments, A is A15.

In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, or amino. In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, or amino. In some embodiments, $R^5$ is hydrogen, halogen, $C_1$-$C_4$ alkyl or $C_1$-$C_4$ alkoxy. In some embodiments, $R^5$ is hydrogen or F. In some embodiments, $R^5$ is hydrogen. In some embodiments, $R^5$ is F.

In some embodiments, $R^6$ is hydrogen, halogen, $C_1$-$C_4$ alkyl, $C_1$-$C_4$ haloalkyl, $C_1$-$C_3$ alkoxy, or $C_1$-$C_3$ haloalkoxy. In some embodiments, $R^6$ is hydrogen or fluorine. In some embodiments, $R^6$ is hydrogen. In some embodiments, $R^6$ is fluorine.

In some embodiments, $R^{6'}$ is hydrogen or halogen. In some embodiments, $R^{6'}$ is hydrogen, F, or Cl. In some embodiments, $R^{6'}$ is hydrogen or F. In some embodiments, $R^{6'}$ is hydrogen.

In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In some embodiments, $R^{6''}$ is hydrogen. In some embodiments, $R^{6''}$ is halogen. In some embodiments, $R^{6''}$ is $C_1$-$C_4$ alkyl. In some embodiments, $R^{6''}$ is $C_1$-$C_4$ haloalkyl. In some embodiments, $R^{6''}$ is cyclopropyl. In some embodiments, $R^{6''}$ is $C_2$-$C_4$ alkynyl. In some embodiments, $R^{6''}$ is CN. In some embodiments, $R^{6''}$ is $NO_2$.

In some embodiments:
$R^2$ is halogen, $C_2$-$C_4$-alkenyl, $C_2$-$C_4$ haloalkenyl, or $C_1$-$C_4$-alkoxy;
$R^3$ and $R^4$ are both hydrogen; and
X is N, CH, or CF.

In some embodiments:
$R^2$ is halogen;
$R^3$ and $R^4$ are both hydrogen; and
X is N, CH, or CF.

In some embodiments:
$R^2$ is $C_2$-$C_4$-alkenyl or $C_2$-$C_4$ haloalkenyl;
$R^3$ and $R^4$ are both hydrogen; and
X is N, CH, or CF.

In some embodiments:
$R^2$ is $C_1$-$C_4$-alkoxy;
$R^3$ and $R^4$ are both hydrogen; and
X is N, CH, or CF.

In some embodiments:
$R^2$ is halogen, $C_2$-$C_4$-alkenyl, $C_2$-$C_4$ haloalkenyl, or $C_1$-$C_4$-alkoxy;
$R^3$ and $R^4$ are both hydrogen;
X is N, CH, or CF;
$R^5$ is hydrogen or F;
$R^6$ is hydrogen or F;
$R^{6'}$ is hydrogen;

R⁶", if applicable to the relevant A group, is hydrogen or halogen; and

R⁷ and R⁷', if applicable to the relevant A group, are independently hydrogen or halogen.

In some embodiments:
$R^2$ is halogen, $C_1$-$C_4$-alkoxy, or $C_2$-$C_4$-alkenyl;
$R^3$ and $R^4$ are hydrogen;
X is N, CH, or CF; and
A is one of groups A1 to A20;

In some embodiments:
$R^2$ is chlorine;
$R^3$ and $R^4$ are hydrogen;
X is N, CH, or CF;
A is one of groups A1 to A20;
$R^5$ is hydrogen or F;
$R^6$ and $R^{6'}$ are independently hydrogen or F; and
$R^7$ and $R^{7'}$, if applicable to the relevant A group, are independently hydrogen, halogen, $C_1$-$C_4$ alkyl, or $C_1$-$C_4$ haloalkyl.

In some embodiments:
$R^2$ is chlorine, methoxy, vinyl, or 1-propenyl;
$R^3$ and $R^4$ are hydrogen; and
X is N, CH, or CF.

In some embodiments:
$R^2$ is chlorine;
$R^3$ and $R^4$ are hydrogen; and
X is N, CH, or CF.

In some embodiments:
$R^2$ is vinyl or 1-propenyl;
$R^3$ and $R^4$ are hydrogen; and
X is N, CH, or CF.

In some embodiments:
$R^2$ is methoxy;
$R^3$ and $R^4$ are hydrogen; and
X is N, CH, or CF.

In some embodiments:
$R^2$ is chlorine;
$R^3$ and $R^4$ are hydrogen; and
X is N.

In some embodiments:
$R^2$ is chlorine;
$R^3$ and $R^4$ are hydrogen; and
X is CH.

In some embodiments:
$R^2$ is chlorine;
$R^3$ and $R^4$ are hydrogen; and
X is CF.

In some embodiments:
$R^2$ is chlorine;
$R^3$ and $R^4$ are hydrogen;
X is CF;
A is one of A1, A2, A3, A7, A8, A9, A10, A13, A14, or A15;
$R^5$ is F; and
$R^6$ is H.

In some embodiments:
$R^2$ is chlorine, methoxy, vinyl, or 1-propenyl;
$R^3$ and $R^4$ are hydrogen;
X is N, CH, or CF; and
A is one of A21-A36.

In some embodiments:
$R^2$ is chlorine, methoxy, vinyl, or 1-propenyl;
$R^3$ and $R^4$ are hydrogen;
X is CF; and A is one of

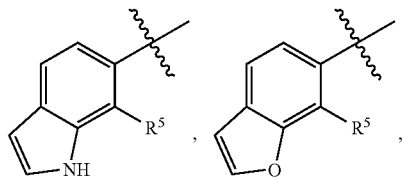

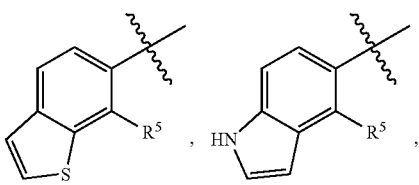

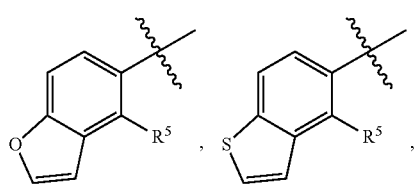

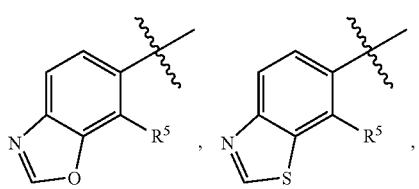

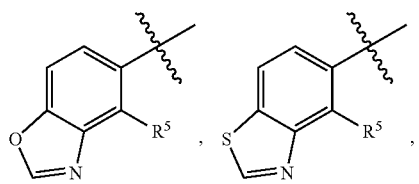

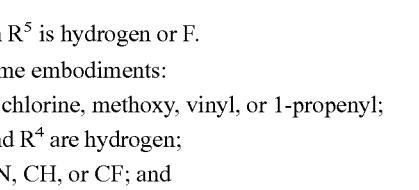

wherein $R^5$ is hydrogen or F.

In some embodiments:
$R^2$ is chlorine, methoxy, vinyl, or 1-propenyl;
$R^3$ and $R^4$ are hydrogen;
X is N, CH, or CF; and
A is

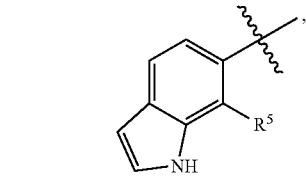

where $R^5$ is hydrogen or F.

In some embodiments:
$R^2$ is chlorine, methoxy, vinyl, or 1-propenyl;
$R^3$ and $R^4$ are hydrogen;
X is N, CH, or CF; and A is

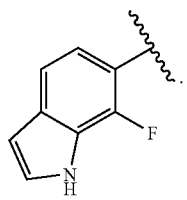 [SMILES: *c1ccc2cc[nH]c2c1F]

In some embodiments:
R² is chlorine, methoxy, vinyl, or 1-propenyl;
R³ and R⁴ are hydrogen;
X is CF; and
A is

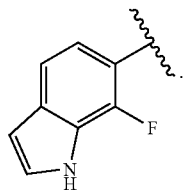 [SMILES: *c1ccc2cc[nH]c2c1F]

It is particularly noteworthy that compounds of Formula (I) wherein A is, e.g. A15, exhibit a significant increase in activity when X is CF. This is demonstrated by comparing the activity of Compounds 1.21 and 1.22 (wherein X is CH) with that of 1.08 and 1.09 (wherein X is CF). It is also demonstrated by comparing the activity of Compounds 1.23 and 1.24 (wherein X is CH) with that of Compounds 1.15 and 1.16 (wherein X is CF). The increased activity is further enhanced when R⁵ is F.

Exemplary Compounds

The following Tables 1-9 describe exemplary compounds of Formula (I')

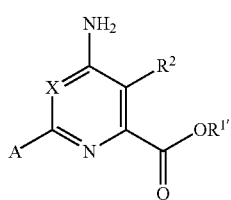

Table 10 sets forth the structure, appearance, preparation method, and precursor(s) used in synthesis of the exemplary compounds. Table 11 sets forth physical data for each of the exemplary compounds.

Blank spaces in compound tables herein indicate hydrogen, or that for the A group indicated in a particular row the column in which the blank occurs is not relevant

TABLE 1

Compounds of Formula (I') with indolyl tails

| C.No. | R¹' | R² | X | A | R⁵ | R⁶ | R⁶' | R⁶" | R⁷ | R⁷' | R⁸ |
|---|---|---|---|---|---|---|---|---|---|---|---|
| 1.01 | H | Cl | CF | A03 | | | | | | | Me |
| 1.02 | Me | Cl | CF | A03 | | | | | | | |
| 1.03 | Me | Cl | CF | A03 | | | | | | | Me |
| 1.04 | H | Cl | CF | A03 | | | | | | | |
| 1.05 | Me | Cl | CCl | A15 | | | | | | | |
| 1.06 | H | Cl | CCl | A15 | | | | | | | |
| 1.07 | Me | Cl | CCl | A15 | F | | | | | | |
| 1.08 | Me | Cl | CF | A15 | | | | | | | |
| 1.09 | H | Cl | CF | A15 | | | | | | | |
| 1.10 | Me | Cl | CF | A15 | | | | | | | Me |
| 1.11 | H | Cl | CF | A15 | | | | | | | Me |
| 1.12 | Me | Cl | CF | A15 | F | | | | | | Si(i-Pr)₃ |
| 1.13 | Me | Cl | CF | A15 | | F | | | | | |
| 1.14 | H | Cl | CF | A15 | | F | | | | | |
| 1.15 | Me | Cl | CF | A15 | F | | | | | | |
| 1.16 | H | Cl | CF | A15 | F | | | | | | |
| 1.17 | H | OMe | CF | A15 | F | | | | | | |
| 1.18 | Me | vinyl | CF | A15 | F | | | | | | |
| 1.19 | H | vinyl | CF | A15 | F | | | | | | |
| 1.20 | Me | OMe | CF | A15 | F | | | | | | |
| 1.21 | Me | Cl | CH | A15 | | | | | | | |
| 1.22 | H | Cl | CH | A15 | | | | | | | |
| 1.23 | Me | Cl | CH | A15 | F | | | | | | |
| 1.24 | H | Cl | CH | A15 | F | | | | | | |
| 1.25 | Me | Cl | CH | A15 | | F | | | | | |
| 1.26 | H | Cl | CH | A15 | | F | | | | | |
| 1.27 | Me | Cl | CH | A15 | F | F | | | | | |
| 1.28 | Me | Cl | CMe | A15 | | | | | | | |
| 1.29 | H | Cl | CMe | A15 | | | | | | | |
| 1.30 | Me | Cl | N | A15 | | | | | | | |
| 1.31 | Me | Cl | N | A15 | F | | | | | | |
| 1.32 | Me | OMe | N | A15 | | | | | | | |
| 1.33 | H | OMe | N | A15 | | | | | | | |
| 1.34 | Me | OMe | N | A15 | F | | | | | | |
| 1.35 | H | OMe | N | A15 | F | | | | | | |
| 1.36 | Me | OMe | N | A15 | | F | | | | | |
| 1.37 | H | OMe | N | A15 | | F | | | | | |
| 1.38 | Me | vinyl | N | A15 | F | | | | | | |
| 1.39 | H | vinyl | N | A15 | F | | | | | | |
| 1.40 | Me | Cl | CF | A27 | | | | | | | |
| 1.41 | Me | Cl | CF | A27 | | | | | | | Me |
| 1.42 | H | Cl | CF | A27 | | | | | | | Me |
| 1.43 | Me | Cl | CF | A27 | | | | | | Cl | |
| 1.44 | Me | Cl | CH | A27 | | | | | | Cl | |
| 1.45 | Me | OMe | N | A27 | | | | | | Cl | |
| 1.46 | Me | Cl | CF | A28 | | | | | | Cl | |
| 1.47 | Me | Cl | CF | A28 | | | | | | | |
| 1.48 | H | Cl | CF | A28 | | | | | | | |
| 1.49 | Me | Cl | CH | A28 | | | | | | Cl | |
| 1.50 | Me | OMe | N | A28 | | | | | | Cl | |

A is A3, A15, A27, or A28

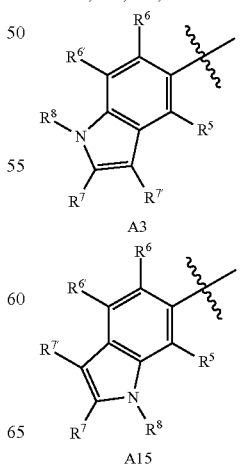

TABLE 1-continued

Compounds of Formula (I') with indolyl tails

| C.No. | R¹' | R² | X | A | R⁵ | R⁶ | R⁶' | R⁶" | R⁷ | R⁷' | R⁸ |
|---|---|---|---|---|---|---|---|---|---|---|---|

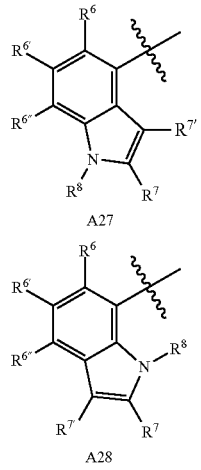

A27

A28

TABLE 2

Compounds of Formula (I') with bernzofuranyl tails

| C.No. | R¹' | R² | X | A | R⁵ | R⁶ | R⁶' | R⁶" | R⁷ | R⁷' | R⁸ |
|---|---|---|---|---|---|---|---|---|---|---|---|
| 2.01 | Me | Cl | CF | A01 | | | | | | | |
| 2.02 | H | Cl | CF | A01 | | | | | | | |
| 2.03 | Me | Cl | CH | A01 | | | | | | | |
| 2.04 | Me | Cl | CH | A01 | | F | | | | | |
| 2.05 | Me | OMe | N | A01 | | F | | | | | |
| 2.06 | Me | OMe | N | A01 | | | | | | | |
| 2.07 | Me | Cl | CF | A13 | | | | | | | |
| 2.08 | H | Cl | CF | A13 | | | | | | | |
| 2.09 | Me | Cl | CF | A13 | F | | | | | | |
| 2.10 | Me | Cl | CF | A13 | | F | | | | | |
| 2.11 | Me | Cl | CH | A13 | F | | | | | | |
| 2.12 | Me | Cl | CH | A13 | | F | | | | | |
| 2.13 | Me | OMe | N | A13 | F | | | | | | |
| 2.14 | Me | OMe | N | A13 | | F | | | | | |
| 2.15 | Me | Cl | CF | A21 | | | | | | | |
| 2.16 | Me | Cl | CF | A21 | | | | | | Cl | |
| 2.17 | H | Cl | CF | A21 | | | | | | | |
| 2.18 | H | Cl | CF | A21 | | | | | | Cl | |
| 2.19 | Me | Cl | CH | A21 | | | | | | Cl | |
| 2.20 | Me | Cl | N | A21 | | | | | | Cl | |
| 2.21 | Me | OMe | N | A21 | | | | | | Cl | |
| 2.22 | H | OMe | N | A21 | | | | | | Cl | |
| 2.23 | H | Cl | N | A21 | | | | | | Cl | |
| 2.24 | Me | Cl | CF | A22 | | | | | | Cl | |
| 2.25 | Me | Cl | CH | A22 | | | | | | Cl | |
| 2.26 | Me | OMe | N | A22 | | | | | | Cl | |

A is A1, A13, A21, or A22

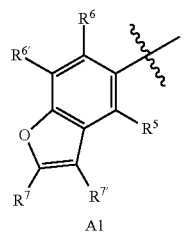

A1

TABLE 2-continued

Compounds of Formula (I') with bernzofuranyl tails

| C.No. | R¹' | R² | X | A | R⁵ | R⁶ | R⁶' | R⁶" | R⁷ | R⁷' | R⁸ |
|---|---|---|---|---|---|---|---|---|---|---|---|

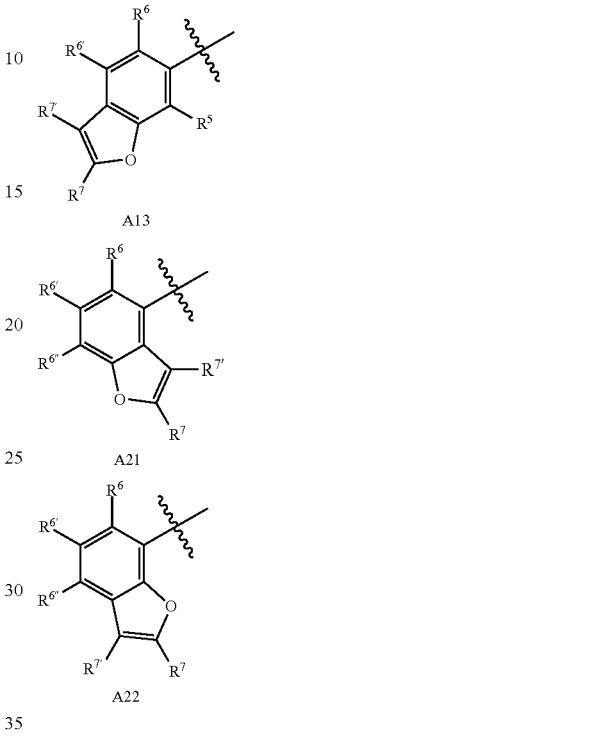

A13

A21

A22

TABLE 3

Compounds of Formula (I') with benzothiofuranyl tails

| C.No. | R¹' | R² | X | A | R⁵ | R⁶ | R⁶' | R⁶" | R⁷ | R⁷' | R⁸ |
|---|---|---|---|---|---|---|---|---|---|---|---|
| 3.01 | Me | Cl | CCl | A02 | | | | | | | |
| 3.02 | H | Cl | CCl | A02 | | | | | | | |
| 3.03 | Me | Cl | CF | A02 | | | | | | | |
| 3.04 | H | Cl | CF | A02 | | | | | | | |
| 3.05 | Me | Cl | CH | A02 | | | | | | | |
| 3.06 | Me | Cl | CMe | A02 | | | | | | | |
| 3.07 | H | Cl | CMe | A02 | | | | | | | |
| 3.08 | Me | OMe | N | A02 | | | | | | | |
| 3.09 | H | OMe | N | A02 | | | | | | | |
| 3.10 | Me | Cl | CCl | A14 | | | | | | | |
| 3.11 | H | Cl | CCl | A14 | | | | | | | |
| 3.12 | Me | Cl | CF | A14 | | | | | | | |
| 3.13 | H | Cl | CF | A14 | | | | | | | |
| 3.14 | Me | Cl | CF | A14 | | | | | | F | |
| 3.15 | Me | Cl | CH | A14 | | | | | | | |
| 3.16 | H | Cl | CH | A14 | | | | | | | |
| 3.17 | Me | Cl | CH | A14 | | | | | | F | |
| 3.18 | Me | Cl | CMe | A14 | | | | | | | |
| 3.19 | H | Cl | CMe | A14 | | | | | | | |
| 3.20 | Me | OMe | N | A14 | | | | | | | |
| 3.21 | H | OMe | N | A14 | | | | | | | |
| 3.22 | Me | OMe | N | A14 | | | | | | F | |
| 3.23 | Me | Cl | CF | A23 | | | | | | | |
| 3.24 | Me | Cl | CF | A24 | | | | | | | |
| 3.25 | H | Cl | CF | A24 | | | | | | | |
| 3.26 | Me | Cl | CF | A24 | | | | | | | Br |
| 3.27 | Me | Cl | CH | A24 | | | | | | | |

A is A2, A14, A23, or A24:

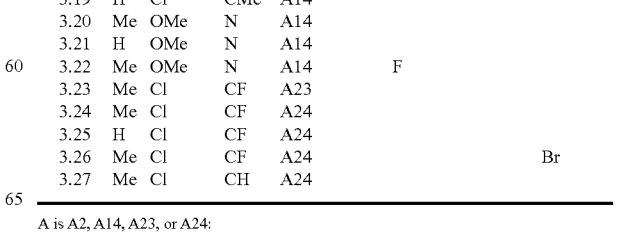

TABLE 3-continued

Compounds of Formula (I') with benzothiofuranyl tails

C.No. R¹' R² X A R⁵ R⁶ R⁶' R⁶" R⁷ R⁷' R⁸

A2

A14

A23

A24

TABLE 4

Compounds of Formula (I') with 1H-indazolyl tails

| C.No. | R¹' | R² | X | A | R⁵ | R⁶ | R⁶' | R⁶" | R⁷ | R⁷' | R⁸ |
|---|---|---|---|---|---|---|---|---|---|---|---|
| 4.01 | Me | Cl | CF | A06 | | | | | | | |
| 4.02 | H | Cl | CF | A06 | | | | | | | |
| 4.03 | Me | Cl | CF | A06 | | | | | | | Me |
| 4.04 | H | Cl | CF | A06 | | | | | | | Me |
| 4.05 | Me | Cl | CF | A18 | | | | | | | |
| 4.06 | H | Cl | CF | A18 | | | | | | | |
| 4.07 | Me | Cl | CF | A18 | | | | | | | Me |
| 4.08 | H | Cl | CF | A18 | | | | | | | Me |
| 4.09 | Me | Cl | CH | A18 | | | | | | | |
| 4.10 | Me | Cl | CF | A25 | | | | | | | Me |
| 4.11 | H | Cl | CF | A25 | | | | | | | Me |
| 4.12 | Me | Cl | CF | A25 | | | | | | | |
| 4.13 | Me | Cl | CF | A26 | | | | | | | |

A is one of groups A6, A18, A25, and A26:

TABLE 4-continued

Compounds of Formula (I') with 1H-indazolyl tails

C.No. R¹' R² X A R⁵ R⁶ R⁶' R⁶" R⁷ R⁷' R⁸

A6

A18

A25

A26

TABLE 5

Compounds of Formula (I') with benzoxazolyl tails

| C. No. | R¹' | R² | X | A | R⁵ | R⁶ | R⁶' | R⁶" | R⁷ | R⁷' | R⁸ |
|---|---|---|---|---|---|---|---|---|---|---|---|
| 5.01 | Me | Cl | CF | A09 | | | | | | | |

A is A7, A9, A29, or A30:

A7

TABLE 5-continued

Compounds of Formula (I') with benzoxazolyl tails

| C. No. | R¹' | R² | X | A | R⁵ | R⁶ | R⁶' | R⁶" | R⁷ | R⁷' | R⁸ |
|---|---|---|---|---|---|---|---|---|---|---|---|

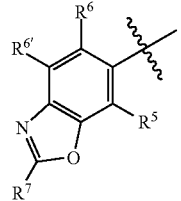

A9

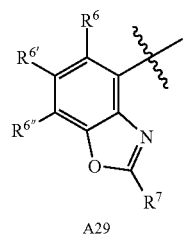

A29

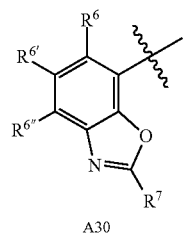

A30

TABLE 6

Compounds of Formula (I') with benzothiazolyl tails

| C. No. | R¹' | R² | X | A | R⁵ | R⁶ | R⁶' | R⁶" | R⁷ | R⁷' | R⁸ |
|---|---|---|---|---|---|---|---|---|---|---|---|
| 6.01 | Me | Cl | CF | A08 | | | | | | | |
| 6.02 | H | Cl | CF | A08 | | | | | | | |

A is A8, A10, A31, or A32:

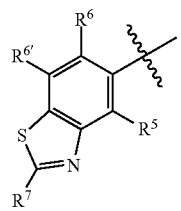

A8

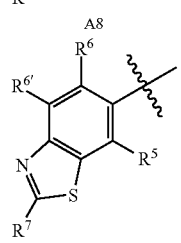

A10

TABLE 6-continued

Compounds of Formula (I') with benzothiazolyl tails

| C. No. | R¹' | R² | X | A | R⁵ | R⁶ | R⁶' | R⁶" | R⁷ | R⁷' | R⁸ |
|---|---|---|---|---|---|---|---|---|---|---|---|

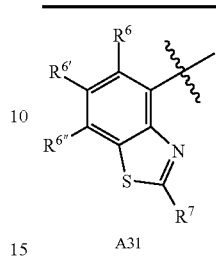

A31

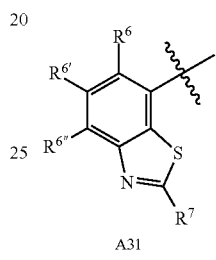

A31

TABLE 7

Compounds of Formula (I') with 1H-benzimidazolyl tails

| C. No. | R¹' | R² | X | A | R⁵ | R⁶ | R⁶' | R⁶" | R⁷ | R⁷' | R⁸ |
|---|---|---|---|---|---|---|---|---|---|---|---|
| 7.01 | Me | Cl | CF | A12 | | | | | | | |
| 7.02 | Me | Cl | CF | A12 | | | | | | | | Me |
| 7.03 | H | Cl | CF | A12 | | | | | | | | Me |

A is one of groups A11 and A12:

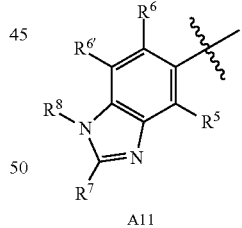

A11

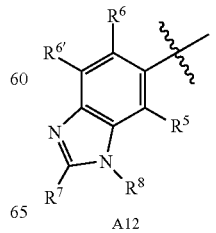

A12

TABLE 8

Compounds of Formula (I') with indoxazinyl tails

| C. No. | $R^{1'}$ | $R^2$ | X | A | $R^5$ | $R^6$ | $R^{6'}$ | $R^{6''}$ | $R^7$ | $R^{7'}$ | $R^8$ |
|---|---|---|---|---|---|---|---|---|---|---|---|
| 8.01 | Me | Cl | CF | A16 | | | | | NMe$_2$ | | |

A is A4, A16, A33, or A34:

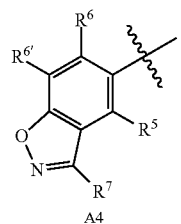
A4

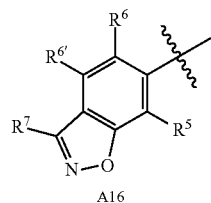
A16

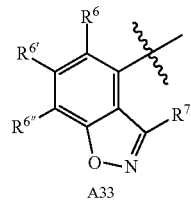
A33

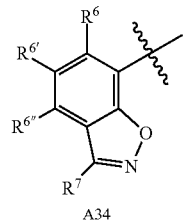
A34

TABLE 9

Compounds of Formula (I') with 1H-benzotriazolyl tails

| C. No. | $R^{1'}$ | $R^2$ | X | A | $R^5$ | $R^6$ | $R^{6'}$ | $R^{6''}$ | $R^7$ | $R^{7'}$ | $R^8$ |
|---|---|---|---|---|---|---|---|---|---|---|---|
| 9.01 | Me | Cl | CH | A20 | | | | | | | |

A is A19 or A20:

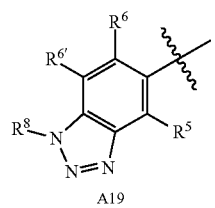
A19

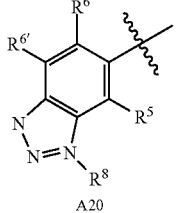
A20

Methods of Preparing the Compounds

Exemplary procedures to synthesize the compounds of Formula (I) are provided below.

The 4-amino-6-(heterocyclic)picolinic acids of Formula (I) can be prepared in a number of ways. As depicted in Scheme I, the 4-amino-6-chloropicolinates of Formula (II) can be converted to the 4-amino-6-substituted-picolinates of Formula (III), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_1$). 4-Amino-6-substituted-picolinates of Formula (III) can be transformed into the 5-iodo-4-amino-6-substituted-picolinates of Formula (IV) via a reaction with iodinating reagents, such as periodic acid and iodine, in a polar, protic solvent, such as methyl alcohol (reaction $b_1$). Stille coupling of the 5-iodo-4-amino-6-substituted-picolinates of Formula (IV) with a stannane, such as tetramethyltin, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 5-(substituted)-4-amino-6-substituted-picolinates of Formula (I-A), wherein $Z_1$ is alkyl, alkenyl, alkynyl, haloalkenyl and alkylthio (reaction $c_1$).

Alternatively, 4-amino-6-chloropicolinates of Formula (II) can be transformed to the 5-iodo-4-amino-6-chloropicolinates of Formula (V) via a reaction with iodinating reagents, such as periodic acid and iodine, in a polar, protic solvent, such as methyl alcohol (reaction $b_2$). Stille coupling of the 5-iodo-4-amino-6-chloropicolinates of Formula (V) with a stannane, such as tetramethyltin, in the presence of a catalyst, such as bis(triphenylphosphine)-palladium(II) dichloride, in a non-reactive solvent, such as 1,2-dichloroethane, at a temperature, such as 120-130° C., e.g., in a microwave reactor, provides 5-(substituted)-4-amino-6-chloropicolinates of Formula (VI), wherein $Z_1$ is alkyl, alkenyl, alkynyl, haloalkenyl and alkylthio (reaction $c_2$). The 5-substituted-4-amino-6-chloropicolinates of Formula (VI) can be converted to the 5-substituted-4-amino-6-substituted-picolinates of Formula (I-A), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_2$).

Scheme I

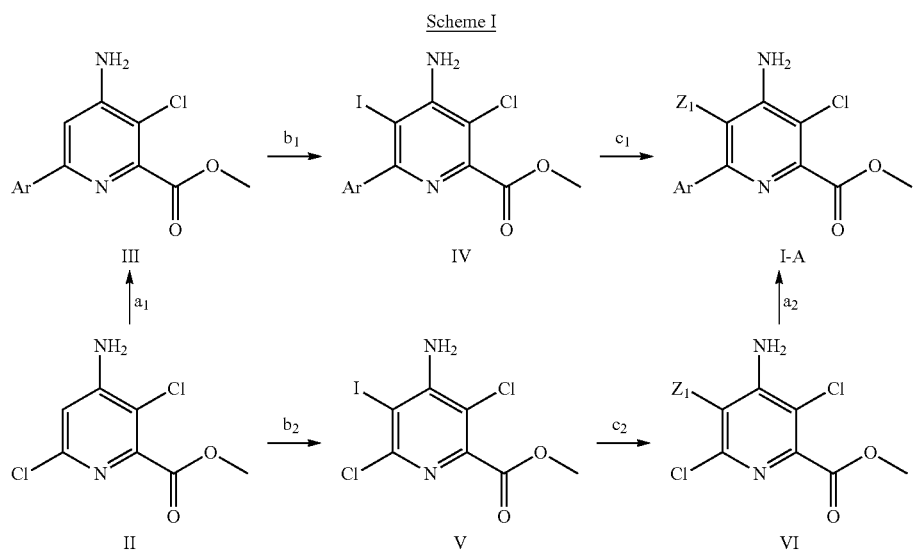

As depicted in Scheme II, the 4,5,6-trichloropicolinate of Formula (VII) can be converted to the corresponding isopropyl ester of Formula (VIII), via a reaction with isopropyl alcohol and concentrated sulfuric acid, e.g., at reflux temperature under Dean-Stark conditions (reaction d). The isopropyl ester of Formula (VIII) can be reacted with a fluoride ion source, such as cesium fluoride, in a polar, aprotic solvent, such as dimethyl sulfoxide, at a temperature, such as 80° C., under Dean-Stark conditions, to yield the isopropyl 4,5,6-trifluoropicolinate of Formula (IX) (reaction e). The isopropyl 4,5,6-trifluoropicolinate of Formula (IX) can be aminated with a nitrogen source, such as ammonia, in a polar, aprotic solvent, such as dimethyl sulfoxide, to produce a 4-amino-5,6-difluoropicolinate of Formula (X) (reaction f). The fluoro substituent in the 6-position of the 4-amino-5,6-difluoropicolinate of Formula (X) can be exchanged with a chloro substituent by treatment with a chloride source, such as hydrogen chloride, e.g., in dioxane, in a Parr reactor, at a temperature, such as 100° C., to produce a 4-amino-5-fluoro-6-chloro-picolinate of Formula (XI) (reaction g). The 4-amino-5-fluoro-6-chloropicolinate of Formula (XI) can be transesterified to the corresponding methyl ester of Formula (XII) by reaction with titanium(IV) isopropoxide in methyl alcohol at reflux temperature (reaction h).

Scheme II

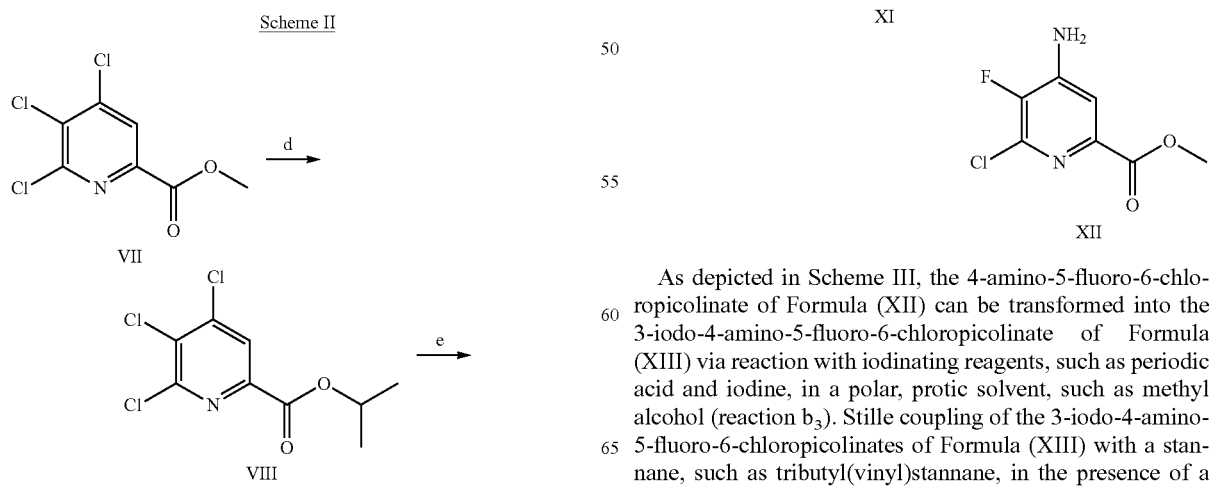

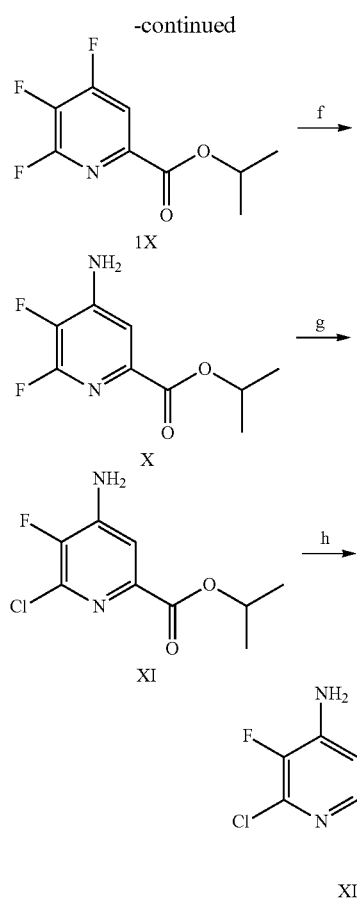

As depicted in Scheme III, the 4-amino-5-fluoro-6-chloropicolinate of Formula (XII) can be transformed into the 3-iodo-4-amino-5-fluoro-6-chloropicolinate of Formula (XIII) via reaction with iodinating reagents, such as periodic acid and iodine, in a polar, protic solvent, such as methyl alcohol (reaction $b_3$). Stille coupling of the 3-iodo-4-amino-5-fluoro-6-chloropicolinates of Formula (XIII) with a stannane, such as tributyl(vinyl)stannane, in the presence of a catalyst, such as bis(triphenylphosphine)-palladium(II)

dichloride, in a non-reactive solvent, such as 1,2-dichloroethane, at a temperature, such as 120-130° C., e.g., in a microwave reactor, provides 3-(substituted)-4-amino-5-fluoro-6-chloropicolinates of Formula (XIV), wherein $R^2$ is alkyl, alkenyl, alkynyl, haloalkenyl and alkylthio (reaction $c_3$). Alternatively, the 3-iodo-4-amino-5-fluoro-6-chloropicolinates of Formula (XIII) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-chloropicolinic acids of Formula (XIV), wherein $R^2$ is alkoxy or haloalkoxy (reaction $i_1$), which can be esterified to the methyl esters, e.g., by treatment with hydrogen chloride (gas) and methyl alcohol at 50° C. (reaction $j_1$). The 3-(substituted)-4-amino-5-fluoro-6-microwave reactor, provides 3-(substituted)-4-amino-5-fluoro-6-substituted-picolinates of Formula (I-B), wherein $R^2$ is alkyl, alkenyl, alkynyl, haloalkenyl and alkylthio (reaction $c_4$). Alternatively, the 3-iodo-4-amino-5-fluoro-6-substituted-picolinates of Formula (XVI) can be treated with cesium carbonate and a catalytic amount of both copper(I) iodide and 1,10-phenanthroline in the presence of a polar, protic solvent, such as methyl alcohol, at a temperature, such as 65° C., to provide a 3-(substituted)-4-amino-5-fluoro-6-substituted-picolinic acids of Formula (I-B), wherein $R^2$ is alkoxy or haloalkoxy (reaction $i_2$), which can be esterified to the methyl esters, e.g., by treatment with hydrogen chloride (gas) and methyl alcohol, at a temperature, such as 50° C. (reaction $j_2$).

Scheme III

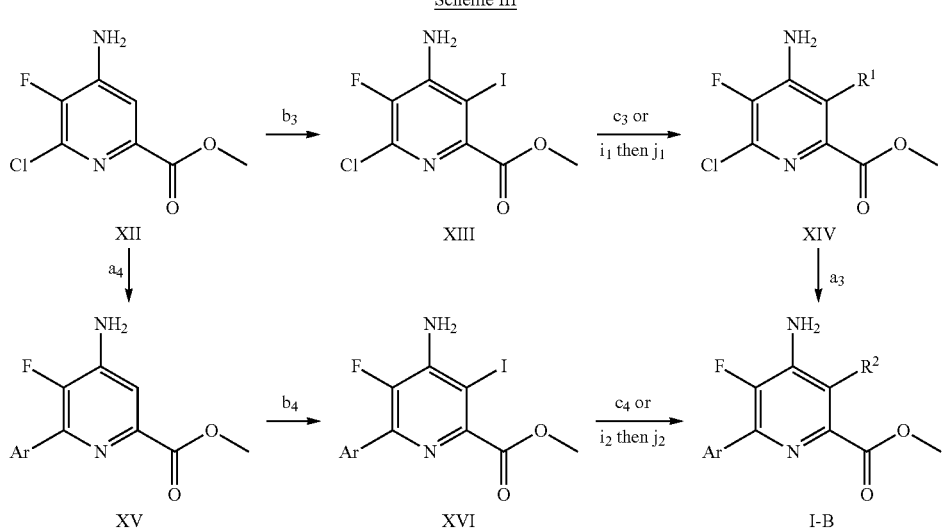

chloropicolinates of Formula (XIV) can be converted to the 4-amino-6-substituted-picolinates of Formula (I-B), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_3$).

Alternatively, the 4-amino-5-fluoro-6-chloropicolinates of Formula (XII) can be converted to the 4-amino-5-fluoro-6-substituted-picolinates of Formula (XV), wherein Ar is as herein defined, via Suzuki coupling with a boronic acid or ester, in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_4$). The 4-amino-5-fluoro-6-substituted-picolinates of Formula (XV) can be transformed into the 3-iodo-4-amino-5-fluoro-6-substituted-picolinates of Formula (XVI) via reaction with iodinating reagents, such as periodic acid and iodine, in a polar, protic solvent, such as methyl alcohol (reaction $b_4$). Stille coupling of the 3-iodo-4-amino-5-fluoro-6-substituted-picolinates of Formula (XVI) with a stannane, such as tributyl(vinyl)stannane, in the presence of a catalyst, such as bis(triphenylphosphine)-palladium(II) dichloride, in a non-reactive solvent, such as 1,2-dichloroethane, at a temperature, such as 120-130° C., e.g., in a As depicted in Scheme IV, the 4-acetamido-6-(trimethylstannyl)picolinates of Formula (XVII) can be converted to the 4-acetamido-6-substituted-picolinates of Formula (XVIII), wherein Ar is as herein defined, via Still coupling with an aryl bromide or aryl iodide, in the presence of a catalyst, such as bis(triphenylphosphine)-palladium(II) dichloride, in a solvent, such as dichloroethane, e.g., at reflux temperature (reaction k). 4-Amino-6-substituted-picolinates of Formula (I-C), wherein Ar is as herein defined, can be synthesized from 4-acetamido-6-substituted-picolinates of Formula (XVIII) via standard deprotecting methods, such as hydrochloric acid gas in methanol (reaction 1).

Scheme IV

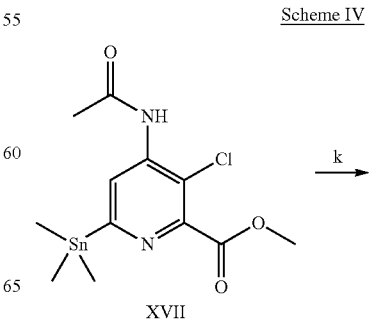

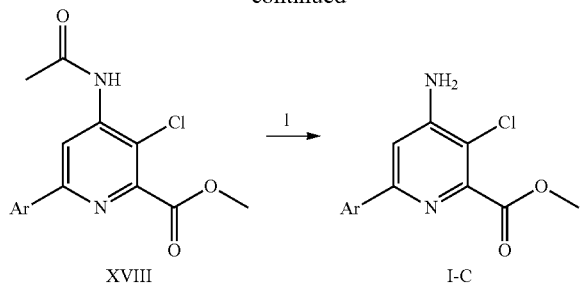

As depicted in Scheme V, 2,4-dichloro-5-methoxypyrimidine (XIX) can be transformed into 2,4-dichloro-5-methoxy-6-vinylpyrimidine (XX) via a reaction with vinyl magnesium bromide, in a polar, aprotic solvent, such as tetrahydrofuran (reaction m). 2,4-Dichloro-5-methoxy-6-vinylpyrimidine (XX) can be transformed into 2,6-dichloro-5-methoxypyrimidine-4-carboxaldehyde (XXI) via treatment with ozone, e.g., in a dichloromethane:methanol solvent mixture (reaction n). 2,6-Dichloro-5-methoxypyrimidine-4-carboxaldehyde (XXI) can be transformed into methyl 2,6-dichloro-5-methoxypyrimidine-4-carboxylate (XXII) via treatment with bromine, e.g., in a methanol:water solvent mixture (reaction o). Methyl 2,6-dichloro-5-methoxypyrimidine-4-carboxylate (XXII) can be transformed into methyl 6-amino-2-chloro-5-methoxypyrimidine-4-carboxylate (XXIII) via treatment with ammonia (e.g., 2 equivalents) in a solvent, such as DMSO (reaction p). Finally, 6-amino-2-substituted-5-methoxypyrimidine-4-carboxylates of Formula (I-D), wherein Ar is as herein defined, can be prepared via Suzuki coupling with a boronic acid or ester, with 6-amino-2-chloro-5-methoxypyrimidine-4-carboxylate (XXIII), in the presence of a base, such as potassium fluoride, and a catalyst, such as bis(triphenylphosphine)-palladium(II) dichloride, in a polar, protic solvent mixture, such as acetonitrile-water, at a temperature, such as 110° C., e.g., in a microwave reactor (reaction $a_5$).

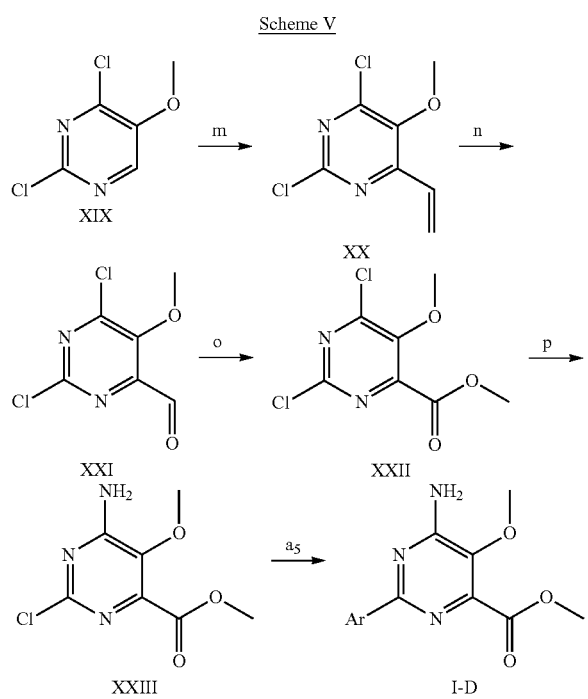

Scheme V

The compounds of Formulae I-A, I-B, I-C, and I-D obtained by any of these processes, can be recovered by conventional means and purified by standard procedures, such as by recrystallization or chromatography. The compounds of Formula (I) can be prepared from compounds of Formulae I-A, I-B, I-C, and I-D using standard methods well known in the art.

Compositions and Methods

In some embodiments, the compounds provided herein are employed in mixtures containing an herbicidally effective amount of the compound along with at least one agriculturally acceptable adjuvant or carrier. Exemplary adjuvants or carriers include those that are not phytotoxic or significantly phytotoxic to valuable crops, e.g., at the concentrations employed in applying the compositions for selective weed control in the presence of crops, and/or do not react or significantly react chemically with the compounds of provided herein or other composition ingredients. Such mixtures can be designed for application directly to weeds or their locus or can be concentrates or formulations that are \diluted with additional carriers and adjuvants before application. They can be solids, such as, for example, dusts, granules, water dispersible granules, or wettable powders, or liquids, such as, and for example, emulsifiable concentrates, solutions, emulsions or suspensions. They can also be provided as a pre-mix or tank-mixed.

Suitable agricultural adjuvants and carriers that are useful in preparing the herbicidal mixtures of the disclosure are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

In some embodiments, one or more surface-active agents are utilized in the compositions of the present disclosure. Such surface-active agents are, in some embodiments, employed in both solid and liquid compositions, e.g., those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in McCutcheon's *Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this disclosure is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation or flood water, and by other conventional means known to those skilled in the art.

In some embodiments, the compounds and compositions described herein are applied as a post-emergence application, pre-emergence application, in-water application to flooded paddy rice or water bodies (e.g., ponds, lakes and streams), or burn-down application.

In some embodiments, the compounds and compositions provided herein are utilized to control weeds in crops, including but not limited to citrus, apple, rubber, oild palm, forestry, direct-seeded, water-seeded and transplanted rice, wheat, barley, oats, rye, sorghum, corn/maize, pastures, grasslands, rangelands, fallowland, turf, tree and vine orchards, aquatics, or row-crops, as well as non-crop settings, e.g., industrial vegetation management or rights of way. In some embodiments, the compounds and compositions are used to control woody plants, broadleaf and grass weeds, or sedges.

In some embodiments, the compounds and compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall panicum, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burnt F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the compounds and compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam.

(Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compounds and compostions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compounds and compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly sida, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, application rates of about 1 to about 4,000 grams/hectare (g/ha) are employed in post-emergence operations. In some embodiments, rates of about 1 to about 4,000 g/ha are employed in pre-emergence operations.

In some embodiments, the compounds, compositions, and methods provided herein are used in conjunction with one or more other herbicides to control a wider variety of undesirable vegetation When used in conjunction with other herbicides, the presently claimed compounds can be formulated with the other herbicide or herbicides, tank-mixed with the other herbicide or herbicides or applied sequentially with the other herbicide or herbicides. Some of the herbicides that can be employed in conjunction with the compounds of the present disclosure include: 4-CPA; 4-CPB; 4-CPP; 2,4-D; 2,4-D choline salt, 2,4-D esters and amines; 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halosafen, halosulfuron-methyl, haloxydine, haloxyfop-methyl, haloxyfop-P-methyl, halauxifen-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The compounds and compositions of the present disclosure can generally be employed in combination with known herbicide safeners, such as benoxacor, benthiocarb, brassinolide, cloquintocet (e.g., mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenylsulfonylbenzoic acid amides, to enhance their selectivity.

The compounds, compositions, and methods described herein can be used to control undesirable vegetation on glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate dioxygenase (HPPD) inhibitor-tolerant-, protoporphyrinogen oxidase (PPO) inhibitor-tolerant-, triazine-tolerant-, bromoxynil-tolerant-crops (such as, but not limited to, soybean, cotton, canola/oilseed rape, rice, cereals, corn, turf, etc), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil The compositions and methods may be used in controlling undesirable vegetation in crops possessing multiple or stacked traits conferring tolerance to multiple chemistries and/or inhibitors of multiple modes of action.

The compounds and compositions provided herein may also be employed to control herbicide resistant or tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

Synthesis of Precursers

Preparation 1: Methyl 4-amino-3,6-dichloropicolinate (Head A)

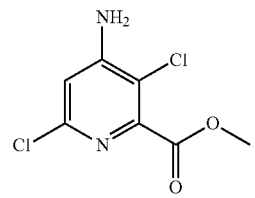

Prepared as described in Fields et al., WO 2001051468 A1.

Preparation 2: Methyl 4-amino-3,6-dichloro-5-fluoropicolinate (Head B)

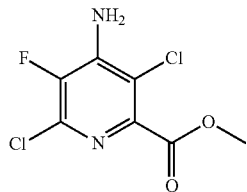

Prepared as described in Fields et al., Tetrahedron Letters (2010), 51(1), 79-81.

Preparation 3: 2,6-Dichloro-5-methoxy-4-vinyl pyrimidine

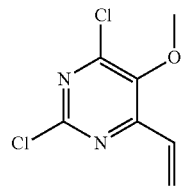

To a solution of commercially available 2,6-dichloro-5-methoxy pyrimidine (100 g, 0.55 mol) in dry tetrahydrofuran was added, dropwise, 1M vinyl magnesium bromide in tetrahydrofuran solvent (124 g, 0.94 mol) over one hour (h) at room temperature. The mixture was then stirred for 4 h at room temperature. Excess Grignard reagent was quenched by addition of acetone (200 mL) while the temperature of the mixture was maintained at a temperature below 20° C. Thereafter, 2,3-dichloro-5,6-dicyano-p-benzoquinone (DDQ) (151 g, 0.67 mol) was added at once and stirred overnight. A yellow solid precipitated out. The solid was filtered and washed with ethyl acetate (500 mL). The filtrate was concentrated under reduced pressure and the resulting crude compound was diluted with ethyl acetate (2 L). The resulting undissolved, dark, semi-solid was separated by filtration using ethyl acetate. It was further concentrated under reduced pressure to provide a crude compound, which was purified by column chromatography. The compound was eluted with 5% to 10% ethyl acetate in hexane mixture to provide the title compound (70 g, 60%): mp 60-61° C.; $^1$H NMR (CDCl$_3$) δ 3.99 (s, 3H), 5.85 (d, 1H), 6.75 (d, 1H), 6.95 (dd, 1H).

Preparation 4: 2,6-Dichloro-5-methoxy-pyrimidine-4-carbaldehyde

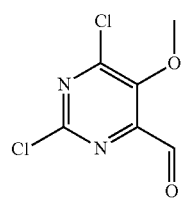

A solution of 2,6-dichloro-5-methoxy-4-vinyl pyrimidine (50 g, 0.24 mol) in dichloromethane:methanol (4:1, 2 L) was cooled to −78° C. Ozone gas was bubbled therethrough for 5 h. The reaction was quenched with dimethyl sulfide (50 mL). The mixture was slowly warmed to room temperature and concentrated under reduced pressure at 40° C. to provide the title compound (50.5 g, 100%); HPLC (85% acetonitrile buffered with 0.1% v/v acetic acid).

Preparation 5: Methyl 2,6-dichloro-5-methoxy-pyrimidine-4-carboxylate

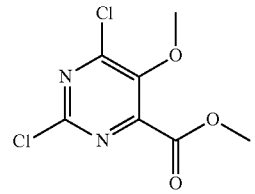

A solution of 2,6-dichloro-5-methoxy-pyrimidine-4-carbaldehyde (50 g, 0.24 mol) in methanol (1 L) and water (60 mL) was prepared. To the solution, sodium bicarbonate (400 g) was added. A 2 M solution of bromine (192 g, 1.2 mol) in methanol/water (600 mL, 9:1 was added, dropwise, to the pyrimidine solution for 45 minutes (min) at 0° C. while stirring the mixture. The stirring was continued at the same temperature for 1 h. Later, the mixture was stirred at room temperature for 4 h. While stirring, the reaction mixture was thereafter poured onto a mixture of crushed ice (2 L), sodium bisulfite (50 g), and sodium chloride (200 g). The product was extracted with ethyl acetate (1 L×2), and the combined organic layer was dried over sodium sulfate and filtered. Evaporation of the solvent under reduced pressure produced a thick material, which solidified on long standing to afford the title compound (50.8 g, 87%); ESIMS m/z 238 ([M+H]$^+$).

Preparation 6: Methyl 6-amino-2-chloro-5-methoxy-pyrimidine-4-carboxylate (Head C)

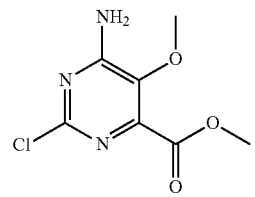

A solution of methyl 2,6-dichloro-5-methoxy-pyrimidine-4-carboxylate (25 g, 0.1 mol) and dimethyl sulfoxide (DMSO) was prepared. To this solution was added, at 0-5° C., a solution of ammonia (2 eq) in DMSO. This mixture was stirred at the same 0-5° C. temperature for 10 to 15 min Later, the mixture was diluted with ethyl acetate, and the resulting solid was filtered off. The ethyl acetate filtrate was washed with a brine solution and dried over sodium sulfate. Upon concentration, the crude product was obtained. The crude product was stirred in a minimum amount of ethyl acetate and filtered to obtain the pure compound. Additional pure compound was obtained from the filtrate which, after concentration, was purified by flash chromatography. This produced the title compound (11 g, 50%): mp 158° C.; $^1$H NMR (DMSO-d$_6$) δ 3.71 (s, 3H), 3.86 (s, 3H), 7.65 (brs, 1H), 8.01 (brs, 1H).

Preparation 7: Methyl 4-amino-3,6-dichloro-5-iodopicolinate

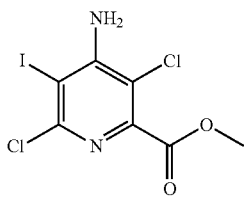

Methyl 4-amino-3,6-dichloropicolinate (10.0 g, 45.2 mmol), periodic acid (3.93 g, 17.2 mmol), and iodine (11.44 g, 45.1 mmol) were dissolved in methanol (30 mL) and refluxed at 60° C. for 27 h. The reaction mixture was concentrated, diluted with diethyl ether, and washed twice with saturated aqueous sodium bisulfite. The aqueous layers were extracted once with diethyl ether, and the combined organic layers were dried over anhydrous sodium sulfate. The product was concentrated and purified by flash chromatography (silica gel, 0-50% ethyl acetate/hexanes) to provide the title compound as a pale yellow solid (12.44 g, 35.9 mmol, 79%): mp 130.0-131.5° C.; $^1$H NMR (400 MHz, CDCl$_3$) δ 5.56 (s, 2H), 3.97 (s, 3H); $^{13}$C NMR (101 MHz, CDCl$_3$) δ 163.80, 153.00, 152.75, 145.63, 112.12, 83.91, 53.21; EIMS m/z 346.

Preparation 8: Methyl 4-amino-3,6-dichloro-5-methylpicolinate (Head D)

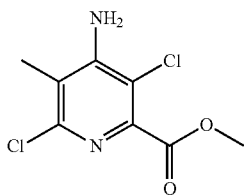

A mixture of methyl 4-amino-3,6-dichloro-5-iodopicolinate (8.1 g, 23.4 mmol), tetramethylstannane (8.35 g, 46.7 mmol), and bis(triphenylphosphine)palladium(II) chloride (2.5 g, 3.5 mmol) in 1,2-dichloroethane (40 mL) was irradiated in a Biotage Initiator microwave at 120° C. for 30 min, with external IR-sensor temperature monitoring from the side. The reaction mixture was loaded directly onto a silica gel cartridge and purified by flash chromatography (silica gel, 0-50% ethyl acetate/hexanes) to provide the title compound as an orange solid (4.53 g, 19.27 mmol, 83%): mp 133-136° C.; $^1$H NMR (400 MHz, CDCl$_3$) δ 4.92 (s, 2H), 3.96 (s, 3H), 2.29 (s, 3H); $^{13}$C NMR (101 MHz, CDCl$_3$) δ 164.34, 150.24, 148.69, 143.94, 117.01, 114.60, 53.02, 14.40; ESIMS m/z 236 ([M+H]$^+$), 234 ([M−H]$^−$).

Preparation 9: Methyl 6-amino-2,5-dichloropyrimidine-4-carboxylate (Head E)

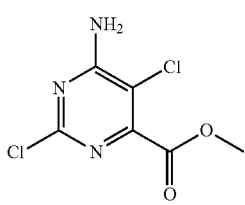

Prepared as described in Epp et al., WO 2007082076 A1.

Preparation 10: Methyl 4-amino-6-chloro-5-fluoro-3-methoxypicolinate (Head F)

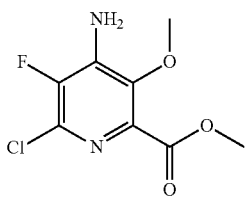

Prepared as described in Epp et al., WO 2013003740 A1.

Preparation 11: Methyl 4-amino-6-chloro-5-fluoro-3-vinylpicolinate (Head G)

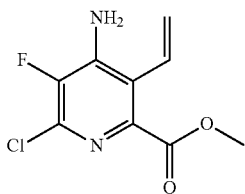

Methyl 4-amino-6-chloro-5-fluoro-3-iodopicolinate (7.05 g, 21.33 mmol, prepared as described in Epp et al., WO 2013003740 A1) and vinyltri-n-butyltin (7.52 mL, 25.6 mmol) were suspended in dichloroethane (71.1 mL) and the mixture was degassed with Argon for 10 min bis(triphenylphosphine)palladium(II) chloride (1.497 g, 2.133 mmol) was then added and the reaction mixture was stirred at 70° C. overnight (clear orange solution). The reaction was monitored by GCMS. After 20 h, the reaction mixture was concentrated, adsorbed onto Celite, and purified by column chromatography (SiO2, hexanes/ethyl acetate gradient) to afford the title compound as a light brown solid (3.23 g, 65.7%) as a light brown solid: mp 99-100° C.; $^1$H NMR (400 MHz, CDCl$_3$) δ 6.87 (dd, J=18.1, 11.6 Hz, 1H), 5.72 (dd, J=11.5, 1.3 Hz, 1H), 5.52 (dd, J=18.2, 1.3 Hz, 1H), 4.79 (s, 2H), 3.91 (s, 3H); $^{19}$F NMR (376 MHz, CDCl$_3$) δ −138.79 (s); EIMS m/z 230.

Preparation 12: Methyl 4-amino-3,5,6-trichloropicolinate (Head H)

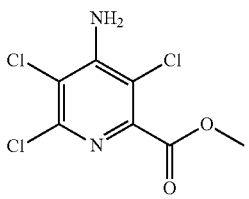

Prepared as described in Finkelstein et al., WO 2006062979 A1.

Preparation 13: Methyl 4-amino-6-bromo-3-chloro-5-fluoropicolinate (Head I)

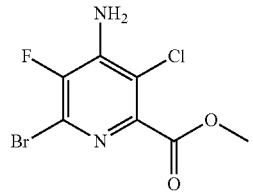

Prepared as described in Arndt et al., US 20120190857 A1.

Preparation 14: Methyl 4-amino-3-chloro-5-fluoro-6-(trimethylstannyl)picolinate (Head J)

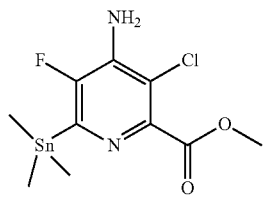

Methyl 4-amino-6-bromo-3-chloro-5-fluoropicolinate (500 mg, 1.8 mmol), 1,1,1,2,2,2-hexamethyldistannane (580 mg, 1.8 mmol) and bis(triphenylphosphine)-palladium(II) chloride (120 mg, 0.18 mmol) were combined in 6 mL dry dioxane, sparged with a stream of nitrogen for 10 min and then heated to 80° C. for 2 h. The cooled mixture was stirred with 25 mL ethyl acetate and 25 mL saturated NaCl for 15 min. The organic phase was separated, filtered through diatomaceous earth, dried (Na$_2$SO$_4$) and evaporated. The residue was taken up in 4 mL ethyl acetate, stirred and treated in portions with 15 mL hexane. The milky white solution was decanted from any solids produced, filtered through glass wool and evaporated to give the title compound as an off-white solid (660 mg, 100%): $^1$H NMR (400 MHz, CDCl$_3$) δ 4.63 (d, J=29.1 Hz, 1H), 3.97 (s, 2H), 0.39 (s, 4H); $^{19}$F NMR (376 MHz, CDCl$_3$) δ −130.28; EIMS m/z 366.

Preparation 15: Methyl 4-acetamido-3-chloro-6-(trimethylstannyl)-picolinate (Head K)

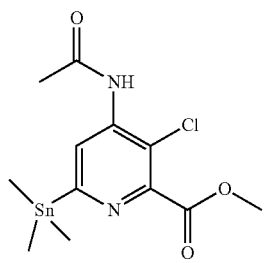

Prepared as described in Balko et al., WO 2003011853 A1.

Preparation 16: Methyl 4-acetamido-3,6-dichloropicolinate (Head L)

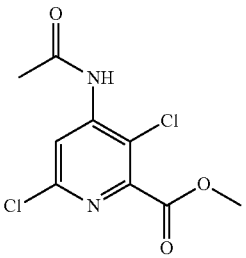 [SMILES: COC(=O)c1nc(Cl)cc(NC(C)=O)c1Cl]

Prepared as described in Fields et al., WO 2001051468 A1.

Preparation 17: Methyl 4-amino-3-chloro-6-iodopicolinate (Head M)

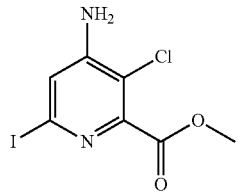

Prepared as described in Balko et al., WO 2007082098 A2.

Preparation 18: Methyl 4-acetamido-3-chloro-6-iodopicolinate (Head N)

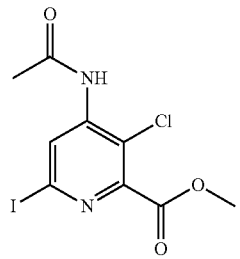 [SMILES: COC(=O)c1nc(I)cc(NC(C)=O)c1Cl]

Prepared as described in Balko et al., WO 2007082098 A2.

Preparation 19: Methyl 4-amino-6-bromo-3,5-difluoropicolinate (Head O)

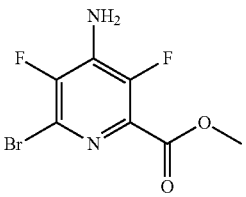

Prepared as described in Fields et al., WO 2001051468 A1.

Preparation 20: Methyl 6-amino-2-chloro-5-vinylpyrimidine-4-carboxylate (Head P)

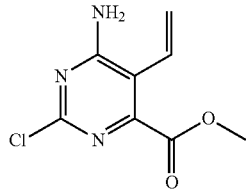

Prepared as described in Epp et al., US20090088322.

Preparation 21: 1-Bromo-4-(2,2-diethoxyethoxy)-2-fluorobenzene

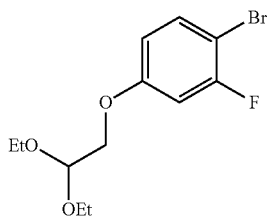 [SMILES: CCOC(COc1ccc(Br)c(F)c1)OCC]

4-Bromo-3-fluorophenol (7 g, 0.03665 mol) and potassium carbonate (7.6 g, 0.055 mol) were dissolved in N,N-dimethylformamide (9 mL). 2-Bromo-1,1-diethoxyethane (8.5 mL, 0.055 mol) was added and the reaction mixture was stirred and heated to 135° C. for 7 h. The solvent was removed after the reaction was completed. The residue was dissolved in ethyl acetate and washed with 2M NaOH solution. The organic phase was dried over $Na_2SO_4$. The solvent was evaporated to yield 1-bromo-4-(2,2-diethoxyethoxy)-2-fluorobenzene as an oil (11.4 g, 100%).

Preparation 22: 1-Bromo-3-(2,2-diethoxyethoxy)-2-fluorobenzene

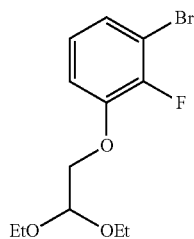

1-bromo-3-(2,2-diethoxyethoxy)-2-fluorobenzene was prepared from 3-bromo-2-fluorophenol as described in Preparation 81.

Preparation 23: 2-Bromo-4-(2,2-diethoxyethoxy)-1-fluorobenzene

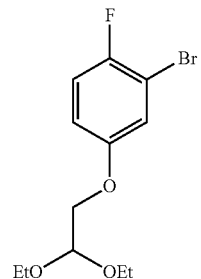 [SMILES: CCOC(COc1ccc(F)c(Br)c1)OCC]

2-bromo-4-(2,2-diethoxyethoxy)-1-fluorobenzene was prepared from 3-bromo-4-fluorophenol as described in Preparation 81.

Preparation 24: 1-Bromo-4-chloro-2-(2,2-diethoxyethoxyl)benzene

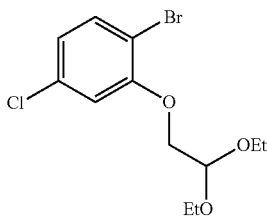 [SMILES: CCOC(COc1cc(Cl)ccc1Br)OCC]

1-bromo-4-chloro-2-(2,2-diethoxyethoxyl)benzene was prepared from 2-bromo-5-chlorophenol as described in Preparation 81.

Preparation 25: (4-Bromo-3-fluorophenyl)(2,2-diethoxyethyl)sulfane

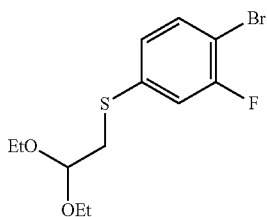 [SMILES: CCOC(CSc1ccc(Br)c(F)c1)OCC]

(4-bromo-3-fluorophenyl)(2,2-diethoxyethyl)sulfane was prepared from 4-bromo-3-fluorobenzenethiol as described in Preparation 81.

Preparation 26: 4-Bromo-7-chlorobenzofuran

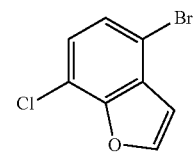 [SMILES: Clc1ccc(Br)c2ccoc12]

To 80 mL of benzene was added polyphosphoric acid (3.47 g, 36.9 mmol) and commercially available 2-(5-bromo-2-chlorophenoxy)acetaldehyde (9.2 g, 36.9 mmol) and separated into eight 20 mL vials containing equal amounts. The vials were heated with an external temperature of 90° C. for 4 days. Upon cooling of the reaction, the benzene was removed by decanting. Celite (50 g) was added to the organic solution and the solvent was removed using a rotary evaporator. The impregnated Celite was loaded onto a Teledyne-Isco purification system and purified by silica gel chromatography using 0-30% ethyl acetate:hexanes to give 4-bromo-7-chlorobenzofuran as a white solid (2.7 g, 32%): $^1$H NMR (400 MHz, CDCl$_3$) δ 7.73 (d, J=2.2 Hz, 1H), 7.33 (d, J=8.3 Hz, 1H), 7.18 (d, J=8.3 Hz, 1H), 6.85 (d, J=2.2 Hz, 1H); $^{13}$C NMR (101 MHz, CDCl$_3$) δ 150.38 (s), 146.14 (s), 130.27 (s), 126.56 (s), 125.32 (s), 116.44 (s), 112.49 (s), 107.71 (s); ESIMS m/z 232 ([M+H]$^+$), 230 ([M−H]$^−$).

Preparation 27: 6-Bromobenzofuran and 4-bromobenzofuran

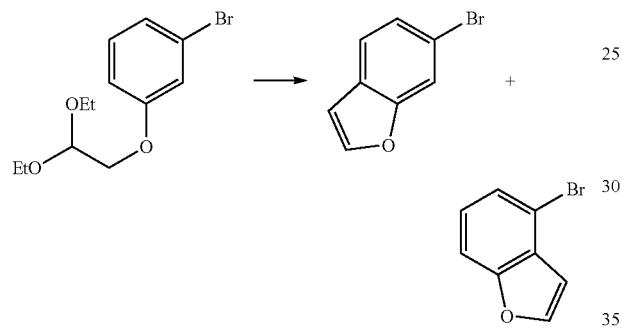

6-Bromobenzofuran and 4-bromobenzofuran were prepared as described in US20040147559 from 1-bromo-3-(2,2-diethoxyethoxyl)benzene.

Preparation 28: 5-Bromo-6-fluorobenzofuran and 5-bromo-4-fluorobenzofuran

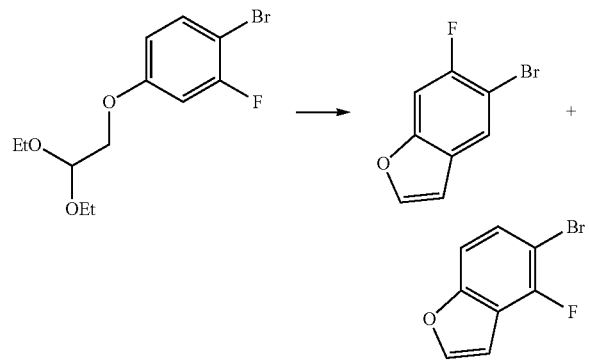

1-Bromo-4-(2,2-diethoxyethoxy)-2-fluorobenzene (11.4 g, 0.037 mol) was dissolved in toluene (78 mL). Polyphosphoric acid (11.9 g) was added and the mixture was heated to reflux for 5 h. The solvent was removed and the residue was diluted with water and ethyl acetate. The organic phase was washed with 2M NaOH solution and then dried over Na$_2$SO$_4$. A mixture of 5-bromo-6-fluorobenzofuran and 5-bromo-4-fluorobenzofuran (4.8 g, 60.3%) were obtained as a mixture after purification via column chromatography.

Preparation 29: 6-Bromo-7-fluorobenzofuran

6-Bromo-7-fluorobenzofuran was prepared from 1-bromo-3-(2,2-diethoxyethoxy)-2-fluorobenzene as described in Preparation 88; ESIMS m/z 216 ([M+H]$^+$).

Preparation 30: 6-Bromo-5-fluorobenzofuran

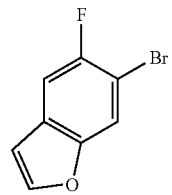 [SMILES: Fc1cc2ccoc2cc1Br]

6-Bromo-5-fluorobenzofuran was prepared from 2-bromo-4-(2,2-diethoxyethoxy)-1-fluorobenzene as described in Preparation 88: ESIMS m/z 216 ([M+H]$^+$).

Preparation 31: 7-Bromo-4-chlorobenzofuran

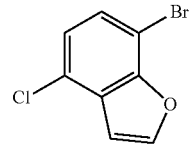 [SMILES: Clc1ccc(Br)c2occc12]

7-Bromo-4-chlorobenzofuran was prepared from 1-bromo-4-chloro-2-(2,2-diethoxyethoxyl)benzene as described in Preparation 88; ESIMS m/z 232 ([M+H]$^+$).

Preparation 32: 5-Bromo-4-fluorobenzo[b]thiophene and 5-bromo-6-fluorobenzo[b]thiophene

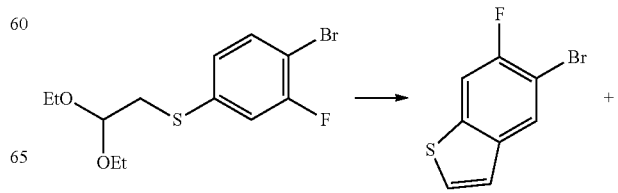

-continued

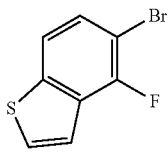

Polyphosphoric acid (13.9 g) was stirred in chlorobenzene (50 mL) at 130° C. (4-bromo-3-fluorophenyl)(2,2-diethoxyethyl)sulfane (7.7 g, 0.0238 mol) in chlorobenzene (15.4 mL) was added dropwise at 130° C. The mixture was then stirred at 130° C. for 10 h. The solvent was removed and the residue was extracted with toluene, hexane, and then water. The organic phase was combined and washed with saturated NaHCO$_3$ solution and brine, and then dried over Na$_2$SO$_4$. The products 5-bromo-4-fluorobenzo[b]thiophene and 5-bromo-6-fluorobenzo[b]thiophene were obtained after purification via column chromatography (3.6 g, 65.5%).

Preparation 33: Bromo-5-fluorobenzo[b]thiophene and 4-bromo-5-fluorobenzo[b]thiophene

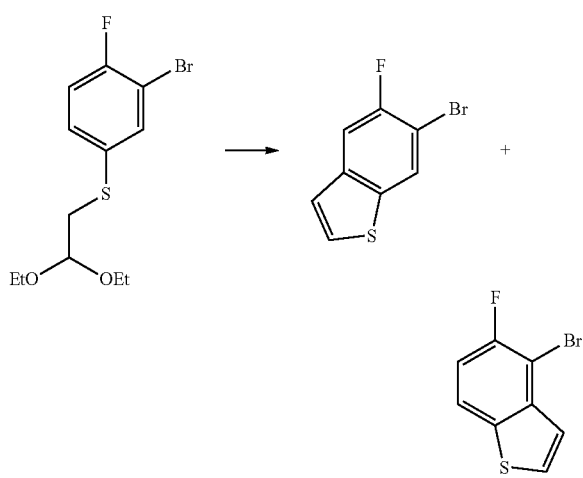

6-Bromo-5-fluorobenzo[b]thiophene and 4-bromo-5-fluorobenzo[b]thiophene were prepared from (3-bromo-4-fluorophenyl)(2,2-diethoxyethyl)sulfane as described in Preparation 81: ESIMS m/z 232 ([M+H]$^+$).

Preparation 34: 2-(7-Chlorobenzofuran-4-yl)-5,5-dimethyl-1,3,2-dioxaborinane

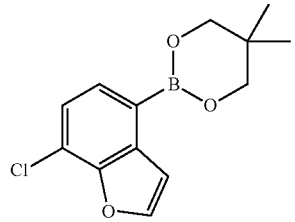 [SMILES: CC1(C)COB(c2ccc(Cl)c3occc23)OC1]

2-(7-Chlorobenzofuran-4-yl)-5,5-dimethyl-1,3,2-dioxaborinane was prepared as described in Preparation 94 from 4-bromo-7-chlorobenzofuran (prepared as described in WO2005056015) to afford a white solid (66%): IR (cm$^{-1}$) 669.18, 701.26, 741.33, 792.08, 773.25, 842.53, 811.66, 863.44, 876.27, 884.51, 953.31, 993.58, 1027.34, 1132.28, 1059.34, 1157.92, 1217.21, 1207.86, 1253.95, 1238.65, 1302.38, 1266.72, 1359.16, 1335.94, 1370.05, 1422.73, 1438.38, 1480.37, 1577.30, 1602.05, 2903.59, 2871.91, 2940.30, 2955.31, 3140.15, 3161.21; $^1$H NMR (400 MHz, CDCl$_3$) δ 7.69 (d, J=2.1 Hz, 1H), 7.63 (d, J=7.8 Hz, 1H), 7.28 (dd, J=6.7, 2.6 Hz, 1H), 7.27 (d, J=2.2 Hz, 1H), 3.82 (s, 4H), 1.05 (s, 6H); ESIMS m/z 265 ([M+H]$^+$), 263 ([M–H]$^-$).

Preparation 35: 2-(Benzofuran-6-yl)-4,4,5,5-tetramethyl-1,3,2-dioxaborolane and 2-(benzofuran-4-yl)-4,4,5,5-tetramethyl-1,3,2-dioxaborolane

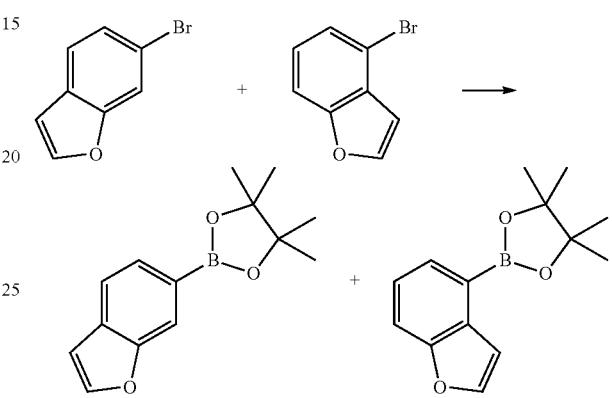

2-(Benzofuran-6-yl)-4,4,5,5-tetramethyl-1,3,2-dioxaborolane and 2-(benzofuran-4-yl)-4,4,5,5-tetramethyl-1,3,2-dioxaborolane were prepared as described in Preparation 94 from 4-bromobenzofuran and 6-bromobenzofuran to afford the mixture as a clear oil (48%): $^1$H NMR (400 MHz, CDCl$_3$) δ 7.97 (s, 1H), 7.72-7.68 (m, 1H), 7.66 (dd, J=4.9, 2.6 Hz, 2H), 7.60 (dd, J=8.0, 5.2 Hz, 2H), 7.30 (dd, J=7.1, 6.2 Hz, 1H), 7.28-7.21 (m, 2H), 6.77 (dd, J=2.1, 0.8 Hz, 1H), 1.37 (d, J=6.2 Hz, 22H), 1.29-1.22 (m, 8H); $^{13}$C NMR (101 MHz, CDCl$_3$) δ 146.01, 145.21, 130.19, 130.11, 128.76, 123.56, 120.60, 117.60, 114.05, 108.45, 106.63, 83.82, 83.69, 83.50, 25.02, 24.98, 24.88; ESIMS m/z 245 ([M+H]$^+$), 243 ([M–H]$^-$).

Preparation 36: 2-(6-Fluorobenzofuran-5-yl)-4,4,5,5-tetramethyl-1,3,2-dioxaborolane and 2-(4-fluorobenzofuran-5-yl)-4,4,5,5-tetramethyl-1,3,2-dioxaborolane

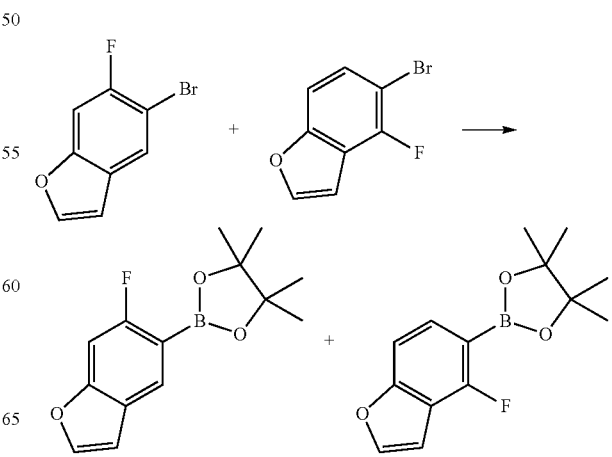

A mixture of 5-bromo-6-fluorobenzofuran and 5-bromo-4-fluorobenzofuran (1 combined equivalent), KOAc (3 eq) and bis(pinacolato) diboron (1.2 eq) were stirred in dioxane (0.1M with respect to 5-bromo-6-fluorobenzofuran and 5-bromo-4-fluorobenzofuran mixture) under nitrogen flow for 30 min. The catalyst PdCl$_2$(dppf) 0.15 eq was added and the nitrogen flow was maintained for 10 min. The reaction mixture was heated to 85° C. overnight. The solvent was removed, the residue was dissolved in methylene dichloride, and the solid was filtered. The filtrate was concentrated and purified through a column to give a mixture of 2-(6-fluorobenzofuran-5-yl)-4,4,5,5-tetramethyl-1,3,2-dioxaborolane and 2-(4-fluorobenzofuran-5-yl)-4,4,5,5-tetramethyl-1,3,2-dioxaborolane (63%): $^1$H NMR (400 MHz, CDCl$_3$) δ 7.98 (d, J=5.7 Hz, 1H), 7.59 (d, J=2.1 Hz, 1H), 7.18 (d, J=9.4 Hz, 1H), 6.73 (d, J=1.3 Hz, 1H), 1.38 (s, 12H); $^1$H NMR (400 MHz, CDCl$_3$) δ 7.81 (d, J=7.0 Hz, 1H), 7.37 (t, J=7.4 Hz, 1H), 7.30 (d, J=8.4 Hz, 1H), 6.87 (s, 1H), 1.38 (s, 12H); $^{19}$F NMR (376 MHz, CDCl$_3$) δ −107.80, −107.81, −107.82, −107.84, −108.47, −108.48; ESIMS m/z 262 ([M+H]$^+$).

Preparation 37: 2-(4-Chlorobenzofuran-7-yl)-4,4,5,5-tetramethyl-1,3,2-dioxaborolane

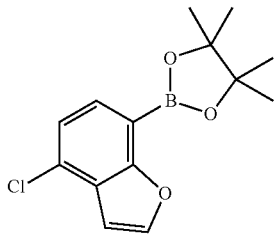 [SMILES: CC1(C)OB(c2ccc(Cl)c3ccoc23)OC1(C)C]

2-(4-Chlorobenzofuran-7-yl)-4,4,5,5-tetramethyl-1,3,2-dioxaborolane was prepared as described in Preparation 98 from 7-bromo-4-chlorobenzofuran: $^1$H NMR (400 MHz, CDCl$_3$) δ 7.75 (d, J=2.2 Hz, 1H), 7.67 (d, J=7.8 Hz, 1H), 7.24 (d, J=7.8 Hz, 1H), 6.86 (d, J=2.2 Hz, 1H), 1.41 (s, 12H); ESIMS m/z 278 ([M+H]$^+$).

Preparation 38: 2-(5-Fluorobenzofuran-6-yl)-4,4,5,5-tetramethyl-1,3,2-dioxaborolane

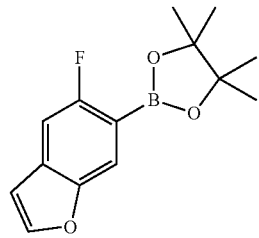 [SMILES: CC1(C)OB(c2cc3occc3cc2F)OC1(C)C]

2-(5-Fluorobenzofuran-6-yl)-4,4,5,5-tetramethyl-1,3,2-dioxaborolane was prepared as described in Preparation 98 from 6-bromo-5-fluorobenzofuran: $^1$H NMR (400 MHz, CDCl$_3$) δ 7.85 (d, J=4.3 Hz, 1H), 7.68 (d, J=2.2 Hz, 1H), 7.24-7.20 (m, 1H), 6.75-6.70 (m, 1H), 1.38 (s, 12H); $^{19}$F NMR (376 MHz, CDCl$_3$) δ −110.23 (dd, J=9.6, 4.1 Hz); ESIMS m/z 262 ([M+H]$^+$).

Preparation 39: 2-(7-Fluorobenzofuran-6-yl)-4,4,5,5-tetramethyl-1,3,2-dioxaborolane

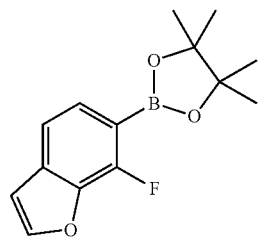 [SMILES: CC1(C)OB(c2ccc3ccoc3c2F)OC1(C)C]

2-(7-Fluorobenzofuran-6-yl)-4,4,5,5-tetramethyl-1,3,2-dioxaborolane was prepared as described in Preparation 98 from 6-bromo-7-fluorobenzofuran. $^1$H NMR (400 MHz, CDCl$_3$) δ 7.68 (t, J=3.1 Hz, 1H), 7.55 (dd, J=7.8, 4.5 Hz, 1H), 7.34 (t, J=6.5 Hz, 1H), 6.80 (dd, J=2.9, 2.2 Hz, 1H), 1.38 (s, 12H); $^{19}$F NMR (376 MHz, CDCl$_3$) δ −127.62 (dd, J=4.2, 3.1 Hz); ESIMS m/z 262 ([M+H]$^+$).

Preparation 40: 2-(6-Fluorobenzo[b]thiophen-5-yl)-4,4,5,5-tetramethyl-1,3,2-dioxaborolane and 2-(4-fluorobenzo[b]thiophen-5-yl)-4,4,5,5-tetramethyl-1,3,2-dioxaborolane

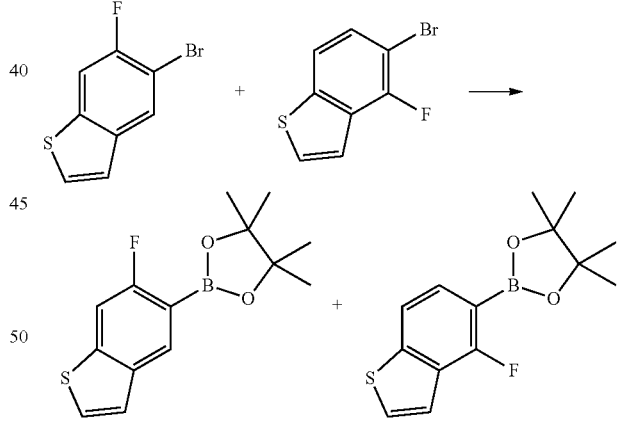

2-(6-Fluorobenzo[b]thiophen-5-yl)-4,4,5,5-tetramethyl-1,3,2-dioxaborolane and 2-(4-fluorobenzo[b]thiophen-5-yl)-4,4,5,5-tetramethyl-1,3,2-dioxaborolane were prepared as described in Preparation 98 from 5-bromo-4-fluorobenzo[b]thiophene and 5-bromo-6-fluorobenzo[b]thiophene: $^1$H NMR (400 MHz, CDCl$_3$) δ 8.20 (d, J=5.5 Hz, 1H), 7.53 (d, J=9.3 Hz, 1H), 7.35 (d, J=5.5 Hz, 1H), 7.30 (d, J=5.5 Hz, 1H), 1.39 (s, 12H); $^1$H NMR (400 MHz, CDCl$_3$) δ 7.69-7.61 (m, 2H), 7.47 (d, J=5.6 Hz, 1H), 7.39 (d, J=5.6 Hz, 1H), 1.39 (s, 12H); $^{19}$F NMR (376 MHz, CDCl$_3$) δ −107.24, −109.56; ESIMS m/z 278 ([M+H]$^+$).

Preparation 41: 2-(5-Fluorobenzo[b]thiophen-6-yl)-4,4,5,5-tetramethyl-1,3,2-dioxaborolane and 2-(5-fluorobenzo[b]thiophen-4-yl)-4,4,5,5-tetramethyl-1,3,2-dioxaborolane

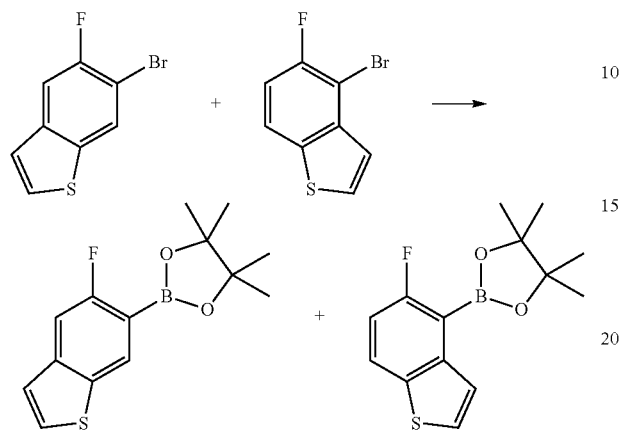

2-(5-Fluorobenzo[b]thiophen-6-yl)-4,4,5,5-tetramethyl-1,3,2-dioxaborolane and 2-(5-fluorobenzo[b]thiophen-4-yl)-4,4,5,5-tetramethyl-1,3,2-dioxaborolane were prepared as described in Preparation 98 from 6-bromo-5-fluorobenzo[b]thiophene and 4-bromo-5-fluorobenzo[b]thiophene: $^1$H NMR (400 MHz, CDCl$_3$) δ 8.26 (d, J=5.1 Hz, 1H), 7.59 (d, J=5.4 Hz, 1H), 7.45 (d, J=9.9 Hz, 1H), 7.28 (d, J=5.4 Hz, 1H), 1.39 (s, 12H); $^1$H NMR (400 MHz, CDCl$_3$) δ 7.92 (d, J=5.5 Hz, 1H), 7.88 (dd, J=8.8, 4.9 Hz, 1H), 7.55 (d, J=5.5 Hz, 1H), 7.07 (t, J=9.1 Hz, 1H), 1.42 (s, 12H); $^{19}$F NMR (376 MHz, CDCl$_3$) δ -107.32, -107.34, -107.35, -107.36, -111.00, -111.02, -111.02, -111.03, -111.04, -111.04; ESIMS m/z 278 ([M+H]$^+$).

Preparation 42: 2-(Benzo[b]thiophen-6-yl)-4,4,5,5-tetramethyl-1,3,2-dioxaborolane

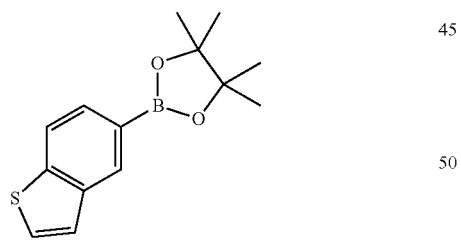

6-Bromobenzo[b]thiophene (3.09 g, 14.5 mmol), 4,4,4',4',5,5,5',5'-octamethyl-2,2'-bi(1,3,2-dioxaborolane) (4.42 g, 17.4 mmol), [1,1'-bis(diphenylphosphino)ferrocene]-palladium(II) chloride (0.54 g, 0.74 mmol), and potassium acetate (2.89 g, 29.4 mmol) in anhydrous dioxane (48 mL) was refluxed at 80° C. for 4 h. The reaction was cooled and diluted with ethyl acetate, filtered through a pad of Celite, and washed with brine. The aqueous layer was extracted with ethyl acetate. The organic layers were dried, filtered, and adsorbed onto silica gel. Purification by flash chromatography (0-30% ethyl acetate/hexanes) provided 2-(benzo[b]thiophen-6-yl)-4,4,5,5-tetramethyl-1,3,2-dioxaborolane as a yellow oily solid: (3.266 g, 87%): $^1$H NMR (400 MHz, CDCl$_3$) δ 8.38 (d, J=0.7 Hz, 1H), 7.79 (ddd, J=20.2, 8.0, 0.8 Hz, 2H), 7.51 (d, J=5.5 Hz, 1H), 7.34 (dd, J=5.4, 0.7 Hz, 1H), 1.37 (s, 12H); $^{13}$C NMR (101 MHz, CDCl$_3$) δ 141.78, 129.75, 129.58, 128.18, 123.87, 122.94, 83.89, 24.92; EIMS m/z 260.

Preparation 43: 5-Fluoro-6-(4,4,5,5-tetramethyl-1,3,2-dioxaborolan-2-yl)-1H-indole

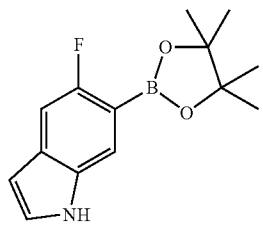 [SMILES: CC1(C)OB(c2cc3[nH]ccc3cc2F)OC1(C)C]

To a round bottom flask, 4,4,4',4',5,5,5',5'-octamethyl-2,2'-bi(1,3,2-dioxaborolane) (1.424 g, 5.61 mmol), [1,1'-bis(diphenylphosphino)ferrocene]dichloropalladium(II) (0.342 g, 0.467 mmol), and potassium acetate (0.917 g, 9.34 mmol) were charged as solids. The flask was sealed, and pumped and purged 3× with inert gas. Then 6-bromo-5-fluoro-1H-indole (1.0 g, 4.67 mmol) in dioxane (15.57 mL) was added. The reaction was stirred and warmed to an internal temperature of 85° C. After 18 h the reaction mixture was cooled and filtered through a pad of Celite, washing with excess ethyl acetate. The filtrate was diluted with water and partitioned. The aqueous layer was extracted with ethyl acetate (3×15 mL). The combined organics were dried over MgSO$_4$, filtered and concentrated in vacuo. The crude product was purified using a Teledyne ISCO purification system with a gradient eluent system of ethyl acetate and hexanes to yield the title compound as a peach-colored solid (656 mg, 54%): $^1$H NMR (400 MHz, DMSO-d$_6$) δ 1.31 (s, 12H), 6.42 (ddd, J=2.9, 1.9, 0.9 Hz, 1H), 7.22 (d, J=10.5 Hz, 1H), 7.52 (t, J=2.8 Hz, 1H), 7.69 (d, J=4.8 Hz, 1H), 11.24 (s, 1H); $^{19}$F NMR (376 MHz, DMSO-d$_6$) δ -116.07; ESIMS m/z 262.0 ([M+H]$^+$), 260.0 ([M-H]$^-$).

Preparation 44: 7-Bromo-4-chloro-1H-indole

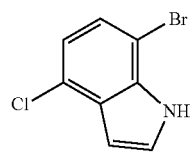 [SMILES: Clc1ccc(Br)c2[nH]ccc12]

To a solution of 1-bromo-4-chloro-2-nitrobenzene (932 mg, 3.95 mmol) in tetrahydrofuran (10 mL), vinylmagnesium bromide (0.7 M in tetrahydrofuran) (12 mmol) in tetrahydrofuran (15 mL) was added drop wise at -40° C. After 1 h the reaction mixture was poured into saturated NH$_4$Cl. The resulting organic layer was concentrated. The resulting residue was purified using a Teledyne ISCO chromatography system with a gradient eluent system of 2% ethyl acetate in hexane to yield the title compound (400 mg, 44%): $^1$H NMR (300 MHz, CDCl₃) δ 6.73 (t, J=2.8 Hz, 1H), 7.02 (d, J=8.1 Hz, 1H), 7.19-7.39 (m, 2H), 8.43 (s, 1H).

Preparation 45: 4-Bromo-7-chloro-1H-indole

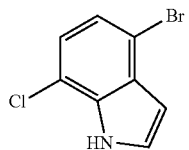 [SMILES: Clc1ccc(Br)c2cc[nH]c12]

4-Bromo-7-chloro-1H-indole was prepared from 4-bromo-1-chloro-2-nitrobenzene as described in Preparation 114: ¹H NMR (300 MHz, CDCl₃) δ 6.49-6.74 (m, 1H), 7.07 (d, J=8.1 Hz, 1H), 7.15-7.42 (m, 2H), 8.49 (s, 1H).

Preparation 46: 6-Bromo-7-fluoro-1H-indole

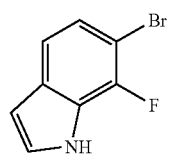 [SMILES: Fc1c(Br)ccc2cc[nH]c12]

6-Bromo-7-fluoro-1H-indole was prepared from 1-bromo-2-fluoro-3-nitrobenzene as described in Preparation 114 (250 mg, 25.2%): ¹H NMR (300 MHz, CDCl₃) δ 6.52-6.62 (m, 1H), 7.13-7.34 (m, 3H), 8.38 (s, 1H); ESIMS m/z 215.0 ([M+H]⁺).

Preparation 47 (Precursor Example 1): 4-Chloro-7-(4,4,5,5-tetramethyl-1,3,2-dioxaborolan-2-yl)-1H-indole

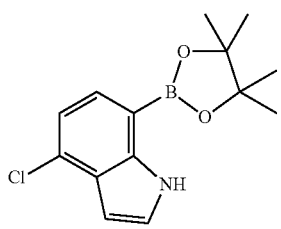 [SMILES: CC1(C)OB(c2ccc(Cl)c3cc[nH]c23)OC1(C)C]

To a solution of 7-bromo-4-chloro-1H-indole (8 g, 0.03 mol) in dioxane; KOAc (9.8 g, 0.1 mol), dichloro[1,1'-bis(diphenylphosphino)ferrocene]-palladium(II) (2.19 g, 0.003 mol), 4,4,4',4',5,5,5',5'-octamethyl-2,2'-bi(1,3,2-dioxaborolane) (13.2 g, 0.052 mol) were charged as solids. The reaction was placed under inert atmosphere and the flask was sealed. The reaction was heated to 100° C. for 16 h. The reaction was then treated with H₂O and extracted with ethyl acetate. The organic layer was partitioned and concentrated. The resulting residue was purified using a Teledyne ISCO chromatography system with a gradient eluent system of ethyl acetate in Hexane to yield the title compound (1.3 g, 15.6%): ¹H NMR (300 MHz, CDCl₃) δ 1.40 (s, 24H), 6.58-6.73 (m, 1H), 7.14 (d, J=7.6 Hz, 1H), 7.28-7.36 (m, 1H), 7.56 (d, J=7.6 Hz, 1H), 9.34 (s, 1H).

Preparation 48: 7-Chloro-4-(4,4,5,5-tetramethyl-1,3,2-dioxaborolan-2-yl)-1H-indole

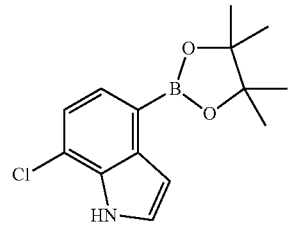 [SMILES: CC1(C)OB(c2ccc(Cl)c3[nH]ccc23)OC1(C)C]

7-Chloro-4-(4,4,5,5-tetramethyl-1,3,2-dioxaborolan-2-yl)-1H-indole was prepared as described in Preparation 117 from 4-bromo-7-chloro-1H-indole (4.2 g, 43.7%): ¹H NMR (300 MHz, CDCl₃) δ 1.38 (s, 26H), 7.08 (dd, J=3.2, 2.2 Hz, 1H), 7.20 (d, J=7.6 Hz, 1H), 7.30 (t, J=2.8 Hz, 1H), 7.56 (d, J=7.6 Hz, 1H), 8.40 (s, 1H).

Preparation 49 (Precursor Example 2): 7-Fluoro-6-(4,4,5,5-tetramethyl-1,3,2-dioxaborolan-2-yl)-1H-indole

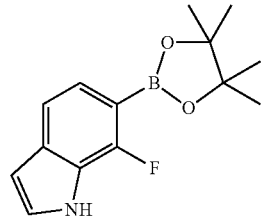 [SMILES: CC1(C)OB(c2ccc3cc[nH]c3c2F)OC1(C)C]

7-fluoro-6-(4,4,5,5-tetramethyl-1,3,2-dioxaborolan-2-yl)-1H-indole was prepared as described in Preparation 117 from 6-bromo-7-fluoro-1H-indole (150 mg, 45.5%): ¹H NMR (300 MHz, CDCl₃) δ 1.26 (s, 25H), 1.39 (s, 24H), 7.27 (d, J=4.5 Hz, 2H), 7.40 (d, J=2.6 Hz, 2H), 8.43 (s, 1H); ¹⁹F NMR (282 MHz, CDCl₃) δ −124.52; ¹³C NMR (101 MHz, CDCl₃) δ 24.87 (d, J=15.9 Hz), 77.30, 83.49 (d, J=6.9 Hz), 103.25, 115.98 (d, J=3.3 Hz), 126.08 (d, J=7.7 Hz).

Preparation 50 (Precursor Example 3): 7-Fluoro-6-(4,4,5,5-tetramethyl-1,3,2-dioxaborolan-2-yl)-1-(triisopropylsilyl)-1H-indole

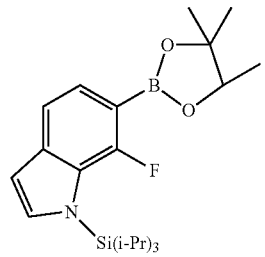

7-Fluoro-1-(triisopropylsilyl)-1H-indole (4.0 g, 14 mmol) (Prepared according to M. Schlosser, et al, *Eur. J. Org. Chem.* 2006, 2956-2969) was dissolved in 30 mL dry THF, cooled to −75° C., treated in portions with sec-butyl lithium (10 mL, 1.4 M, 14 mmol) and stirred for 2 h at −75° C. 2-Isopropoxy-4,4,5,5-tetramethyl-1,3,2-dioxaborolane (3.0 mL, 2.7 g, 14 mmol) was added in portions and the mixture was stirred for 1 h at −75° C. The cooling was removed and the temperature was allowed to rise to 5° C. over 30 min. The reaction was quenched by addition of 5 mL sat. NH$_4$Cl and partitioned between ethyl acetate and water. The organic phase was washed with sat. NaCl, dried (Na$_2$SO$_4$), evaporated onto silica gel, and purified by flash chromatography (SiO$_2$; eluting with hexanes) to give 4.2 g of the title compound as a thick oil (4.2 g, 73%): $^1$H NMR (400 MHz, CDCl3) δ 7.43 (dd, J=7.9, 4.6 Hz, 1H), 7.38 (m, 2H), 1.75 (m, 3H), 1.38 (s, 12H), 1.13 (d, J=7.6 Hz, 18H). $^{19}$F NMR (376 MHz, CDCl3) δ −113.07. EIMS m/z 417.

Preparation 51: 2-Ethynyl-4,6-difluoroaniline

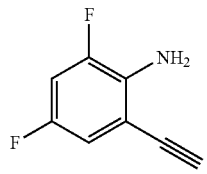

Step 1:

2-Bromo-4,6-difluoroaniline (10 g, 48 mmol), copper (I) iodide (180 mg, 0.96 mmol), bis(triphenylphosphine)palladium(II) chloride (680 mg, 0.96 mmol) and ethynyltrimethylsilane (7.1 g, 72 mmol) were combined with 10 ml dry DMF and heated to 50° C. for 18 h. An additional 2 mL ethynyltrimethylsilane, 200 mg bis(triphenylphosphine)palladium (II) chloride, and 60 mg CuI were added and heating was continued for 4 h. After cooling, the mixture was diluted with ethyl acetate and stirred with 1 N HCl. The dark mixture was filtered through Celite to remove fine solids. The organic phase was washed with water, sat. NaCl, dried and concentrated. Purification by flash chromatography (SiO$_2$, eluting with 0-20% EtOAc in hexanes) afforded 9 g of material that consisted of a 70/30 ratio of the TMS alkyne derivative and the starting bromide.

Step 2:

The mixture was carried in to the desilylation without further purification. The TMS derivative was dissolved in methanol (500 mL) and treated with 8.5 g KF. A clear solution formed which was stirred overnight at RT. Most of the volatiles were removed under vacuum, the residue was taken up in ethyl acetate and washed water and with sat. NaCl. The solution was dried, evaporated and purified by flash chromatography (SiO$_2$, eluting with 0-10% ethyl acetate in hexanes) to provide the title compound (4.2 g, 70 area % pure by FID-GC): $^1$H NMR (400 MHz, CDCl3) δ 6.83 (m, 1H), 4.13 (m, 1H), 3.46 (s, 1H). $^{19}$F NMR (376 MHz, CDCl3) δ −124.04, −124.88, −126.94, −130.08. EIMS m/z 153. This material was carried through to the cyclization step without further purification.

Preparation 52: 5,7-Difluoro-1H-indole

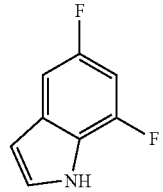 [SMILES: Fc1cc(F)c2[nH]ccc2c1]

The impure 2-ethynyl-4,6-difluoroaniline (4.2 g, 19 mmol) from the previous example was dissolved in ethanol (75 mL), treated with sodium gold(III) chloride dihydrate (310 mg, 0.77 mmol) and stirred for 3 h under an atmosphere of nitrogen. The mixture was concentrated, taken up in ethyl acetate, washed with water, washed with sat. NaCl, dried over sodium sulfate (Na$_2$SO$_4$) and evaporated. Purification by flash chromatography (SiO$_2$, 100-200 mesh; eluting with 0-15% EtOAc in hexanes containing 2% acetic acid) provided of the title product (2.0 g, ca 85% purity): $^1$H NMR (400 MHz, CDCl3) δ 8.32 (s, 1H), 7.26 (dd, J=4.8, 2.0 Hz, 1H), 7.09 (dd, J=9.1, 2.2 Hz, 1H), 6.74 (ddd, J=11.2, 9.3, 2.0 Hz, 1H), 6.55 (td, J=3.3, 2.2 Hz, 1H). $^{19}$F NMR (376 MHz, CDCl3) δ −122.11, −131.96. EIMS m/z 153.

Preparation 53: 5,7-Difluoro-1-(triisopropylsilyl)-1H-indole

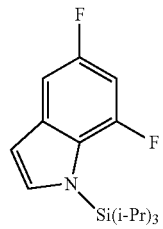

N-butyl lithium (2.7 ml, 2.5 M, 6.9 mmol) was added to 10 mL dry THF at −70° C. 5,7-difluoro-1H-indole (1.0 g, 6.5 mmol) in 5 mL THF was added in portions to the this solution and the mixture was stirred for 30 min at −75° C. Triisopropylchlorosilane (1.5 mL, 1.3 g, 6.9 mmol) was added, stirring was continued for 1 h at −75° C. and then the mixture was allowed to warm to −5° C. over 2 h. After treatment with 5 mL sat. NH$_4$Cl, the mixture was mixed with 30 mL ether and the organic phase was washed with 5 mL sat. NaCl, dried (Na$_2$SO$_4$) and evaporated. The product was purified by flash chromatography (SiO$_2$; hexanes) to provide the title compound as a clear oil (1.5 g; 74%): $^1$H NMR (400 MHz, CDCl3) δ 7.35 (d, J=3.1 Hz, 1H), 7.07 (dd, J=8.7, 2.3 Hz, 1H), 6.69 (m, 1H), 6.59 (t, J=3.1 Hz, 1H), 1.67 (m, 3H), 1.13 (d, J=7.6 Hz, 18H). 19F NMR (376 MHz, CDCl3) δ −120.64, −120.65, −122.49, −122.49. EIMS m/z 309.

Preparation 54: 5,7-Difluoro-6-iodo-1-(triisopropyl-silyl)-1H-indole

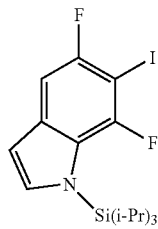

5,7-difluoro-1-(triisopropylsilyl)-1H-indole (1.4 g, 4.5 mmol) and pentamethyldiethylene-triamine (830 mg, 4.8 mmol) were combined in 10 mL dry THF, cooled to −70° C. and treated in portions with sec-butyl lithium (3.4 mL, 1.4 M, 4.8 mmol) and stirred for 3 h at this temperature. Iodine (1.3 g, 5.0 mmol) in 5 mL THF was added, the mixture was stirred for 50 min, quenched by addition of 3 mL sat. NH$_4$Cl and partitioned between diethyl ether and water. The organic phase was washed with sat. NaCl, dried (Na$_2$SO$_4$), evaporated and purified by flash chromatography (SiO$_2$; hexanes) the title compound as a clear oil which solidified on standing (1.9 g, 90%). $^1$H NMR (400 MHz, CDCl3) δ 7.34 (d, J=3.1 Hz, 1H), 7.14 (dd, J=7.7, 0.9 Hz, 1H), 6.60 (t, J=3.1 Hz, 1H), 1.67 (m, 3H), 1.13 (d, J=7.6 Hz, 18H). $^{19}$F NMR (376 MHz, CDCl3) δ −101.37, −105.33. MP: 74-76° C.

Examples of Synthesis of Compounds of Formula (I)

Example 1

Methyl 4-amino-3-chloro-5-fluoro-6-(7-fluoro-1H-indol-6-yl)picolinate (Compound No. 1.14)

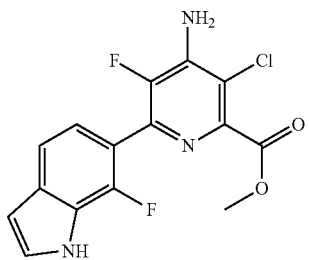 [SMILES: COC(=O)c1nc(-c2ccc3cc[nH]c3c2F)c(F)c(N)c1Cl]

Methyl 4-amino-3,6-dichloro-5-fluoropicolinate (0.650 g, 2.72 mmol), 7-fluoro-6-(4,4,5,5-tetramethyl-1,3,2-dioxaborolan-2-yl)-1H-indole (0.817 g, 3.13 mmol), bis(triphenylphosphine)palladium(II) chloride (0.191 g, 0.272 mmol), and cesium fluoride (0.826 g, 5.44 mmol, Note: potassium fluoride replaced cesium fluoride in some examples that refer to this particular example) were combined in acetonitrile (4.53 mL) and water (4.53 mL). The reaction mixture was irradiated in a Biotage Initiator microwave at 110° C. in a sealed vial for 30 min. The cooled reaction mixture was partitioned between ethyl acetate and water. The organic phase was dried and concentrated. The product was purified by flash chromatography (SiO$_2$; eluting with 5-40% ethyl acetate in hexanes) to provide the title compound as an white solid (0.517 g, 52.4% yield).

The preparation method used in this example is referred to in Table 11 as "Coupling 1."

Example 2

Methyl 4-amino-3-chloro-5-fluoro-6-(1H-indol-5-yl)picolinate (Compound No. 1.2)

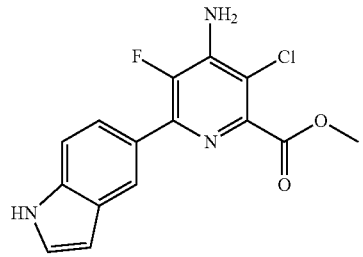 [SMILES: COC(=O)c1nc(-c2ccc3[nH]ccc3c2)c(F)c(N)c1Cl]

1H-Indol-5-ylboronic acid (220 mg, 1.4 mmol, 1.1 equiv) and methyl 4-amino-3,6-dichloro-5-fluoropicolinate (300 mg, 1.3 mmol, 1.0 equiv) were sequentially added to a 5 mL Biotage microwave vessel, followed by cesium fluoride (380 mg, 2.5 mmol, 2.0 equiv), palladium(II) acetate (14 mg, 0.063 mmol, 0.05 equiv), and sodium 3,3',3"-phosphinetriyltribenzenesulfonate (71 mg, 0.13 mmol, 0.10 equiv). A 3:1 mixture of water:acetonitrile (2.5 mL) was added and the resulting dark brown mixture was placed in a Biotage microwave and heated to 150° C. for 5 m, with external IR-sensor temperature monitoring from the side of the vessel. The cooled reaction mixture was diluted with water (50 mL) and extracted with dichloromethane (15×30 mL). The combined organic layers were dried (sodium sulfate), gravity filtered, and concentrated by rotary evaporation. The residue was purified by reverse phase column chromatography (5% acetonitrile to 100% acetonitrile gradient) to yield the title compound as a tan powder (290 mg, 73%).

The preparation method used in this example is referred to in Table 11 as "Coupling 2."

Example 3

Methyl 4-amino-6-(benzo[d]thiazol-5-yl)-3-chloro-5-fluoropicolinate (Compound No. 6.1)

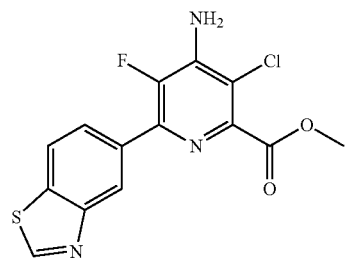 [SMILES: COC(=O)c1nc(-c2ccc3scnc3c2)c(F)c(N)c1Cl]

To a 5 mL microwave vial was added methyl 4-amino-6-bromo-3-chloro-5-fluoropicolinate (200 mg, 1.0 mmol), benzo[d]thiazol-5-ylboronic acid (237 mg, 1.35 mmol), potassium fluoride (KF; 122 mg, 2.12 mmol), TPPTS-Na (tris-(3-sulfornatophenyl)-phosphine4-hydrate sodium salt, 67 mg, 0.106 mmol) and Pd(OAc)$_2$ (11 mg, 0.053 mmol). Subsequently, CH$_3$CN (1.0 mL) and H$_2$O (3.0 mL) were added, and the reaction vial was sealed and heated in a Biotage microwave at 150° C. for 5 min, with external IR-sensor temperature monitoring from the side of the vessel. The reaction mixture was cooled to room temperature and diluted with dicloromethane, and washed wth water. The organic extracts were combined, dried (Na₂SO₄), filtered, and concentrated in vacuo. The crude product was purified by triturating with Et₂O to yield the title compound as a brown solid (172 mg, 51%).

The preparation method used in this example is referred to in Table 11 as "Coupling 3."

Example 4

Methyl 4-amino-6-(benzo[b]thiophenyl-5-yl)-3,5-dichloropicolinate (Compound No. 3.1)

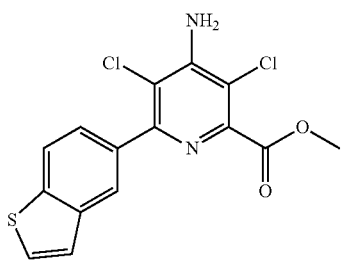 [SMILES: COC(=O)c1nc(-c2ccc3sccc3c2)c(Cl)c(N)c1Cl]

To a 5 mL microwave vial was added methyl 4-amino-3,5,6-trichloropicolinate (0.232 g, 0.909 mmol), 2-(benzo[b]thiophen-5-yl)-4,4,5,5-tetramethyl-1,3,2-dioxaborolane (0.260 g, 0.999 mmol), cesium fluoride (0.276 g, 1.817 mmol) and (PPh₃)₂PdCl₂ (0.064 g, 0.091 mmol). The reaction vial was then sealed and placed under inert atmosphere. Subsequently, Dioxane (4.0 mL) and H₂O (1.0 mL) were added and the reaction mixture was heated in a Biotage microwave at 120° C. for 60 min, with external IR-sensor temperature monitoring from the side of the vessel. The reaction mixture was cooled to room temperature and diluted with ethyl acetate (5 mL) and poured into brine solution. The layers were separated and the aqueous phase was extracted with ethyl acetate (3×10 mL). The organic extracts were combined, dried (MgSO₄), filtered, and concentrated in vacuo. The crude product was purified using a Teledyne ISCO purification system with a gradient eluent system of ethyl acetate and hexanes. Further purification was performed, as needed, using a Teledyne ISCO reverse phase system with a gradient eluent system of acetonitrile and H₂O to yield the title compound as a white solid.

The preparation method used in this example is referred to in Table 11 as "Coupling 4."

Example 5

Methyl 4-amino-3-chloro-6-(7-chlorobenzofuran-4-yl)-5-fluoropicolinate (Compound No. 2.16)

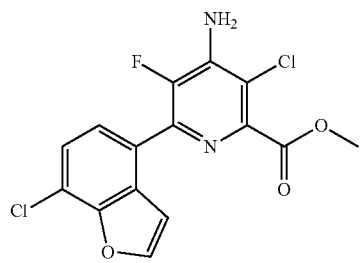 [SMILES: COC(=O)c1nc(-c2ccc(Cl)c3occc23)c(F)c(N)c1Cl]

Combined potassium fluoride (0.365 g, 6.28 mmol), diacetoxypalladium (0.047 g, 0.209 mmol), and 2-(7-chlorobenzofuran-4-yl)-5,5-dimethyl-1,3,2-dioxaborinane (0.609 g, 2.301 mmol), sodium 3,3',3''-phosphinetriyltribenzenesulfonate tetrahydrate (0.134 g, 0.209 mmol), methyl 4-amino-3,6-dichloro-5-fluoropicolinate (0.5 g, 2.092 mmol). Added water (3 mL) and acetonitrile (1 mL). Heated reaction mixture at 150° C. in a microwave reactor for 6 minutes. Diluted cooled reaction mixture with ethyl acetate and water and filtered through cotton plug. Dried organic phase (Na₂SO₄) and concentrated under vacuum. Purified by reverse phase chromatography to provide the title compound as a white solid (127 mg, 12.5% yield).

The preparation method used in this example is referred to in Table 11 as "Coupling 5."

Example 6

Methyl 4-amino-3-chloro-6-(7-fluoro-1H-indol-6-yl)picolinate (Compound No. 1.22)

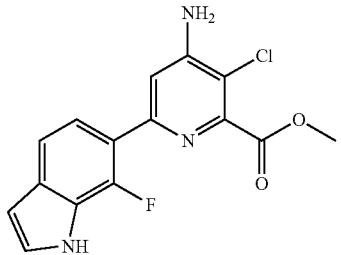 [SMILES: COC(=O)c1nc(-c2ccc3cc[nH]c3c2F)cc(N)c1Cl]

Methyl 4-acetamido-3,6-dichloropicolinate (400 mg, 1.520 mmol), 7-fluoro-6-(4,4,5,5-tetramethyl-1,3,2-dioxaborolan-2-yl)-1H-indole (437 mg, 1.673 mmol), cesium fluoride (462 mg, 3.04 mmol), and (PPh₃)₂PdCl₂ (107 mg, 0.152 mmol) were charged as solids into a microwave reaction vessel and dioxane (4 mL) and water (1 mL) were added. The reaction vessel sealed and irradiated in a Biotage Initiator microwave at 110° C. for 2 h, with external IR-sensor temperature monitoring from the side. The reaction mixture was partitioned between ethyl acetate and water. The organic phase was filtered and concentrated. The intermediate product was purified by flash chromatography (ISCO 40 g silica 10-75% EtOAc: Hex 16 CV). Fractions containing product were combined and concentrated to give 524 mg of a white solid intermediate methyl 4-acetamido-3-chloro-6-(7-fluoro-1H-indol-6-yl)picolinate (0.524 g, 1.448 mmol) which was subsequently diluted with methanol (10.0 mL). Then acetyl chloride (0.725 mL, 10.20 mmol) was added. The reaction mixture was allowed to stir at room temperature for 18 h. The reaction was concentrated to dryness. The resulting residue was dissolved in ethyl acetate and poured into saturated NaHCO₃ solution. The layers were partitioned and the aqueous layer was extracted with ethyl acetate (3×15 mL). The organic extracts were combined, washed with saturated NaCl solution, dried (MgSO₄), filtered and concentrated in vacuo. The crude product was purified using a Teledyne ISCO purification system with a gradient eluent system of ethyl acetate and hexanes to yield the title compound as a white solid (365 mg, 79%).

The preparation method used in this example is referred to in Table 11 as "Coupling 6."

Example 7

Methyl 4-amino-3-chloro-6-(5,7-difluoro-1H-indol-6-yl)picolinate (Compound No. 1.26)

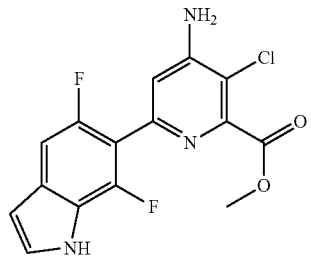 [SMILES: COC(=O)c1nc(-c2c(F)cc3cc[nH]c3c2F)cc(N)c1Cl]

5,7-difluoro-6-iodo-1-(triisopropylsilyl)-1H-indole (450 mg, 1.0 mmol), methyl 4-acetamido-3-chloro-6-(trimethylstannyl)picolinate (450 mg, 1.1 mmol) were combined in 7 mL dry DMF, deaerated with a stream of nitrogen for 15 min, treated with bis(triphenylphosphine)palladium(II) chloride (72 mg, 0.10 mmol) and copper (I) iodide and heated to 60° C. for 2 h. The mixture was partitioned between ethyl acetate and water. The organic phase was washed with water, washed with sat. NaCl, dried ($Na_2SO_4$), and evaporated. Purification by flash chromatography ($SiO_2$, 100-200 mesh; eluting with 0-30% EtOAc in hexanes) provide 200 mg of the silylated N-acetamide product. This material was slurried in methanol (15 mL), treated with 2 mL acetyl chloride and heated at reflux for 2 h. The volatiles were removed under vacuum and the residue was purified by flash chromatography ($SiO_2$; 0-40% ethyl acetate in hexanes) to provide 30 mg of the title compound plus 60 mg of title compound that was still protected by the TIPS group on the indole nitrogen. The TIPS derivative was dissolved in 5 mL dry THF, treated with tetrabutylammonium fluoride hydrate (140 mg, 0.5 mmol) and stirred for 1 h at 20° C. The mixture was partitioned between 20 ml ethyl acetate and sat. NaCl. The organic phase was dried ($Na_2SO_4$) and evaporated. Purification by flash chromatography ($SiO_2$; 0-50% ethyl acetate in hexanes) provide another 30 mg of the title compound as a white solid (60 mg, 16%).

The preparation method used in this example is referred to in Table 11 as "Coupling 7."

Example 8

Methyl 4-amino-3-chloro-5-fluoro-6-(7-fluoro-1H-indol-6-yl)picolinate (Compound No. 1.14)

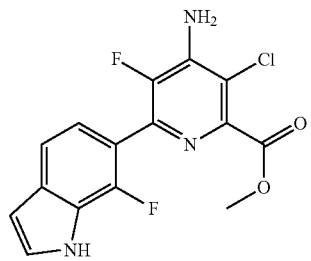 [SMILES: COC(=O)c1nc(-c2ccc3cc[nH]c3c2F)c(F)c(N)c1Cl]

7-fluoro-6-(4,4,5,5-tetramethyl-1,3,2-dioxaborolan-2-yl)-1-(triisopropylsilyl)-1H-indole (500 mg, 1.2 mmol), methyl 4-amino-3,6-dichloro-5-fluoropicolinate (290 mg, 1.2 mmol), cesium fluoride (360 mg, 2.4 mmol) and bis(triphenylphosphine)palladium(II) chloride (84 mg, 0.12 mmol) were combined in 4 mL of a 1:1 v/v acetonitrile-water and heated at 115° C. for 25 min in a Biotage Initiator microwave reactor. The mixture was partitoned between ethyl acetate and sat. NaCl and the organic phase was dried and evaporated. Purification by flash chromatography ($SiO_2$; eluting with 0-20% ethyl acetate in dichloromethane) provided impure product. The material was purified by flash chromatography again ($SiO_2$; eluting with 0-30% ethyl acetate in hexanes) to provide the title compound as a white solid (220 mg, 52%).

The preparation method used in this example is referred to in Table 11 as "Coupling 8."

Example 9

Methyl 4-amino-5-fluoro-6-(7-fluoro-1H-indol-6-yl)-3-vinylpicolinate (Compound No. 1.17)

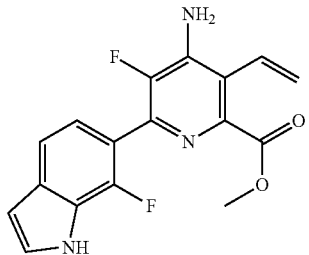 [SMILES: C=Cc1c(C(=O)OC)nc(-c2ccc3cc[nH]c3c2F)c(F)c1N]

7-Fluoro-6-(4,4,5,5-tetramethyl-1,3,2-dioxaborolan-2-yl)-1-(triisopropylsilyl)-1H-indole (320 mg, 0.77 mmol), methyl 4-amino-6-chloro-5-fluoro-3-vinylpicolinate (190 mg, 0.84 mmol), sodium carbonate (81 mg, 0.77 mmol) and bis(triphenylphosphine)palladium(II) chloride (54 mg, 0.08 mmol) were combined in 4 mL of a 1:1 v/v acetonitrile-water and heated to 115° C. for 30 min in a Biotage Initiator microwave reactor. The mixture was partitioned between ethyl acetate and water. The organic phase was washed with sat. NaCl, dried ($Na_2SO_4$), and evaporated. Purification by flash chromatography ($SiO_2$; eluting with 0-20% ethyl acetate in hexanes) provided 220 mg of the TIPS protected product. This material was dissolved in 10 mL THF, treated with tetrabutylammonium fluoride hydrate (260 mg, 1.0 mmol) and stirred for 1 h. The mixture was partitioned between sat. NaCl and ethyl acetate. The organic phase was washed with sat. NaCl, dried ($Na_2SO_4$), and evaporated. Purification by flash chromatography ($SiO_2$; eluting with 0-20% ethyl acetate in hexanes) provided to give 100 mg of the title compound as a white solid (100 mg, 37%).

The preparation method used in this example is referred to in Table 11 as "Coupling 9."

Example 10

Preparation of methyl 4-amino-3-chloro-5-fluoro-6-(7-fluoro-1-(triisopropylsilyl)-1H-indol-6-yl)picolinate (Compound 1.12)

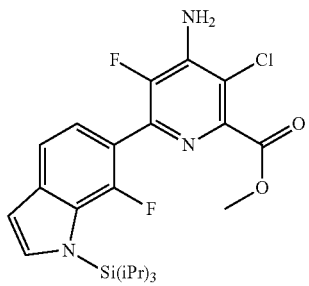

7-Fluoro-6-(4,4,5,5-tetramethyl-1,3,2-dioxaborolan-2-yl)-1-(triisopropylsilyl)-1H-indole (1.0 g, 2.4 mmol), methyl 4-amino-3,6-dichloro-5-fluoropicolinate (630 mg, 2.6 mmol), sodium carbonate (250 mg, 2.4 mmol) and with bis(triphenylphosphine)palladium(II) chloride (170 mg, 0.24 mmol) were combined in 10 mL of 1:1 v/v acetonitrile-water and heated at 110° C. for 30 min in a Biotage Initiator microwave reactor. The mixture was stirred with 30 mL ethyl acetate and 20 mL water and filtered through glass wool to remove dark solids. The organic phase was washed with sat. NaCl, dried (Na$_2$SO$_4$), and evaporated. Purification by flash chromatography (SiO$_2$; eluting with 0-30% ethyl acetate in hexanes) provided 520 mg of the title compound as a white solid (520 mg; 42).

The preparation method used in this example is referred to in Table 11 as "Coupling 10."

Example 11

Methyl 4-amino-6-(3-bromobenzo[b]thiophen-7-yl)-3-chloro-5-fluoropicolinate (Compound No. 3.26)

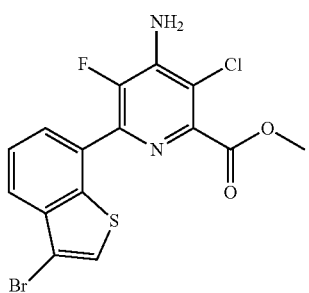 [SMILES: COC(=O)c1nc(-c2cccc3c(Br)csc23)c(F)c(N)c1Cl]

Methyl 4-amino-6-(benzo[b]thiophen-7-yl)-3-chloro-5-fluoropicolinate (0.500 g, 1.485 mmol) was dissolved in dichloromethane (9.90 mL) and cooled to −5° C. in a acetone bath to which was added a few pieces of dry ice. Bromine (114 mL, 2.227 mmol) was dissolved in dichloromethane (9.90 mL) and added dropwise. The reaction mixture was stirred overnight, and then partitioned between ethyl acetate and water. The organic phase was dried and concentrated and the product purified by flash chromatography (SiO$_2$, 5-40% ethyl acetate/hexane gradient) followed by a second purification by reverse phase chromatography to provide the title compound as a grey solid (0.278 g, 45).

Example 12

4-Amino-3-chloro-5-fluoro-6-(7-fluoro-1H-indol-6-yl)picolinic acid (Compound 1.38)

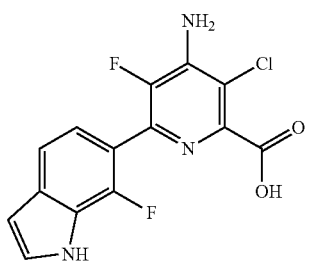 [SMILES: Nc1c(F)c(-c2ccc3cc[nH]c3c2F)nc(C(=O)O)c1Cl]

To a reaction vessel containing methyl 4-amino-3-chloro-5-fluoro-6-(7-fluoro-1H-indol-6-yl)picolinate (0.500 g, 1.481 mmol) was added methanol (14.81 ml) and sodium hydroxide (2.96 ml, 5.92 mmol). The reaction mixture was stirred overnight at rt then acidified by adding a slight excess of 2N HCl. The mixture was concentrated and the precipitate that formed was washed with water and dried under vacuum to provide 4-amino-3-chloro-5-fluoro-6-(7-fluoro-1H-indol-6-yl)picolinic acid (0.400 g, 1.174 mmol, 79% yield) as an off-white solid:

The preparation method used in this example is referred to in Table 11 as "Hydrolysis 1."

Example 13

4-Amino-6-(benzo[b]thiophen-5-yl)-3,5-dichloropicolinic acid (Compound 3.2)

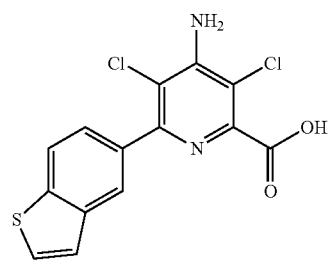 [SMILES: Nc1c(Cl)c(C(=O)O)nc(-c2ccc3sccc3c2)c1Cl]

In a 100 mL round bottom flask, methyl 4-amino-6-(benzo[b]thiophen-5-yl)-3,5-dichloropicolinate (210 mg, 0.595 mmol) was dissolved in methanol (2.3 mL), tetrahydrofuran (2.3 mL), and H$_2$O (1.2 mL). Lithium hydroxide hydrate (74.8 mg, 1.784 mmol) was added as a solid. The reaction was stirred at room temperature until complete. The reaction mixture was concentrated to dryness. The resulting residue was dissolved in H$_2$O (2.0 mL) and 1 N HCl was used to adjust the pH to 3.0, causing a precipitate to form. This suspension was extracted with ethyl acetate (3×15 mL). The organic extracts were combined, washed with Saturated NaCl solution, dried (MgSO$_4$), filtered and concentrated. Additional purification of the resulting solid was performed, as needed, using a Teledyne ISCO reverse phase system with a gradient eluent system of acetonitrile and H$_2$O to yield the title compound as a white solid (110 mg, 55.

The preparation method used in this example is referred to in Table 11 as "Hydrolysis 2."

TABLE 10

Compound Number, Structure, Appearance, and Preparation Method

| Compound Number | Structure | Appearance | Preparation Method: | Precursor(s) |
|---|---|---|---|---|
| 1.01 | 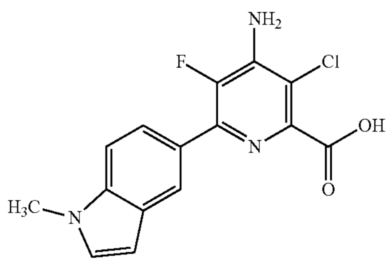 [SMILES: Cn1ccc2cc(-c3nc(C(=O)O)c(Cl)c(N)c3F)ccc21] | White Powder | Hydrolysis 1 | Compound 1.03 |
| 1.02 | 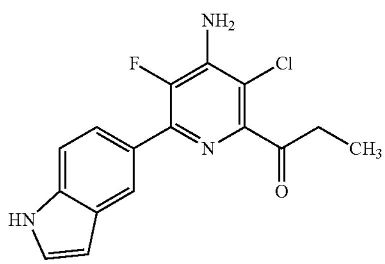 [SMILES: CCC(=O)c1nc(-c2ccc3[nH]ccc3c2)c(F)c(N)c1Cl] | Tan Powder | Coupling 2 | As described |
| 1.03 | 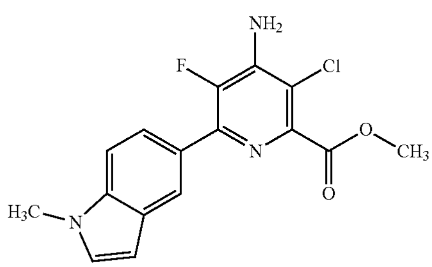 | White Powder | Coupling 2 | Head B; 1-Methyl-1H-indol-5-ylboronic acid |
| 1.04 | 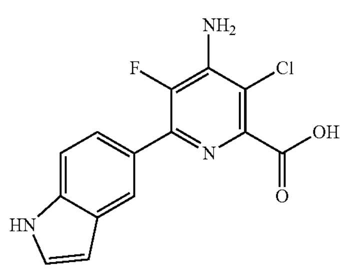 [SMILES: Nc1c(F)c(-c2ccc3[nH]ccc3c2)nc(C(=O)O)c1Cl] | Tan Powder | Hydrolysis 1 | Compound 1.02 |
| 1.05 | 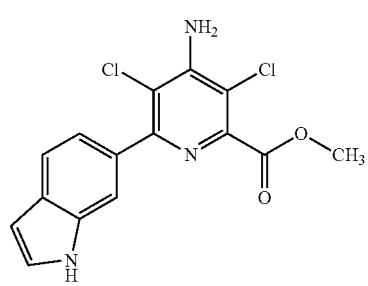 [SMILES: COC(=O)c1nc(-c2ccc3cc[nH]c3c2)c(Cl)c(N)c1Cl] | Yellow Solid | Coupling 1 | Head H; (1H-indol-6-yl)boronic acid |

TABLE 10-continued

Compound Number, Structure, Appearance, and Preparation Method

| Compound Number | Structure | Appearance | Preparation Method: | Precursor(s) |
|---|---|---|---|---|
| 1.06 | 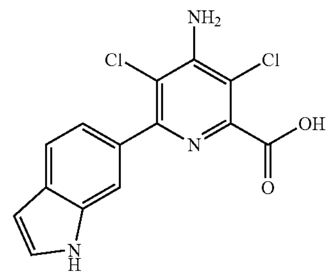 [SMILES: Nc1c(Cl)c(C(=O)O)nc(-c2ccc3cc[nH]c3c2)c1Cl] | Yellow Solid | Hydrolysis 1 | Compound 1.05 |
| 1.07 | 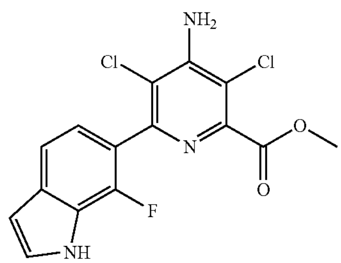 [SMILES: COC(=O)c1nc(-c2ccc3cc[nH]c3c2F)c(Cl)c(N)c1Cl] | White solid | Coupling 9 | Head H |
| 1.08 | 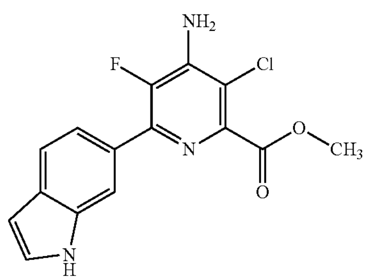 [SMILES: COC(=O)c1nc(-c2ccc3cc[nH]c3c2)c(F)c(N)c1Cl] | Off-White Foam | Coupling 2 | Head B; 1H-Indol-6-ylboronic acid |
| 1.09 | 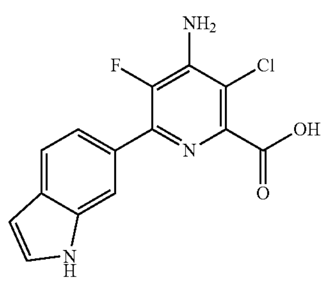 [SMILES: Nc1c(F)c(-c2ccc3cc[nH]c3c2)nc(C(=O)O)c1Cl] | White Powder | Hydrolysis 1 | Compound 1.08 |
| 1.10 | 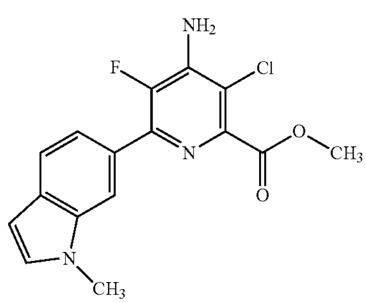 [SMILES: COC(=O)c1nc(-c2ccc3ccn(C)c3c2)c(F)c(N)c1Cl] | Tan Powder | Coupling 2 | Head B; 1-Methyl-6-(4,4,5,5-tetramethyl-1,3,2-dioxaborolan-2-yl)-1H-indole |

TABLE 10-continued

Compound Number, Structure, Appearance, and Preparation Method

| Compound Number | Structure | Appearance | Preparation Method: | Precursor(s) |
|---|---|---|---|---|
| 1.11 | 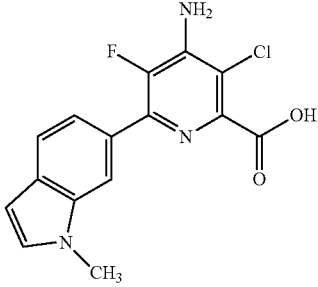 [SMILES: Cn1ccc2ccc(-c3nc(C(=O)O)c(Cl)c(N)c3F)cc21] | Pale Yellow Powder | Hydrolysis 1 | Compound 1.10 |
| 1.12 | 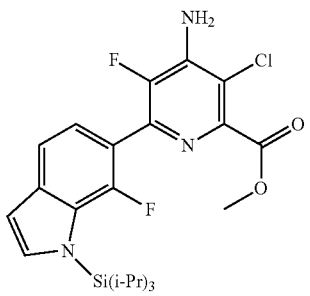 | White solid | Coupling 10 | Head B |
| 1.13 | 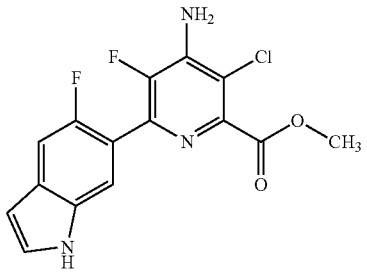 [SMILES: COC(=O)c1nc(-c2cc3[nH]ccc3cc2F)c(F)c(N)c1Cl] | Off White Solid | Coupling 4 | Head B; 5-fluoro-6-(4,4,5,5-tetramethyl-1,3,2-dioxaborolan-2-yl)-1H-indole |
| 1.14 | 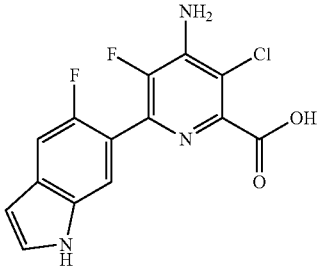 [SMILES: Nc1c(F)c(-c2cc3[nH]ccc3cc2F)nc(C(=O)O)c1Cl] | Tan Solid | Hydrolysis 2 | Compound 1.13 |
| 1.15 | 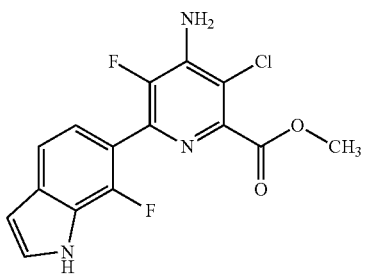 [SMILES: COC(=O)c1nc(-c2ccc3cc[nH]c3c2F)c(F)c(N)c1Cl] | White Solid | Coupling 4 | Head B; 7-fluoro-6-(4,4,5,5-tetramethyl-1,3,2-dioxaborolan-2-yl)-1H-indole |

TABLE 10-continued

Compound Number, Structure, Appearance, and Preparation Method

| Compound Number | Structure | Appearance | Preparation Method: | Precursor(s) |
|---|---|---|---|---|
| 1.16 | 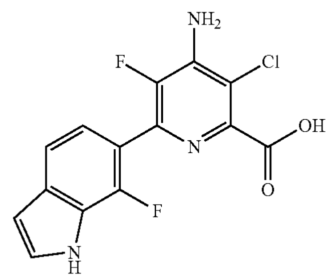 [SMILES: Nc1c(F)c(-c2ccc3cc[nH]c3c2F)nc(C(=O)O)c1Cl] | Tan Solid | Hydrolysis 2 | Compound 1.15 |
| 1.17 | 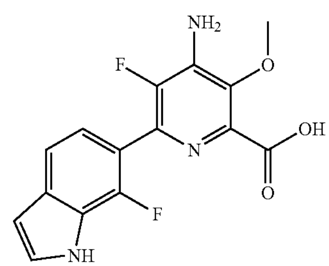 [SMILES: COc1c(C(=O)O)nc(-c2ccc3cc[nH]c3c2F)c(F)c1N] | White solid | Hydrolysis 1 | Compound 1.20 |
| 1.18 | 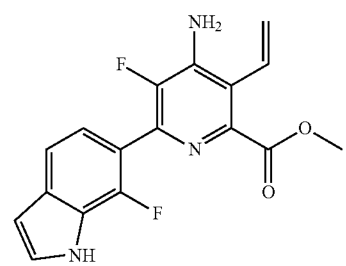 [SMILES: C=Cc1c(C(=O)OC)nc(-c2ccc3cc[nH]c3c2F)c(F)c1N] | White solid | Coupling 9 | Head G |
| 1.19 | 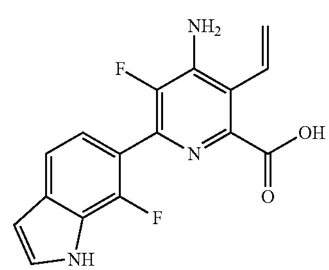 [SMILES: C=Cc1c(C(=O)O)nc(-c2ccc3cc[nH]c3c2F)c(F)c1N] | Tan solid | Hydrolysis 1 | Compound 1.18 |
| 1.20 | 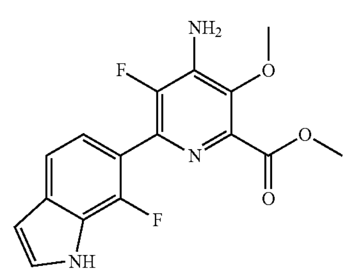 [SMILES: COC(=O)c1nc(-c2ccc3cc[nH]c3c2F)c(F)c(N)c1OC] | White solid | Coupling 8 | Head F |

TABLE 10-continued

Compound Number, Structure, Appearance, and Preparation Method

| Compound Number | Structure | Appearance | Preparation Method: | Precursor(s) |
|---|---|---|---|---|
| 1.21 | [4-amino-3-chloro-6-(1H-indol-6-yl)pyridine-2-carboxylic acid methyl ester] | White Solid | Coupling 1 | Head A, (1H-indol-6-yl)boronic acid |
| 1.22 | [4-amino-3-chloro-6-(1H-indol-6-yl)pyridine-2-carboxylic acid] | Orange Solid | Hydrolysis 1 | Compound 1.21 |
| 1.23 | [4-amino-3-chloro-6-(7-fluoro-1H-indol-6-yl)pyridine-2-carboxylic acid methyl ester] | White Solid | Coupling 6 | As described |
| 1.24 | [4-amino-3-chloro-6-(7-fluoro-1H-indol-6-yl)pyridine-2-carboxylic acid] | Yellow Solid | Hydrolysis 2 | Compound 1.23 |
| 1.25 | [4-amino-3-chloro-6-(5-fluoro-1H-indol-6-yl)pyridine-2-carboxylic acid methyl ester] | White Solid | Coupling 6 | Head L; 5-fluoro-6-(4,4,5,5-tetramethyl-1,3,2-dioxaborolan-2-yl)-1H-indole |

TABLE 10-continued

Compound Number, Structure, Appearance, and Preparation Method

| Compound Number | Structure | Appearance | Preparation Method: | Precursor(s) |
|---|---|---|---|---|
| 1.26 | 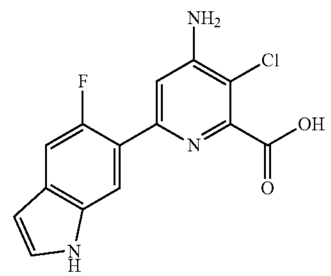 [SMILES: Nc1cc(-c2cc3[nH]ccc3cc2F)nc(C(=O)O)c1Cl] | White Solid | Hydrolysis 2 | Compound 1.25 |
| 1.27 | 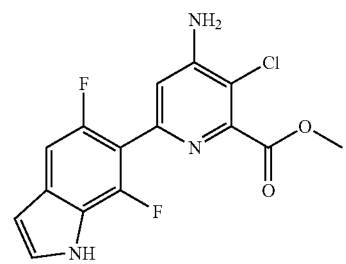 [SMILES: COC(=O)c1nc(-c2c(F)cc3cc[nH]c3c2F)cc(N)c1Cl] | White solid | Coupling 7 | Head K |
| 1.28 | 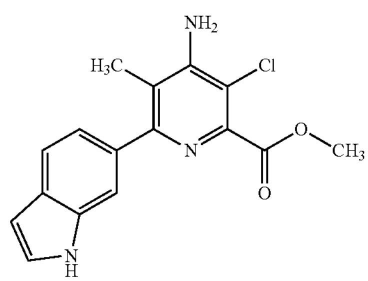 [SMILES: COC(=O)c1nc(-c2ccc3cc[nH]c3c2)c(C)c(N)c1Cl] | Yellow Powder | Coupling 1 | Head D; (1H-indol-6-yl)boronic acid |
| 1.29 | 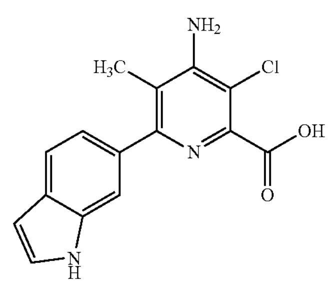 [SMILES: Cc1c(-c2ccc3cc[nH]c3c2)nc(C(=O)O)c(Cl)c1N] | Pale Pink Flaky Solid | Hydrolysis 1 | Compound 1.28 |
| 1.30 | 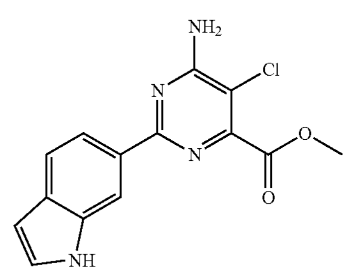 [SMILES: COC(=O)c1nc(-c2ccc3cc[nH]c3c2)nc(N)c1Cl] | White solid | Coupling 1 | Head E |

TABLE 10-continued

Compound Number, Structure, Appearance, and Preparation Method

| Compound Number | Structure | Appearance | Preparation Method: | Precursor(s) |
|---|---|---|---|---|
| 1.31 | 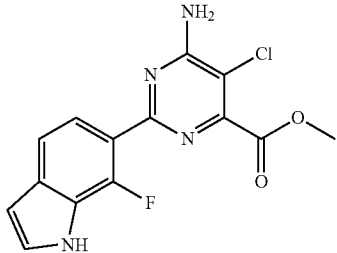 [SMILES: COC(=O)c1nc(-c2ccc3cc[nH]c3c2F)nc(N)c1Cl] | Yellow solid | Coupling 8 | Head E |
| 1.32 | 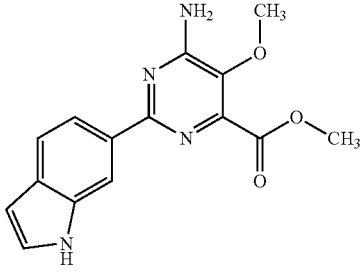 [SMILES: COC(=O)c1nc(-c2ccc3cc[nH]c3c2)nc(N)c1OC] | White Solid | Coupling 4 | Head C; 6-(4,4,5,5-tetramethyl-1,3,2-dioxaborolan-2-yl)-1H-indole |
| 1.33 | 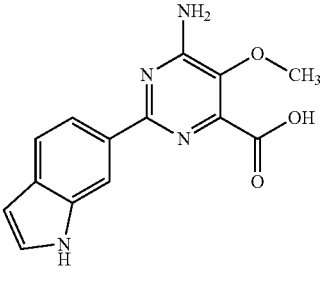 [SMILES: COc1c(N)nc(-c2ccc3cc[nH]c3c2)nc1C(=O)O] | Yellow Solid | Hydrolysis 2 | Compound 1.32 |
| 1.34 | 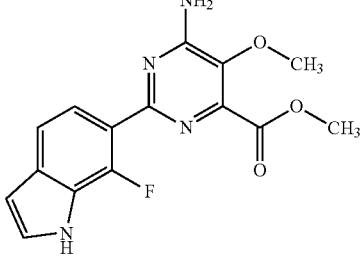 | White Solid | Coupling 4 | Head C; 7-fluoro-6-(4,4,5,5-tetramethyl-1,3,2-dioxaborolan-2-yl)-1H-indole |
| 1.35 | 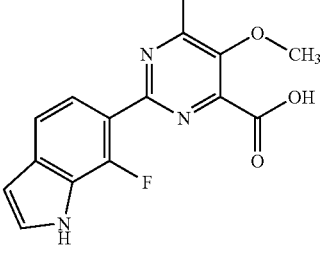 | Yellow Solid | Hydrolysis 2 | Compound 1.34 |

TABLE 10-continued

Compound Number, Structure, Appearance, and Preparation Method

| Compound Number | Structure | Appearance | Preparation Method: | Precursor(s) |
|---|---|---|---|---|
| 1.36 | 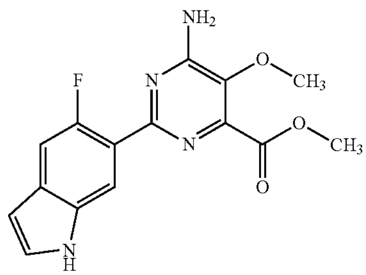 [SMILES: COC(=O)c1nc(-c2cc3[nH]ccc3cc2F)nc(N)c1OC] | White Solid | Coupling 4 | Head C; 5-fluoro-6-(4,4,5,5-tetramethyl-1,3,2-dioxaborolan-2-yl)-1H-indole |
| 1.37 | 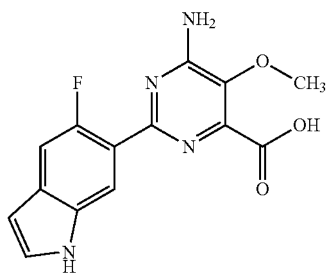 [SMILES: COc1c(N)nc(-c2cc3[nH]ccc3cc2F)nc1C(=O)O] | Yellow Solid | Hydrolysis 2 | Compound 1.36 |
| 1.38 | 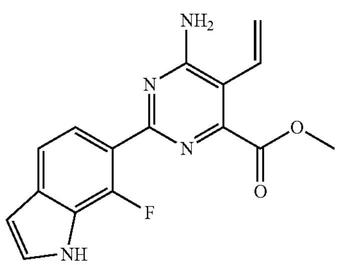 [SMILES: C=Cc1c(N)nc(-c2ccc3cc[nH]c3c2F)nc1C(=O)OC] | Tan solid | Coupling 8 | Head P |
| 1.39 | 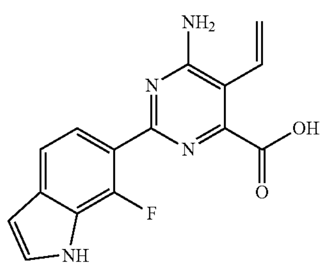 [SMILES: C=Cc1c(N)nc(-c2ccc3cc[nH]c3c2F)nc1C(=O)O] | | Hydrolysis 1 | Compound 1.38 |
| 1.40 | 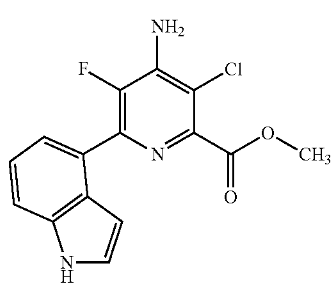 [SMILES: COC(=O)c1nc(-c2cccc3[nH]ccc23)c(F)c(N)c1Cl] | White Solid | Coupling 1 | Head B; 4-(4,4,5,5-tetramethyl-1,3,2-dioxaborolan-2-yl)-1H-indole |

TABLE 10-continued

Compound Number, Structure, Appearance, and Preparation Method

| Compound Number | Structure | Appearance | Preparation Method: | Precursor(s) |
|---|---|---|---|---|
| 1.41 | 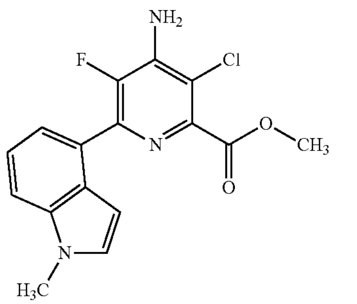 | White Solid | Coupling 1 | Head B; 1-methyl-4-(4,4,5,5-tetramethyl-1,3,2-dioxaborolan-2-yl)-1H-indole |
| 1.42 | 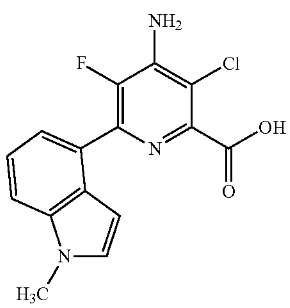 | Off-White Solid | Hydrolysis 1 | Compound 1.41 |
| 1.43 | 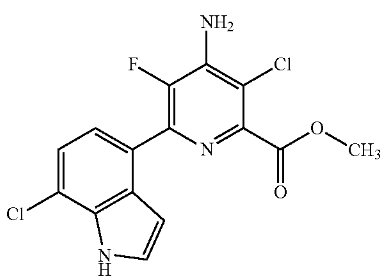 [SMILES: COC(=O)c1nc(-c2ccc(Cl)c3[nH]ccc23)c(F)c(N)c1Cl] | White Solid | Coupling 4 | Head B; 7-chloro-4-(4,4,5,5-tetramethyl-1,3,2-dioxaborolan-2-yl)-1H-indole |
| 1.44 | 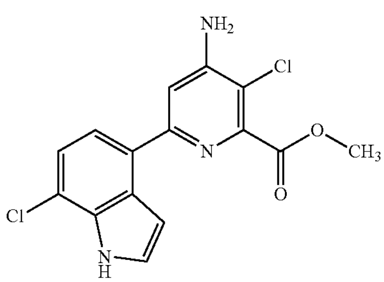 [SMILES: COC(=O)c1nc(-c2ccc(Cl)c3[nH]ccc23)cc(N)c1Cl] | Off White Solid Bottom of Form | Coupling 6 | Head L; 7-chloro-4-(4,4,5,5-tetramethyl-1,3,2-dioxaborolan-2-yl)-1H-indole |
| 1.45 | 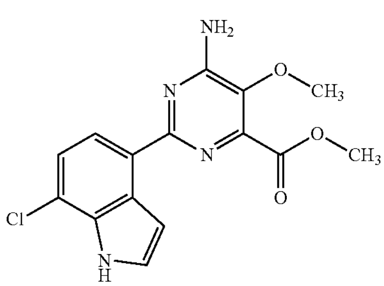 [SMILES: COC(=O)c1nc(-c2ccc(Cl)c3[nH]ccc23)nc(N)c1OC] | Off White Solid | Coupling 4 | Head C; 7-chloro-4-(4,4,5,5-tetramethyl-1,3,2-dioxaborolan-2-yl)-1H-indole |

TABLE 10-continued

Compound Number, Structure, Appearance, and Preparation Method

| Compound Number | Structure | Appearance | Preparation Method: | Precursor(s) |
|---|---|---|---|---|
| 1.46 | 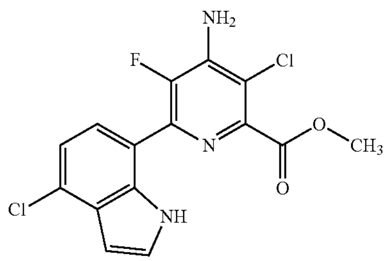 [SMILES: COC(=O)c1nc(-c2ccc(Cl)c3cc[nH]c23)c(F)c(N)c1Cl] | White Solid | Coupling 4 | Head B; 4-chloro-7-(4,4,5,5-tetramethyl-1,3,2-dioxaborolan-2-yl)-1H-indole |
| 1.47 | 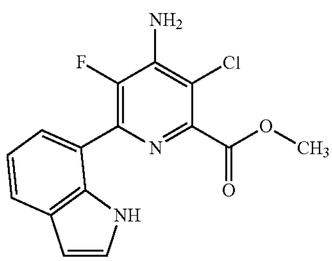 [SMILES: COC(=O)c1nc(-c2cccc3cc[nH]c23)c(F)c(N)c1Cl] | Off-White Solid | Coupling 1 | Head B; 7-(4,4,5,5-tetramethyl-1,3,2-dioxaborolan-2-yl)-1H-indole |
| 1.48 | 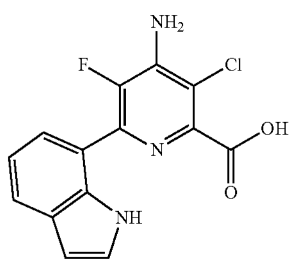 [SMILES: Nc1c(F)c(-c2cccc3cc[nH]c23)nc(C(=O)O)c1Cl] | Tan Solid | Hydrolysis 1 | Compound 1.47 |
| 1.49 | 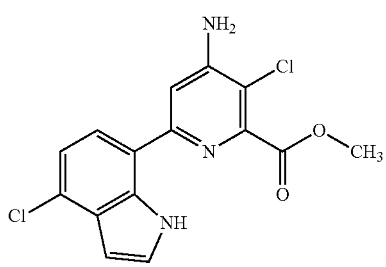 [SMILES: COC(=O)c1nc(-c2ccc(Cl)c3cc[nH]c23)cc(N)c1Cl] | Off White Solid | Coupling 6 | Head L; 4-chloro-7-(4,4,5,5-tetramethyl-1,3,2-dioxaborolan-2-yl)-1H-indole |
| 1.50 | 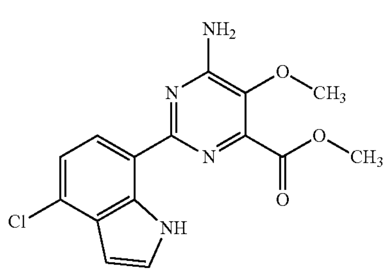 [SMILES: COC(=O)c1nc(-c2ccc(Cl)c3cc[nH]c23)nc(N)c1OC] | Off White Solid | Coupling 4 | Head C; 4-chloro-7-(4,4,5,5-tetramethyl-1,3,2-dioxaborolan-2-yl)-1H-indole |

TABLE 10-continued

Compound Number, Structure, Appearance, and Preparation Method

| Compound Number | Structure | Appearance | Preparation Method: | Precursor(s) |
|---|---|---|---|---|
| 2.01 | 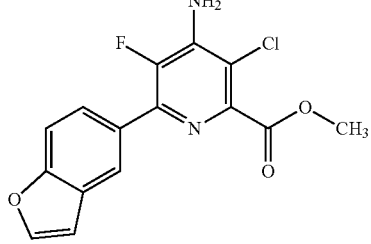 | Yellow Solid | 134 | Head B; 2-(benzofuran-5-yl)-4,4,5,5-tetramethyl-1,3,2-dioxaborolane |
| 2.02 | 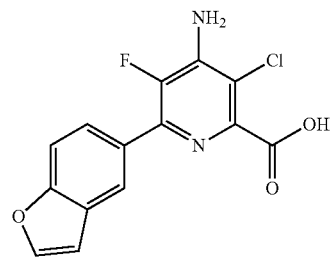 [SMILES: Nc1c(F)c(-c2ccc3occc3c2)nc(C(=O)O)c1Cl] | White Solid | Hydrolysis 1 | Compound 2.01 |
| 2.03 | 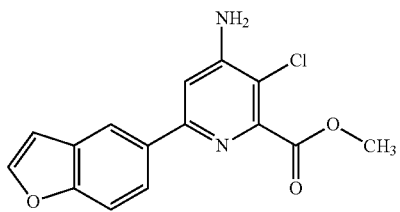 [SMILES: COC(=O)c1nc(-c2ccc3occc3c2)cc(N)c1Cl] | yellow solid | Coupling 1 | Head L; benzofuran-5-ylboronic acid |
| 2.04 | 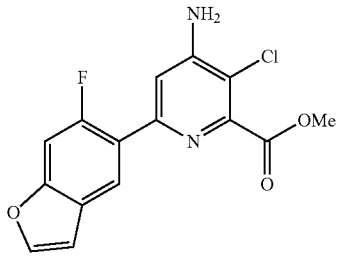 [SMILES: COC(=O)c1nc(-c2cc3ccoc3cc2F)cc(N)c1Cl] | Off-White Solid | Coupling 1 | Head A; 2-(6-fluorobenzofuran-5-yl)-4,4,5,5-tetramethyl-1,3,2-dioxaborolane |
| 2.05 | 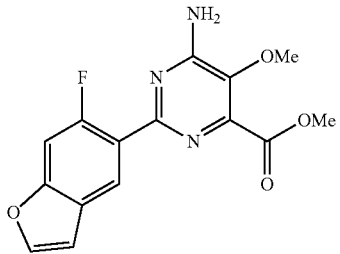 [SMILES: COC(=O)c1nc(-c2cc3ccoc3cc2F)nc(N)c1OC] | White Solid | Coupling 1 | Head C; 2-(6-fluorobenzofuran-5-yl)-4,4,5,5-tetramethyl-1,3,2-dioxaborolane |
| 2.06 | 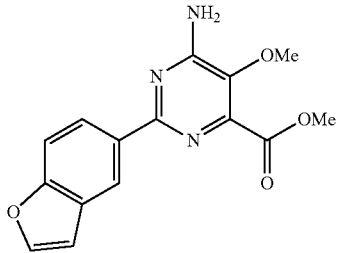 [SMILES: COC(=O)c1nc(-c2ccc3occc3c2)nc(N)c1OC] | Lt Yellow Oil At Room Temp | Coupling 1 | Head C; benzofuran-5-boronic acid |

TABLE 10-continued

Compound Number, Structure, Appearance, and Preparation Method

| Compound Number | Structure | Appearance | Preparation Method: | Precursor(s) |
|---|---|---|---|---|
| 2.07 | 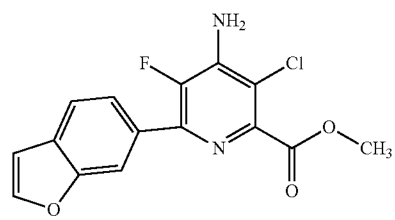 [SMILES: COC(=O)c1nc(-c2ccc3ccoc3c2)c(F)c(N)c1Cl] | White Solid | 134 | Head B; 2-(benzofuran-6-yl)-4,4,5,5-tetramethyl-1,3,2-dioxaborolane |
| 2.08 | 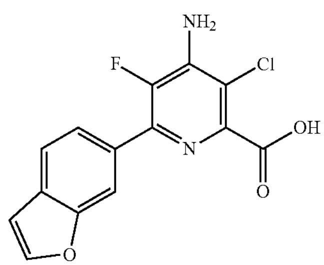 | Off White Solid | Hydrolysis 1 | Compound 2.07 |
| 2.09 | 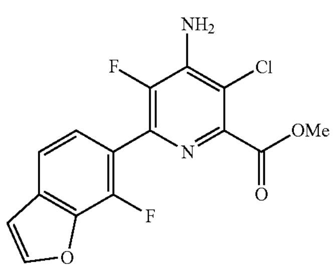 [SMILES: COC(=O)c1nc(-c2ccc3ccoc3c2F)c(F)c(N)c1Cl] | Light Yellow Solid | Coupling 1 | Head B;2-(7-fluorobenzofuran-6-yl)-4,4,5,5-tetramethyl-1,3,2-dioxaborolane |
| 2.10 | 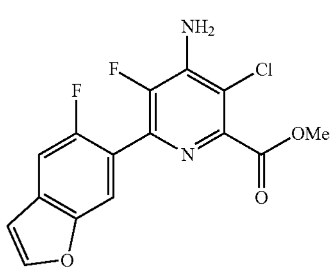 [SMILES: COC(=O)c1nc(-c2cc3occc3cc2F)c(F)c(N)c1Cl] | White Solid | Coupling 1 | Head B; 2-(5-fluorobenzofuran-6-yl)-4,4,5,5-tetramethyl-1,3,2-dioxaborolane |
| 2.11 | 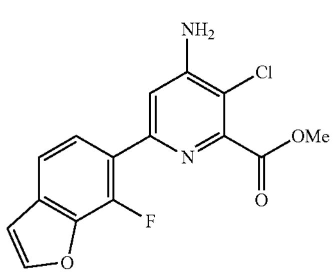 [SMILES: COC(=O)c1nc(-c2ccc3ccoc3c2F)cc(N)c1Cl] | Off-White Solid | Coupling 1 | Head A; 2-(7-fluorobenzofuran-6-yl)-4,4,5,5-tetramethyl-1,3,2-dioxaborolane |

TABLE 10-continued

Compound Number, Structure, Appearance, and Preparation Method

| Compound Number | Structure | Appearance | Preparation Method: | Precursor(s) |
|---|---|---|---|---|
| 2.12 | 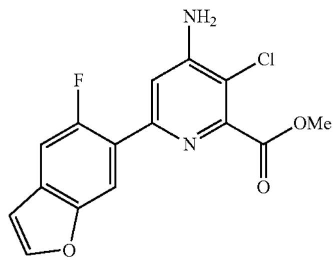 [SMILES: COC(=O)c1nc(-c2cc3occc3cc2F)cc(N)c1Cl] | Beige Solid | Coupling 1 | Head A; 2-(5-fluorobenzofuran-6-yl)-4,4,5,5-tetramethyl-1,3,2-dioxaborolane |
| 2.13 | 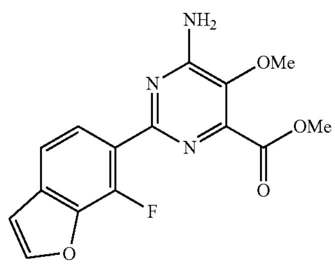 [SMILES: COC(=O)c1nc(-c2ccc3ccoc3c2F)nc(N)c1OC] | White Solid | Coupling 1 | Head C; 2-(7-fluorobenzofuran-6-yl)-4,4,5,5-tetramethyl-1,3,2-dioxaborolane |
| 2.14 | 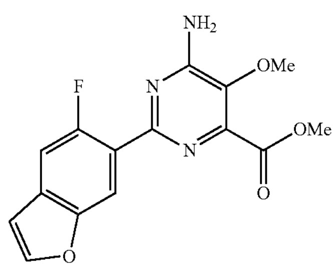 [SMILES: COC(=O)c1nc(-c2cc3occc3cc2F)nc(N)c1OC] | Off-White Solid | Coupling 1 | Head C; 2-(5-fluorobenzofuran-6-yl)-4,4,5,5-tetramethyl-1,3,2-dioxaborolane |
| 2.15 | 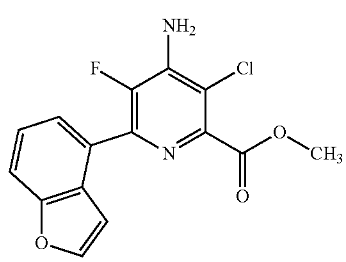 [SMILES: COC(=O)c1nc(-c2cccc3occc23)c(F)c(N)c1Cl] | White Solid | Coupling 5 | Head B; 2-(benzofuran-4-yl)-4,4,5,5-tetramethyl-1,3,2-dioxaborolane |
| 2.16 | 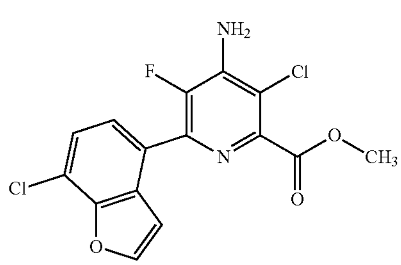 [SMILES: COC(=O)c1nc(-c2ccc(Cl)c3occc23)c(F)c(N)c1Cl] | White Solid | Coupling 5 | Head B; 2-(7-chlorobenzofuran-4-yl)-5,5-dimethyl-1,3,2-dioxaborinane |

TABLE 10-continued

Compound Number, Structure, Appearance, and Preparation Method

| Compound Number | Structure | Appearance | Preparation Method: | Precursor(s) |
|---|---|---|---|---|
| 2.17 | 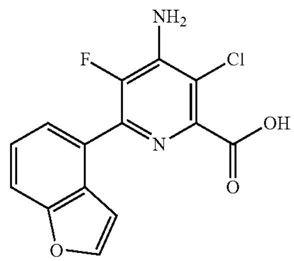 [SMILES: Nc1c(F)c(-c2cccc3occc23)nc(C(=O)O)c1Cl] | Tan Solid | Hydrolysis 1 | Compound 2.15 |
| 2.18 | 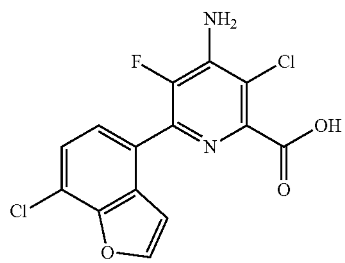 [SMILES: Nc1c(F)c(-c2ccc(Cl)c3occc23)nc(C(=O)O)c1Cl] | Off White Solid | Hydrolysis 1 | Compound 2.16 |
| 2.19 | 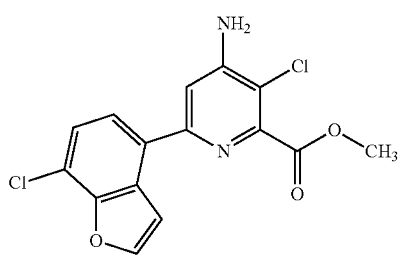 [SMILES: COC(=O)c1nc(-c2ccc(Cl)c3occc23)cc(N)c1Cl] | Light Yellow Solid | Coupling 5 | Head M; 2-(7-chlorobenzofuran-4-yl)-5,5-dimethyl-1,3,2-dioxaborinane |
| 2.20 | 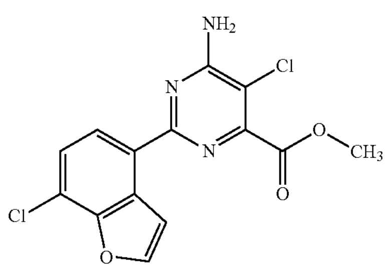 [SMILES: COC(=O)c1nc(-c2ccc(Cl)c3occc23)nc(N)c1Cl] | Tan Solid | Coupling 5 | Head E; 2-(7-chlorobenzofuran-4-yl)-5,5-dimethyl-1,3,2-dioxaborinane |
| 2.21 | 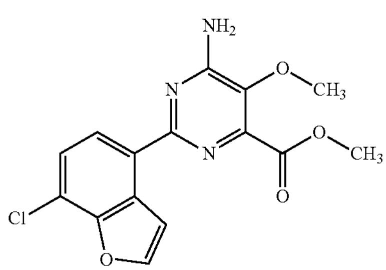 [SMILES: COC(=O)c1nc(-c2ccc(Cl)c3occc23)nc(N)c1OC] | Tan Solid | Coupling 5 | Head C; 2-(7-chlorobenzofuran-4-yl)-5,5-dimethyl-1,3,2-dioxaborinane |

TABLE 10-continued

Compound Number, Structure, Appearance, and Preparation Method

| Compound Number | Structure | Appearance | Preparation Method: | Precursor(s) |
|---|---|---|---|---|
| 2.22 | 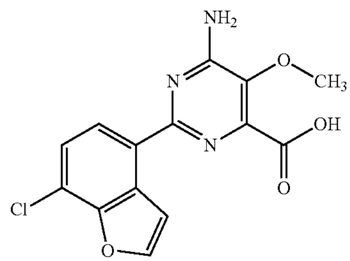 [SMILES: COc1c(N)nc(-c2ccc(Cl)c3occc23)nc1C(=O)O] | Tan Solid | Hydrolysis 1 | Compound 2.21 |
| 2.23 | 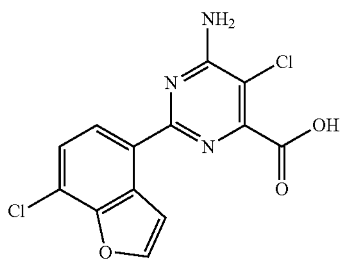 [SMILES: Nc1nc(-c2ccc(Cl)c3occc23)nc(C(=O)O)c1Cl] | Tan Solid | Hydrolysis 1 | Compound 2.20 |
| 2.24 | 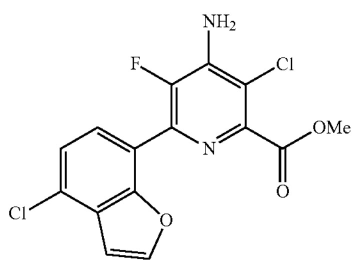 [SMILES: COC(=O)c1nc(-c2ccc(Cl)c3ccoc23)c(F)c(N)c1Cl] | Off-White Solid | Coupling 1 | Head B; 2-(4-chlorobenzofuran-7-yl)-4,4,5,5-tetramethyl-1,3,2-dioxaborolane |
| 2.25 | 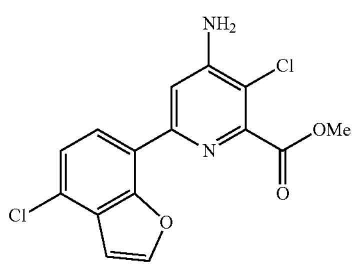 [SMILES: COC(=O)c1nc(-c2ccc(Cl)c3ccoc23)cc(N)c1Cl] | Off-White Solid | Coupling 1 | Head A; 2-(4-chlorobenzofuran-7-yl)-4,4,5,5-tetramethyl-1,3,2-dioxaborolane |
| 2.26 | 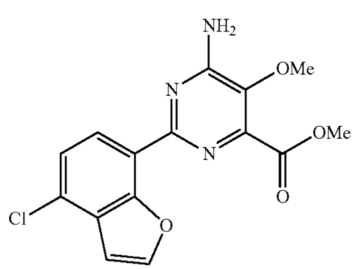 [SMILES: COC(=O)c1nc(-c2ccc(Cl)c3ccoc23)nc(N)c1OC] | Off-White Solid | Coupling 1 | Head C; 2-(4-chlorobenzofuran-7-yl)-4,4,5,5-tetramethyl-1,3,2-dioxaborolane |

TABLE 10-continued

Compound Number, Structure, Appearance, and Preparation Method

| Compound Number | Structure | Appearance | Preparation Method: | Precursor(s) |
|---|---|---|---|---|
| 3.01 | 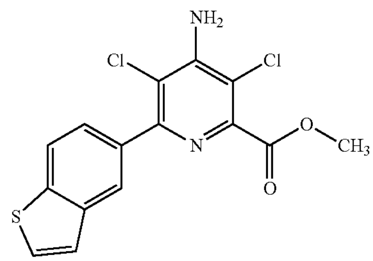 [SMILES: COC(=O)c1nc(-c2ccc3sccc3c2)c(Cl)c(N)c1Cl] | White Solid | Coupling 4 | Head H; 2-(benzo[b]thiophen-5-yl)-4,4,5,5-tetramethyl-1,3,2-dioxaborolane |
| 3.02 | 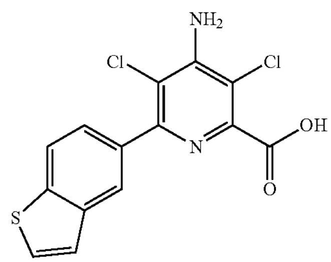 [SMILES: Nc1c(Cl)c(C(=O)O)nc(-c2ccc3sccc3c2)c1Cl] | White Solid | Hydrolysis 2 | Head H; 2-(benzo[b]thiophen-5-yl)-4,4,5,5-tetramethyl-1,3,2-dioxaborolane |
| 3.03 | 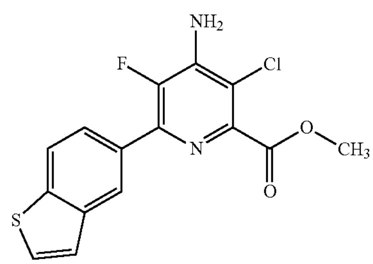 [SMILES: COC(=O)c1nc(-c2ccc3sccc3c2)c(F)c(N)c1Cl] | White Solid | Coupling 2 | Head B; 2-(benzo[b]thiophen-5-yl)-4,4,5,5-tetramethyl-1,3,2-dioxaborolane |
| 3.04 | 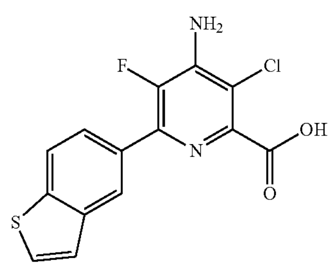 | Tan Solid | Hydrolysis 1 | Compound 3.03 |
| 3.05 | 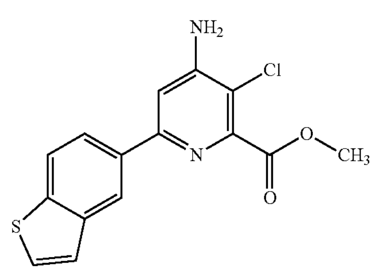 [SMILES: COC(=O)c1nc(-c2ccc3sccc3c2)cc(N)c1Cl] | yellow solid | Coupling 1 | Head L; 2-(benzo[b]thiophen-5-yl)-4,4,5,5-tetramethyl-1,3,2-dioxaborolane |

TABLE 10-continued

Compound Number, Structure, Appearance, and Preparation Method

| Compound Number | Structure | Appearance | Preparation Method | Precursor(s) |
|---|---|---|---|---|
| 3.06 | 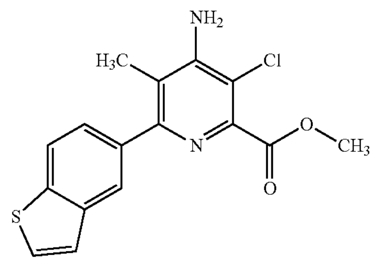 [SMILES: COC(=O)c1nc(-c2ccc3sccc3c2)c(C)c(N)c1Cl] | Off-White Solid | Coupling 1 | Head D; 2-(benzo[b]thiophen-5-yl)-4,4,5,5-tetramethyl-1,3,2-dioxaborolane |
| 3.07 | 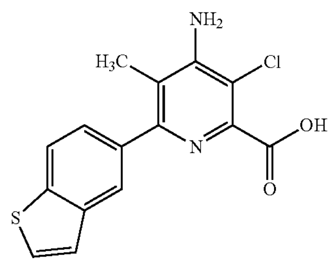 [SMILES: Cc1c(-c2ccc3sccc3c2)nc(C(=O)O)c(Cl)c1N] | Off-White Solid | Hydrolysis 1 | Compound 3.06 |
| 3.08 | 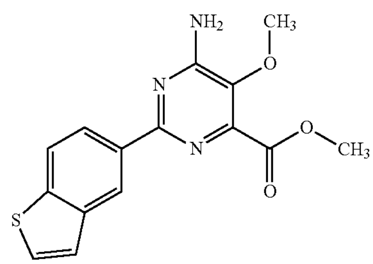 [SMILES: COC(=O)c1nc(-c2ccc3sccc3c2)nc(N)c1OC] | White Solid | Coupling 4 | Head C; 2-(benzo[b]thiophen-5-yl)-4,4,5,5-tetramethyl-1,3,2-dioxaborolane |
| 3.09 | 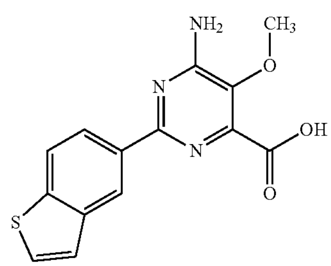 [SMILES: COc1c(N)nc(-c2ccc3sccc3c2)nc1C(=O)O] | White Solid | Hydrolysis 2 | Compound 3.08 |
| 3.10 | 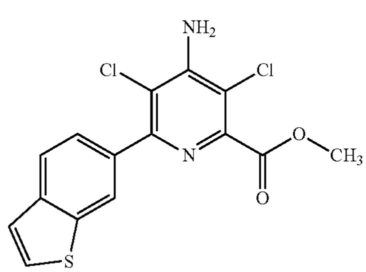 [SMILES: COC(=O)c1nc(-c2ccc3ccsc3c2)c(Cl)c(N)c1Cl] | White Solid | Coupling 1 | Head H; 2-(benzo[b]thiophen-6-yl)-4,4,5,5-tetramethyl-1,3,2-dioxaborolane |

TABLE 10-continued

Compound Number, Structure, Appearance, and Preparation Method

| Compound Number | Structure | Appearance | Preparation Method: | Precursor(s) |
|---|---|---|---|---|
| 3.11 | 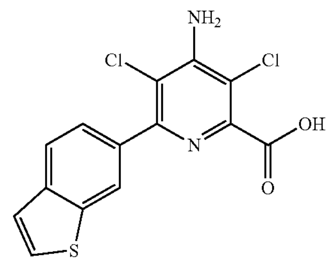 [SMILES: Nc1c(Cl)c(C(=O)O)nc(-c2ccc3ccsc3c2)c1Cl] | Yellow Solid | Hydrolysis 1 | Compound 3.10 |
| 3.12 | 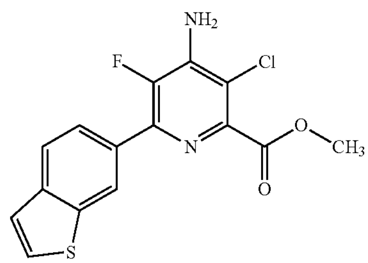 [SMILES: COC(=O)c1nc(-c2ccc3ccsc3c2)c(F)c(N)c1Cl] | Light Yellow Solid | Coupling 5 | Head B; 2-(benzothiophen-6-yl)-4,4,5,5-tetramethyl-1,3,2-dioxaborolane |
| 3.13 | 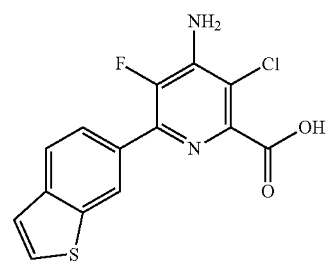 [SMILES: Nc1c(F)c(-c2ccc3ccsc3c2)nc(C(=O)O)c1Cl] | Tan Solid | Hydrolysis 1 | Compound 3.12 |
| 3.14 | 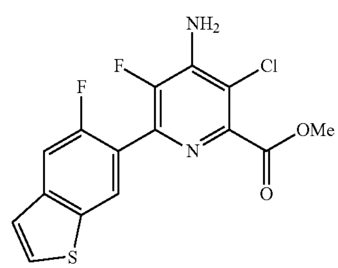 | Light Yellow Solid | Coupling 1 | Head B; 2-(5-fluorobenzothiophen-6-yl)-4,4,5,5-tetramethyl-1,3,2-dioxaborolane |
| 3.15 | 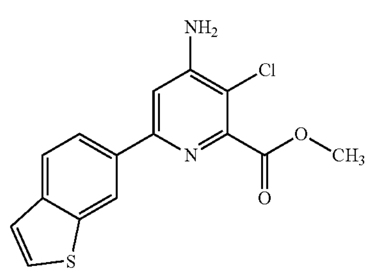 [SMILES: COC(=O)c1nc(-c2ccc3ccsc3c2)cc(N)c1Cl] | Off-White Brittle Solid | Coupling 1 | Head A; 2-(benzo[b]thiophen-6-yl)-4,4,5,5-tetramethyl-1,3,2-dioxaborolane |

TABLE 10-continued

Compound Number, Structure, Appearance, and Preparation Method

| Compound Number | Structure | Appearance | Preparation Method: | Precursor(s) |
|---|---|---|---|---|
| 3.16 | 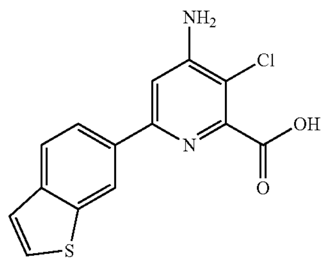 [SMILES: Nc1cc(-c2ccc3ccsc3c2)nc(C(=O)O)c1Cl] | White Solid | Hydrolysis 1 | Compound 3.15 |
| 3.17 | 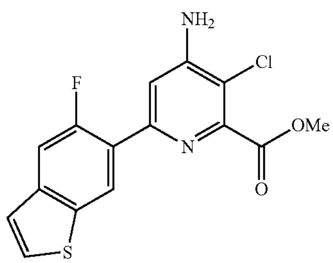 | White Solid | Coupling 1 | Head A; 2-(5-fluorobenzothiophen-6-yl)-4,4,5,5-tetramethyl-1,3,2-dioxaborolane |
| 3.18 | 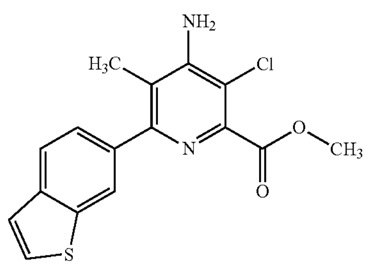 [SMILES: COC(=O)c1nc(-c2ccc3ccsc3c2)c(C)c(N)c1Cl] | Yellow Solid | Coupling 1 | Head D; 2-(benzo[b]thiophen-6-yl)-4,4,5,5-tetramethyl-1,3,2-dioxaborolane |
| 3.19 | 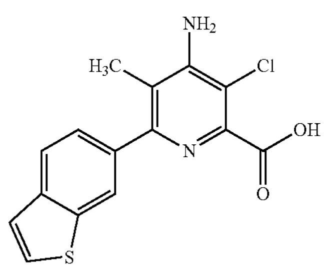 [SMILES: Cc1c(-c2ccc3ccsc3c2)nc(C(=O)O)c(Cl)c1N] | Off-White Solid | Hydrolysis 1 | Compound 3.18 |
| 3.20 | 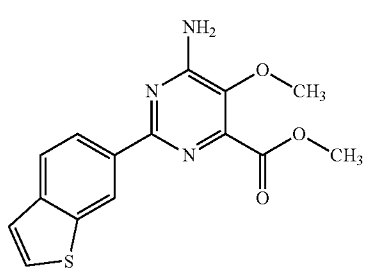 [SMILES: COC(=O)c1nc(-c2ccc3ccsc3c2)nc(N)c1OC] | Light Yellow Solid | Coupling 4 | Head C; 2-(benzo[b]thiophen-6-yl)-4,4,5,5-tetramethyl-1,3,2-dioxaborolane |

TABLE 10-continued

Compound Number, Structure, Appearance, and Preparation Method

| Compound Number | Structure | Appearance | Preparation Method: | Precursor(s) |
|---|---|---|---|---|
| 3.21 | 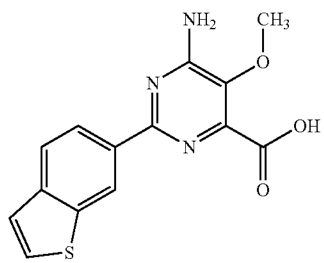 [SMILES: COc1c(N)nc(-c2ccc3ccsc3c2)nc1C(=O)O] | White Solid | Hydrolysis 2 | Compound 3.20 |
| 3.22 | 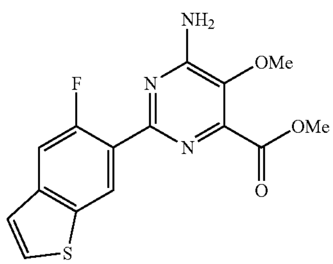 | Off-White Solid | Coupling 1 | Head C; 2-(5-fluorobenzothiophen-6-yl)-4,4,5,5-tetramethyl-1,3,2-dioxaborolane |
| 3.23 | 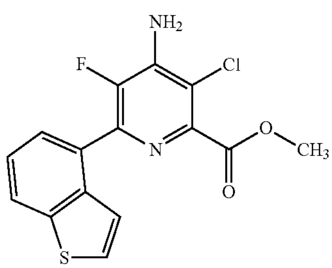 [SMILES: COC(=O)c1nc(-c2cccc3sccc23)c(F)c(N)c1Cl] | White Solid | Coupling 1 | Head B; benzo[b]thiophen-4-ylboronic acid |
| 3.24 | 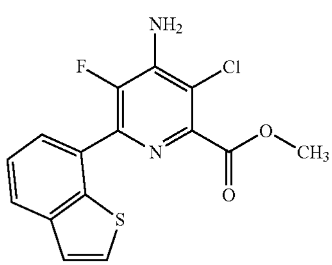 [SMILES: COC(=O)c1nc(-c2cccc3ccsc23)c(F)c(N)c1Cl] | White Solid | Coupling 1 | Head B; benzo[b]thiophen-7-ylboronic acid |
| 3.25 | 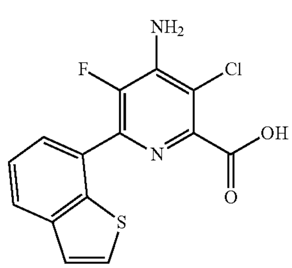 [SMILES: Nc1c(F)c(-c2cccc3ccsc23)nc(C(=O)O)c1Cl] | White Solid | Hydrolysis 1 | Compound 3.24 |

TABLE 10-continued

Compound Number, Structure, Appearance, and Preparation Method

| Compound Number | Structure | Appearance | Preparation Method: | Precursor(s) |
|---|---|---|---|---|
| 3.26 | 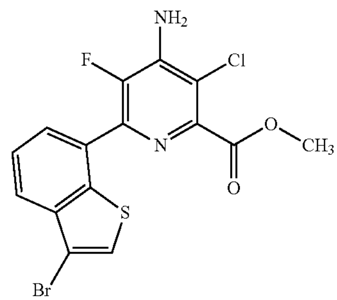 [SMILES: COC(=O)c1nc(-c2cccc3c(Br)csc23)c(F)c(N)c1Cl] | Grey Solid | 140 | As described |
| 3.27 | 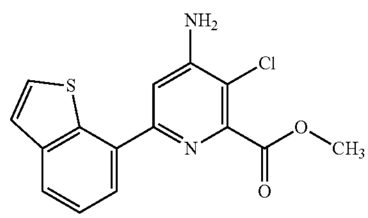 [SMILES: COC(=O)c1nc(-c2cccc3ccsc23)cc(N)c1Cl] | yellow oil | Coupling 1 | Head L; benzo[b]thiophen-7-ylboronic acid |
| 4.01 | 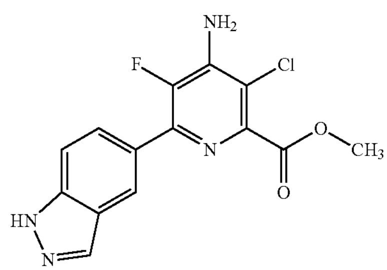 [SMILES: COC(=O)c1nc(-c2ccc3[nH]ncc3c2)c(F)c(N)c1Cl] | White Powder | Coupling 2 | Head B; 1H-Indazol-5-ylboronic acid |
| 4.02 | 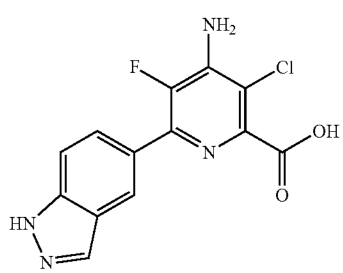 [SMILES: Nc1c(F)c(-c2ccc3[nH]ncc3c2)nc(C(=O)O)c1Cl] | White Powder | Hydrolysis 1 | Compound 4.01 |
| 4.03 | 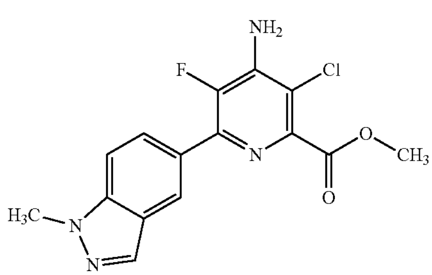 | White Powder | Coupling 2 | Head B; 1-Methyl-1H-indazol-5-ylboronic acid |

TABLE 10-continued

Compound Number, Structure, Appearance, and Preparation Method

| Compound Number | Structure | Appearance | Preparation Method: | Precursor(s) |
|---|---|---|---|---|
| 4.04 | (structure) | White Powder | Hydrolysis 1 | Compound 4.03 |
| 4.05 | (structure) | White Powder | Coupling 2 | Head B; 1H-Indazol-6-ylboronic acid |
| 4.06 | (structure) | Off-White Powder | Hydrolysis 1 | Compound 4.05 |
| 4.07 | (structure) | White Powder | Coupling 2 | Head B; 1-Methyl-1H-indazol-6-ylboronic acid |
| 4.08 | (structure) | White Powder | Hydrolysis 1 | Compound 4.07 |

TABLE 10-continued

Compound Number, Structure, Appearance, and Preparation Method

| Compound Number | Structure | Appearance | Preparation Method: | Precursor(s) |
|---|---|---|---|---|
| 4.09 | 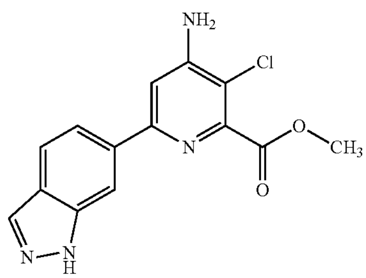 [SMILES: COC(=O)c1nc(-c2ccc3cn[nH]c3c2)cc(N)c1Cl] | White Solid | Coupling 1 | Head A; (1H-indazol-6-yl)boronic acid |
| 4.10 | 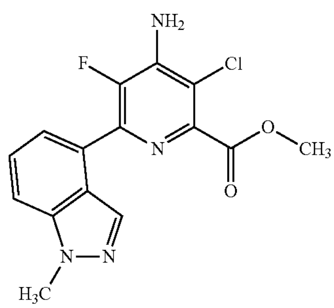 [SMILES: COC(=O)c1nc(-c2cccc3c2cnn3C)c(F)c(N)c1Cl] | Yellow Solid | Coupling 1 | Head B; 1-methyl-4-(4,4,5,5-tetramethyl-1,3,2-dioxaborolan-2-yl)-1H-indazole |
| 4.11 | 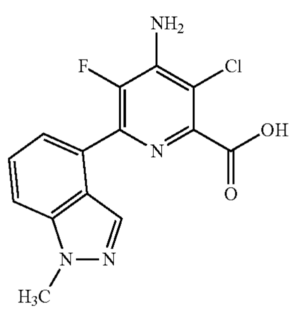 [SMILES: Cn1ncc2c(-c3nc(C(=O)O)c(Cl)c(N)c3F)cccc21] | Off-White Solid | Hydrolysis 1 | Compound 4.10 |
| 4.12 | 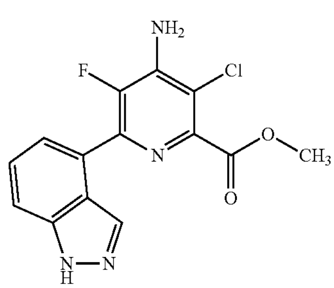 [SMILES: COC(=O)c1nc(-c2cccc3[nH]ncc23)c(F)c(N)c1Cl] | White Solid | Coupling 1 | Head B; 1H-indazol-4-ylboronic acid |
| 4.13 | 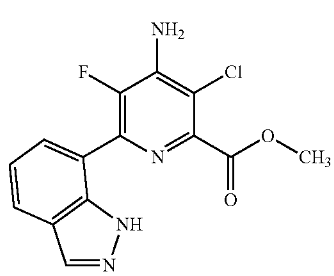 [SMILES: COC(=O)c1nc(-c2cccc3cn[nH]c23)c(F)c(N)c1Cl] | White Solid | Coupling 1 | Head B; 7-(4,4,5,5-tetramethyl-1,3,2-dioxaborolan-2-yl)-1H-indazole |

TABLE 10-continued

Compound Number, Structure, Appearance, and Preparation Method

| Compound Number | Structure | Appearance | Preparation Method: | Precursor(s) |
|---|---|---|---|---|
| 5.01 | 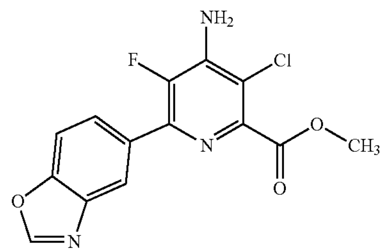 [SMILES: COC(=O)c1nc(-c2ccc3ocnc3c2)c(F)c(N)c1Cl] | Off White Solid | Coupling 5 | Head B; BENZOOXAZOLE-5-BORONIC ACID PINACOL ESTER |
| 6.01 | 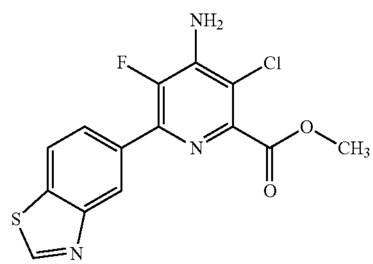 [SMILES: COC(=O)c1nc(-c2ccc3scnc3c2)c(F)c(N)c1Cl] | Light Brown Solid | Coupling 3 | As described |
| 6.02 | 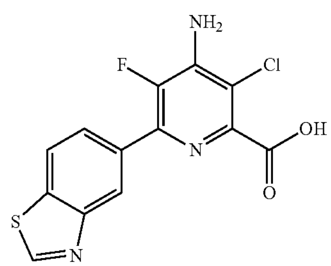 [SMILES: Nc1c(F)c(-c2ccc3scnc3c2)nc(C(=O)O)c1Cl] | Light Brown Solid | Hydrolysis 1 | Compound 6.01 |
| 7.01 | 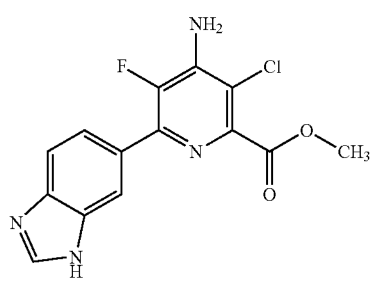 [SMILES: COC(=O)c1nc(-c2ccc3nc[nH]c3c2)c(F)c(N)c1Cl] | Off-White Powder | Coupling 2 | Head B; 6-(4,4,5,5-Tetramethyl-1,3,2-dioxaborolan-2-yl)-1H-benzo[d]imidazole |
| 7.02 | 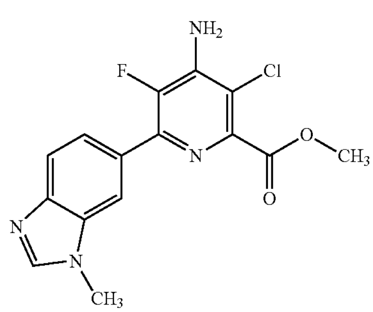 [SMILES: COC(=O)c1nc(-c2ccc3ncn(C)c3c2)c(F)c(N)c1Cl] | White Powder | Coupling 2 | Head B; 1-Methyl-1H-benzo[d]imidazol-6-ylboronic acid |

TABLE 10-continued

Compound Number, Structure, Appearance, and Preparation Method

| Compound Number | Structure | Appearance | Preparation Method: | Precursor(s) |
|---|---|---|---|---|
| 7.03 | 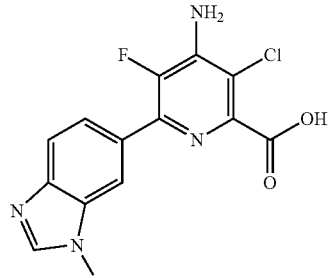 | White Powder | Hydrolysis 1 | Compound 7.02 |
| 8.01 | 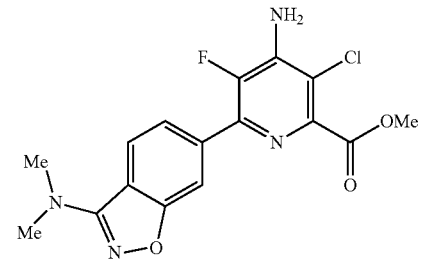 [SMILES: COC(=O)c1nc(-c2ccc3c(N(C)C)noc3c2)c(F)c(N)c1Cl] | Yellow Solid | Coupling 1 | Head B; N,N-dimethyl-6-(4,4,5,5-tetramethyl-1,3,2-dioxaborolan-2-yl)benzo[d]isoxazol-3-amine |
| 9.01 | 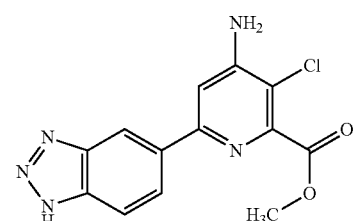 | White Solid | Coupling 7 | Head K; 6-bromo-1H-benzo[d][1,2,3]triazole |

TABLE 11

Analytical Data for Compounds in Table 1

| C. No. | MP (° C.) | HNMR |
|---|---|---|
| 1.01 | 166-168 | $^1$H NMR (300 MHz, DMSO-$d_6$) δ 8.06 (s, 1H), 7.67 (br d, J = 8 Hz, 1H), 7.53 (d, J = 8 Hz, 1H), 7.39 (d, J = 3 Hz, 1H), 6.77 (br s, 2H), 6.54 (d, J = 3 Hz, 1H), 3.83 (s, 3H) |
| 1.02 | 221-224 | $^1$H NMR (300 MHz, DMSO-$d_6$) δ 8.04 (s, 1H), 7.59 (dt, J = 7, 1.5 Hz, 1H), 7.48 (d, J = 7 Hz, 1H), 7.41 (t, J = 3 Hz, 1H), 6.85 (br s, 2H), 6.54 (m, 1H), 3.89 (s, 3H) |
| 1.03 | 125-127 | $^1$H NMR (300 MHz, DMSO-$d_6$) δ 8.21 (s, 1H), 7.82 (dt, J = 9, 1.5 Hz, 1H), 7.39 (d, J = 9 Hz, 1H), 7.08 (d, J = 3 Hz, 1H), 6.56 (d, J = 3 Hz, 1H), 4.84 (br s, 2H), 3.99 (s, 3H), 3.82 (s, 3H) |
| 1.04 | 180-182 | $^1$H NMR (300 MHz, DMSO-$d_6$) δ 11.26 (br s, 1H), 8.05 (s, 1H), 7.61 (dt, J = 9, 1.5 Hz, 1H), 7.48 (d, J = 9 Hz, 1H), 7.41 (t, J = 3 Hz, 1H), 7.67 (br s, 2H), 6.54 (m, 1H) |
| 1.05 | 174-179 | $^1$H NMR (400 MHz, CDCl$_3$) δ 8.50 (s, 1H), 7.65 (d, J = 8.2 Hz, 2H), 7.40 (dd, J = 8.3, 1.4 Hz, 1H), 7.23-7.17 (m, 1H), 6.54-6.48 (m, 1H), 5.30 (d, J = 3.9 Hz, 2H), 3.94 (s, 3H) |
| 1.06 | 160-164 | $^1$H NMR (400 MHz, DMSO-$d_6$) δ 13.64 (s, 1H), 11.26 (s, 1H), 7.67-7.63 (m, 1H), 7.60 (d, J = 8.3 Hz, 1H), 7.48-7.41 (m, 1H), 7.25 (dd, J = 8.2, 1.5 Hz, 1H), 6.89 (s, 2H), 6.48 (dd, J = 2.5, 1.5 Hz, 1H) |
| 1.07 | 185-190 | $^1$H NMR (400 MHz, DMSO) δ 11.79 (s, 1H), 7.94 (s, 2H), 7.55 (m, 1H), 7.52 (m, 1H), 7.40 (d, J = 8.4 Hz, 1H), 6.55 (m, 1H), 3.93 (s, 3H). $^{19}$F NMR (376 MHz, DMSO) δ −132.43. MP 185-190° C. ESIMS m/z 321 [(M + H)+]. |
| 1.08 | 66-69 | $^1$H NMR (300 MHz, CDCl$_3$) δ 8.31 (br s, 1H), 8.02 (s, 1H), 7.71 (s, 2H), 7.29 (t, J = 3 Hz, 1H), 6.58 (m, 1H), 4.86 (br s, 2H), 3.99 (s, 3H) |
| 1.09 | 138-140 | $^1$H NMR (300 MHz, DMSO-$d_6$) δ 7.95 (s, 1H), 7.63 (d, J = 8 Hz, 1H), 7.54 (dt, J = 8, 2 Hz, 1H), 7.47 (t, J = 3 Hz, 1H), 6.79 (br s, 2H), 6.48 (m, 1H) |

TABLE 11-continued

Analytical Data for Compounds in Table 1

| C. No. | MP (° C.) | HNMR |
|---|---|---|
| 1.10 | 116-119 | $^1$H NMR (400 MHz, CDCl$_3$) δ 7.94 (t, J = 1 Hz, 1H), 7.69 (br s, 2H), 7.13 (d, J = 3 Hz, 1H), 6.50 (dd, J = 3, 1 Hz, 1H), 4.85 (br s, 2H), 3.99 (s, 3H), 3.84 (s, 3H) |
| 1.11 | 173-176 | $^1$H NMR (400 MHz, DMSO-d$_6$) δ 7.93 (s, 1H), 7.66 (d, J = 8.5 Hz, 1H), 7.59 (d, J = 8.5 Hz, 1H), 7.46 (d, J = 3 Hz, 1H), 6.50 (d, J = 3 Hz, 1H), 6.37 (br s, 2H), 3.87 (s, 3H) |
| 1.12 | | $^1$H NMR (400 MHz, CDCl3) δ 7.49 (d, J = 8.1 Hz, 1H), 7.40 (d, J = 3.2 Hz, 1H), 7.29 (dd, J = 8.1, 5.9 Hz, 1H), 4.90 (s, 2H), 3.98 (s, 3H), 1.68 (m, 3H), 1.14 (d, J = 7.6 Hz, 18H). $^{19}$F NMR (376 MHz, CDCl$_3$) δ −124.55, −124.65, −136.90, −137.00. MP: 181-182° C. ESIMS m/z 492 [(M − H)−]. |
| 1.13 | | $^1$H NMR (DMSO-d$_6$) δ 3.88 (s, 3H), 6.49 (ddd, J = 2.9, 1.9, 0.8 Hz, 1H), 6.96 (s, 2H), 7.43 (d, J = 11.1 Hz, 1H), 7.50 (d, J = 6.0 Hz, 1H), 7.54 (t, J = 2.8 Hz, 1H), 11.32 (s, 1H). |
| 1.14 | | $^1$H NMR (DMSO-d$_6$) δ 6.46-6.52 (m, 1H), 6.88 (s, 2H), 7.42 (d, J = 11.1 Hz, 1H), 7.49-7.56 (m, 2H), 11.33 (s, 1H), 13.56 (s, 1H). |
| 1.15 | | $^1$H NMR (DMSO-d$_6$) δ 3.88 (s, 3H), 6.59 (td, J = 3.2, 1.9 Hz, 1H), 6.99 (s, 2H), 7.08 (dd, J = 8.2, 6.2 Hz, 1H), 7.47 (d, J = 8.2 Hz, 1H), 7.52 (t, J = 2.8 Hz, 1H), 11.82 (t, J = 2.2 Hz, 1H). |
| 1.16 | | $^1$H NMR (DMSO-d$_6$) δ 6.59 (td, J = 3.2, 1.9 Hz, 1H), 6.90 (s, 2H), 7.10 (dd, J = 8.2, 6.2 Hz, 1H), 7.47 (d, J = 8.1 Hz, 1H), 7.51 (t, J = 2.8 Hz, 1H), 11.81 (s, 1H), 13.57 (s, 1H). |
| 1.17 | 133-140 | $^1$H NMR (400 MHz, DMSO-d6) δ 11.76 (s, 1H), 7.49 (dd, J = 3.0, 2.5 Hz, 1H), 7.44 (d, J = 7.9 Hz, 1H), 7.09 (dd, J = 8.2, 6.2 Hz, 1H), 6.57 (td, J = 3.3, 1.9 Hz, 1H), 6.41 (s, 2H), 3.80 (s, 3H). $^{19}$F NMR (376 MHz, DMSO) δ −134.66, −134.73. 133-140° C. ESIMS m/z 320 [(M + H)+]. |
| 1.18 | 164-166 | $^1$H NMR (400 MHz, Chloroform-d) δ 8.45 (s, 1H), 7.49 (d, J = 8.2, 0.8 Hz, 1H), 7.35-7.28 (m, 2H), 6.94 (dd, J = 18.1, 11.5 Hz, 1H), 6.61 (td, J = 3.4, 2.1 Hz, 1H), 5.72 (dd, J = 11.5, 1.5 Hz, 1H), 5.60 (dd, J = 18.1, 1.5 Hz, 1H), 4.72 (s, 2H), 3.91 (s, 2H). $^{19}$F NMR (376 MHz, CDCl$_3$) δ −135.79, −135.87, −140.98, −141.07. MP 164-166° C. ESIMS m/z 330 [(M + H)+]. |
| 1.19 | | $^1$H NMR (400 MHz, DMSO) δ 11.76 (d, J = 16.4 Hz, 1H), 7.48 (m, 1H), 7.11 (dd, J = 8.2, 6.2 Hz, 1H), 6.79 (dd, J = 17.8, 11.5 Hz, 1H), 6.58 (dd, J = 5.1, 3.2 Hz, 1H), 6.38 (s, 1H), 5.56 (m, 1H). $^{19}$F NMR (376 MHz, DMSO) δ −134.07, −134.15, −143.26, −143.34. ESIMS m/z 316 [(M + H)+]. |
| 1.20 | 203-205 | $^1$H NMR (400 MHz, DMSO) δ 11.76 (s, 1H), 7.49 (dd, J = 6.0, 3.3 Hz, 1H), 7.44 (d, J = 8.2 Hz, 1H), 7.05 (dd, J = 8.1, 6.3 Hz, 1H), 6.57 (m, 1H), 6.49 (s, 2H), 3.84 (s, 3H), 3.79 (s, 3H). $^{19}$F NMR (376 MHz, DMSO) δ −134.75, −134.82, −138.34, −138.42. MP 203-205° C. ESIMS m/z 334 [(M + H)+]. |
| 1.21 | 83-85 | $^1$H NMR (400 MHz, DMSO-d$_6$) δ 11.20 (s, 1H), 8.00 (m, 1H), 7.59 (m, 1H), 7.53 (m, 1H), 7.43 (dd, J = 3.1, 2.4 Hz, 1H), 7.32 (s, 1H), 6.61 (s, 2H), 6.45 (s, 1H), 3.91 (s, 3H) |
| 1.22 | 172-174 | $^1$H NMR (400 MHz, DMSO-d6) δ 11.47 (s, 1H), 7.94 (d, J = 1.2 Hz, 1H), 7.67 (d, J = 8.3 Hz, 2H), 7.52 (t, J = 2.8 Hz, 1H), 7.46 (dd, J = 8.4, 1.7 Hz, 1H), 6.51 (t, J = 2.5 Hz, 1H), NaN (m, 2H) |
| 1.23 | | $^1$H NMR (DMSO-d$_6$) δ 3.89 (s, 3H), 6.54 (td, J = 3.4, 1.9 Hz, 1H), 6.75 (s, 2H), 7.31 (d, J = 1.5 Hz, 1H), 7.37-7.52 (m, 3H), 11.76 (s, 1H). |
| 1.24 | | $^1$H NMR (DMSO-d$_6$) δ 6.50-6.62 (m, 1H), 6.71 (s, 2H), 7.27 (d, J = 1.5 Hz, 1H), 7.41 (d, J = 8.3 Hz, 1H), 7.45-7.53 (m, 2H), 11.76 (d, J = 2.4 Hz, 1H), 13.48 (s, 1H). |
| 1.25 | | $^1$H NMR (DMSO-d$_6$) δ 3.90 (s, 3H), 6.45 (ddd, J = 2.9, 1.9, 0.9 Hz, 1H), 6.75 (s, 2H), 7.29 (d, J = 1.7 Hz, 1H), 7.40 (d, J = 12.7 Hz, 1H), 7.52 (t, J = 2.8 Hz, 1H), 7.93 (dd, J = 6.8, 0.8 Hz, 1H), 11.27 (t, J = 2.3 Hz, 1H). |
| 1.26 | | $^1$H NMR (DMSO-d$_6$) δ 6.45 (t, J = 2.4 Hz, 1H), 6.68 (s, 2H), 7.24 (d, J = 1.6 Hz, 1H), 7.40 (d, J = 12.8 Hz, 1H), 7.52 (t, J = 2.8 Hz, 1H), 7.95 (d, J = 6.7 Hz, 1H), 11.29 (s, 1H), 13.54 (s, 1H). |
| 1.27 | 169-171 | $^1$H NMR (400 MHz, CDCl3) δ 8.45 (s, 1H), 7.29 (t, J = 2.7 Hz, 1H), 7.16 (d, J = 10.0 Hz, 1H), 6.93 (dd, J = 1.5, 0.8 Hz, 1H), 6.54 (s, 1H), 4.82 (s, 2H), 3.98 (s, 3H). $^{19}$F NMR (376 MHz, CDCl$_3$) δ −126.04, −135.41. MP: 169-171° C. ESIMS m/z 336 [(M − H)−]. |
| 1.28 | 231-234 | $^1$H NMR (400 MHz, DMSO-d$_6$) δ 11.15 (s, 1H), 7.57 (d, J = 8.1 Hz, 1H), 7.42 (dd, J = 6.3, 3.6 Hz, 2H), 7.05 (dd, J = 8.2, 1.5 Hz, 1H), 6.47 (dd, J = 2.5, 1.6 Hz, 1H), 6.39 (s, 2H), 3.85 (s, 3H), 2.14 (s, 3H). |
| 1.29 | 168-175 | $^1$H NMR (400 MHz, DMSO-d$_6$) δ 11.31 (s, 1H), 7.66-7.60 (m, 1H), 7.49 (s, 1H), 7.48-7.43 (m, 1H), 7.07 (dt, J = 15.8, 7.9 Hz, 3H), 6.53-6.48 (m, 1H), 2.13 (s, 3H) |
| 1.30 | 240-242 | $^1$H NMR (400 MHz, DMSO-d$_6$) δ 11.33 (s, 1H), 8.37 (s, 1H), 7.96 (dd, J = 8.4, 1.5 Hz, 1H), 7.58 (d, J = 8.4 Hz, 1H), 7.50 (m, 1H), 6.47 (d, J = 1.1 Hz, 1H), 3.94 (s, 3H); ESIMS m/z 303 [(M + H)+]. |
| 1.31 | 185-190 | $^1$H NMR (400 MHz, DMSO) δ 11.79 (s, 1H), 7.94 (s, 2H), 7.55 (m, 1H), 7.52 (m, 1H), 7.40 (d, J = 8.4 Hz, 1H), 6.55 (m, 1H), 3.93 (s, 3H). $^{19}$F NMR (376 MHz, DMSO) δ −132.43. MP 185-190° C. ESIMS m/z 321 [(M + H)+]. |

TABLE 11-continued

Analytical Data for Compounds in Table 1

| C. No. | MP (° C.) | HNMR |
|---|---|---|
| 1.32 | 190-191 | $^1$H NMR (DMSO-d$_6$) δ 3.74 (s, 3H), 3.92 (s, 3H), 6.46 (ddd, J = 3.0, 1.9, 0.9 Hz, 1H), 7.27 (s, 2H), 7.46 (t, J = 2.7 Hz, 1H), 7.56 (d, J = 8.4 Hz, 1H), 7.94 (dd, J = 8.4, 1.5 Hz, 1H), 8.33 (d, J = 1.1 Hz, 1H), 11.26 (d, J = 2.3 Hz, 1H). |
| 1.33 | 154-157 | $^1$H NMR (DMSO-d$_6$) δ 3.75 (s, 3H), 6.41-6.50 (m, 1H), 7.20 (s, 2H), 7.46 (t, J = 2.7 Hz, 1H), 7.56 (d, J = 8.4 Hz, 1H), 7.96 (dd, J = 8.4, 1.5 Hz, 1H), 8.25-8.46 (m, 1H), 11.27 (s, 1H). |
| 1.34 |  | $^1$H NMR (DMSO-d$_6$) δ 3.75 (s, 3H), 3.90 (s, 3H), 6.53 (td, J = 3.2, 1.9 Hz, 1H), 7.37 (d, J = 8.3 Hz, 3H), 7.44-7.54 (m, 2H), 11.71 (s, 1H). |
| 1.35 |  | $^1$H NMR (DMSO-d$_6$) δ 3.77 (s, 3H), 6.53 (td, J = 3.2, 1.9 Hz, 1H), 7.12-7.35 (m, 2H), 7.37 (d, J = 8.3 Hz, 1H), 7.46-7.58 (m, 2H), 11.72 (t, J = 2.2 Hz, 1H), 13.49 (s, 1H). |
| 1.36 |  | $^1$H NMR (DMSO-d$_6$) δ 3.76 (s, 3H), 3.89 (s, 3H), 6.44 (ddd, J = 3.0, 1.8, 0.9 Hz, 1H), 7.32 (d, J = 11.9 Hz, 3H), 7.51 (t, J = 2.8 Hz, 1H), 7.85 (d, J = 6.5 Hz, 1H), 11.30 (s, 1H). |
| 1.37 |  | $^1$H NMR (DMSO-d$_6$) δ 3.75 (s, 3H), 6.43 (ddd, J = 2.9, 1.9, 0.8 Hz, 1H), 7.10-7.46 (m, 3H), 7.50 (t, J = 2.7 Hz, 1H), 7.85 (dd, J = 6.4, 0.8 Hz, 1H), 11.29 (t, J = 2.3 Hz, 1H), 13.48 (s, 1H). |
| 1.38 | 181-182 | $^1$H NMR (400 MHz, DMSO) δ 11.75 (s, 1H), 7.55 (dd, J = 8.3, 6.7 Hz, 1H), 7.50 (m, 1H), 7.38 (d, J = 8.4 Hz, 1H), 7.21 (s, 1H), 6.67 (dd, J = 17.6, 11.5 Hz, 1H), 6.54 (dd, J = 5.1, 3.2 Hz, 1H), 5.48 (ddd, J = 11.4, 7.3, 1.1 Hz, 1H), 3.83 (s, 1H), 3.33 (s, 1H). $^{19}$F NMR (376 MHz, DMSO) δ −132.89. MP 172-173° C. ESIMS m/z 313 [(M + H)+]. |
| 1.39 | 209-211 | $^1$H NMR (400 MHz, DMSO) δ 13.51 (s, 1H), 11.75 (s, 1H), 7.56 (m, 1H), 7.50 (t, J = 2.5 Hz, 1H), 7.38 (d, J = 8.3 Hz, 1H), 7.14 (s, 1H), 6.67 (dd, J = 17.7, 11.5 Hz, 1H), 6.54 (s, 1H), 5.60 (d, J = 17.8 Hz, 1H), 5.49 (d, J = 11.4 Hz, 1H). $^{19}$F NMR (376 MHz, DMSO) δ −132.98. MP: 209-211° C. ESIMS m/z 299 [(M + H)+]. |
| 1.40 | 233-236 | $^1$H NMR (400 MHz, CDCl$_3$) δ 8.27 (s, 1H), 7.51-7.45 (m, 2H), 7.32-7.28 (m, 2H), 6.93-6.79 (m, 1H), 4.90 (s, 2H), 3.98 (s, 3H) |
| 1.41 | 167-169 | $^1$H NMR (400 MHz, CDCl$_3$) δ 7.46 (ddd, J = 7.3, 2.1, 0.8 Hz, 1H), 7.41 (d, J = 8.2 Hz, 1H), 7.33-7.28 (m, 1H), 7.13 (d, J = 3.1 Hz, 1H), 6.79-6.68 (m, 1H), 4.89 (s, 2H), 3.98 (s, 3H), 3.83 (s, 3H) |
| 1.42 | 158-160 | $^1$H NMR (400 MHz, DMSO-d$_6$) δ 7.55 (d, J = 7.5 Hz, 1H), 7.38 (d, J = 3.1 Hz, 1H), 7.32-7.22 (m, 2H), 6.77 (s, 2H), 6.50 (t, J = 2.3 Hz, 1H), 3.84 (s, 3H) |
| 1.43 |  | $^1$H NMR (DMSO-d$_6$) δ 3.88 (s, 3H), 6.61 (dt, J = 3.1, 2.0 Hz, 1H), 6.95 (s, 2H), 7.22-7.35 (m, 2H), 7.49 (t, J = 2.8 Hz, 1H), 11.65 (s, 1H). |
| 1.44 | 116 | $^1$H NMR (DMSO-d$_6$) δ 3.91 (s, 3H), 6.74 (s, 2H), 6.97 (dd, J = 3.2, 1.8 Hz, 1H), 7.28 (d, J = 8.0 Hz, 1H), 7.36 (s, 1H), 7.43 (d, J = 8.0 Hz, 1H), 7.54 (t, J = 2.8 Hz, 1H), 11.65 (s, 1H). |
| 1.45 | 226 | $^1$H NMR (DMSO-d$_6$) δ 3.76 (s, 3H), 3.93 (s, 3H), 7.25 (d, J = 8.1 Hz, 1H), 7.34 (s, 2H), 7.49 (t, J = 2.8 Hz, 1H), 7.59 (dd, J = 3.0, 2.0 Hz, 1H), 7.99 (d, J = 8.2 Hz, 1H), 11.55 (s, 1H). |
| 1.46 |  | $^1$H NMR (DMSO-d$_6$) δ 3.93 (s, 3H), 6.60 (dd, J = 3.2, 2.0 Hz, 1H), 7.03 (s, 2H), 7.24 (d, J = 8.0 Hz, 1H), 7.50 (dd, J = 8.0, 0.9 Hz, 1H), 7.55 (t, J = 2.8 Hz, 1H), 11.44 (s, 1H). |
| 1.47 | 96-100 | $^1$H NMR (300 MHz, CDCl$_3$) δ 11.33 (s, 1H), 7.97 (d, J = 7.7 Hz, 1H), 7.76 (d, J = 7.8 Hz, 1H), 7.37-7.29 (m, 1H), 7.18 (t, J = 7.7 Hz, 1H), 6.65-6.55 (m, 1H), 4.83 (s, 2H), 4.03 (s, 3H) |
| 1.48 | 171-175 | $^1$H NMR (400 MHz, DMSO-d$_6$) δ 11.12 (s, 1H), 7.68 (d, J = 7.8 Hz, 1H), 7.51 (d, J = 7.4 Hz, 1H), 7.41 (t, J = 2.8 Hz, 1H), 7.13 (t, J = 7.6 Hz, 1H), 6.89 (s, 2H), 6.53 (dd, J = 3.0, 2.1 Hz, 1H) |
| 1.49 | 186-188 | $^1$H NMR (DMSO-d$_6$) δ 3.96 (s, 3H), 6.57 (dd, J = 3.2, 2.2 Hz, 1H), 6.81 (s, 2H), 7.23 (d, J = 8.0 Hz, 1H), 7.45 (s, 1H), 7.53 (d, J = 8.1 Hz, 1H), 7.55-7.59 (m, 1H), 11.51 (s, 1H). |
| 1.50 | 147-149 | $^1$H NMR (DMSO-d$_6$) δ 3.78 (s, 3H), 3.94 (s, 3H), 6.60 (dd, J = 3.2, 2.2 Hz, 1H), 7.20 (d, J = 8.1 Hz, 1H), 7.29-7.88 (m, 3H), 8.09 (d, J = 8.2 Hz, 1H), 11.75 (s, 1H). |
| 2.01 | 114-117 | $^1$H NMR (400 MHz, CDCl$_3$) δ 8.16 (t, J = 1.4 Hz, 1H), 7.87 (dt, J = 8.7, 1.8 Hz, 1H), 7.66 (d, J = 2.2 Hz, 1H), 7.61-7.54 (m, 1H), 6.86-6.81 (m, 1H), 4.90 (s, 2H), 4.00 (s, 3H). |
| 2.02 | 165-167 | $^1$H NMR (400 MHz, DMSO-d$_6$) δ 13.60 (s, 1H), 8.13 (s, 1H), 8.07 (d, J = 2.2 Hz, 1H), 7.80 (d, J = 8.7 Hz, 1H), 7.75-7.64 (m, 1H), 7.07 (dd, J = 7.9, 6.5 Hz, 1H), 6.88 (s, 2H). |
| 2.03 | 84-87 | $^1$H NMR (400 MHz, DMSO-d$_6$) δ 3.90 (d, J = 3.3 Hz, 3H), 6.75 (d, J = 19.2 Hz, 2H), 6.92-8.22 (m, 6H) |
| 2.04 | 98 | $^1$H NMR (400 MHz, CDCl$_3$) δ 8.19 (d, J = 7.7 Hz, 1H), 7.63 (d, J = 2.2 Hz, 1H), 7.28 (d, J = 11.2 Hz, 1H), 7.22 (d, J = 2.0 Hz, 1H), 6.79 (dd, J = 2.2, 0.9 Hz, 1H), 4.80 (s, 2H), 4.01 (s, 3H). |
| 2.05 | 160 | $^1$H NMR (400 MHz, CDCl$_3$) δ 8.11 (d, J = 7.4 Hz, 1H), 7.63 (d, J = 2.2 Hz, 1H), 7.29 (d, J = 10.6 Hz, 1H), 6.78 (dd, J = 2.2, 0.9 Hz, 1H), 5.40 (s, 2H), 4.01 (s, 3H), 3.95 (s, 3H). |
| 2.06 |  | $^1$H NMR (400 MHz, CDCl$_3$) δ 8.20 (dd, J = 7.7, 0.8 Hz, 1H), 7.79 (dd, J = 2.1, 0.9 Hz, 1H), 7.69 (d, J = 2.2 Hz, 1H), 7.62 (d, J = 8.2 Hz, 1H), 6.79 (dd, J = 2.1, 1.0 Hz, 1H), 5.32 (s, 2H), 3.95 (s, 3H), 3.93 (s, 3H). |

TABLE 11-continued

Analytical Data for Compounds in Table 1

| C. No. | MP (° C.) | HNMR |
|---|---|---|
| 2.07 | | $^1$H NMR (400 MHz, CDCl$_3$) δ 8.10 (s, 1H), 7.88-7.83 (m, 1H), 7.70 (t, J = 2.5 Hz, 1H), 7.69-7.66 (m, 1H), 6.81 (dd, J = 2.2, 1.0 Hz, 1H), 4.91 (s, 2H), 4.00 (d, J = 1.5 Hz, 3H). |
| 2.08 | 168-170 | $^1$H NMR (400 MHz, DMSO-d$_6$) δ 13.59 (s, 1H), 8.11 (d, J = 2.2 Hz, 1H), 8.03 (s, 1H), 7.77 (s, 2H), 7.04 (dd, J = 2.1, 0.9 Hz, 1H), 6.90 (s, 2H). |
| 2.09 | 151 | $^1$H NMR (400 MHz, CDCl$_3$) δ 7.73 (d, J = 2.1 Hz, 1H), 7.48-7.41 (m, 2H), 6.85 (s, 1H), 4.94 (s, 2H), 3.97 (d, J = 5.6 Hz, 3H). |
| 2.10 | 109 | $^1$H NMR (400 MHz, CDCl$_3$) δ 7.72 (t, J = 3.3 Hz, 2H), 7.34 (dd, J = 9.5, 5.3 Hz, 1H), 6.79 (dd, J = 2.2, 0.9 Hz, 1H), 4.93 (s, 2H), 3.98 (s, 3H). |
| 2.11 | 148 | $^1$H NMR (400 MHz, CDCl$_3$) δ 7.87 (dd, J = 8.2, 6.5 Hz, 1H), 7.71 (d, J = 2.1 Hz, 1H), 7.42 (d, J = 8.2 Hz, 1H), 7.29 (d, J = 1.6 Hz, 1H), 6.82 (dd, J = 3.0, 2.2 Hz, 1H), 4.82 (s, 2H), 4.01 (s, 3H). |
| 2.12 | 130 | $^1$H NMR (400 MHz, CDCl$_3$) δ 8.15 (d, J = 5.7 Hz, 1H), 7.70 (d, J = 2.2 Hz, 1H), 7.35-7.28 (m, 2H), 6.75 (dd, J = 2.2, 0.9 Hz, 1H), 4.80 (s, 2H), 4.01 (s, 3H). |
| 2.13 | 178 | $^1$H NMR (400 MHz, CDCl$_3$) δ 7.82 (dd, J = 8.2, 6.3 Hz, 1H), 7.71 (d, J = 2.1 Hz, 1H), 7.39 (d, J = 8.2 Hz, 1H), 6.84-6.75 (m, 1H), 5.40 (s, 2H), 4.01 (s, 3H), 3.95 (s, 3H). |
| 2.14 | 153 | $^1$H NMR (400 MHz, CDCl$_3$) δ 8.06 (d, J = 5.9 Hz, 1H), 7.70 (t, J = 3.4 Hz, 1H), 7.32 (d, J = 10.6 Hz, 1H), 6.75 (dd, J = 2.2, 0.9 Hz, 1H), 5.39 (s, 2H), 4.01 (s, 3H), 3.96 (s, 3H). |
| 2.15 | 100-103 | $^1$H NMR (400 MHz, CDCl$_3$) δ 7.72-7.69 (m, 1H), 7.68-7.63 (m, 1H), 7.59 (d, J = 8.3 Hz, 1H), 7.42-7.36 (m, 1H), 7.20-7.15 (m, 1H), 4.94 (s, 2H), 4.00 (d, J = 1.5 Hz, 3H). |
| 2.16 | 184-186 | $^1$H NMR (400 MHz, CDCl$_3$) δ 7.76 (d, J = 2.2 Hz, 1H), 7.61 (dd, J = 8.2, 2.1 Hz, 1H), 7.42-7.38 (m, 1H), 7.26-7.24 (m, 1H), 4.96 (s, 2H), 4.00 (s, 3H). |
| 2.17 | 170-173 | $^1$H NMR (400 MHz, DMSO-d$_6$) δ 13.63 (s, 1H), 8.07 (d, J = 2.2 Hz, 1H), 7.72 (d, J = 8.2 Hz, 1H), 7.57 (d, J = 7.5 Hz, 1H), 7.44 (t, J = 7.9 Hz, 1H), 7.09 (s, 1H), 6.93 (s, 2H). |
| 2.18 | | $^1$H NMR (400 MHz, CDCl$_3$) δ 7.81 (d, J = 2.3 Hz, 1H), 7.54 (d, J = 8.0 Hz, 2H), 7.45 (d, J = 8.2 Hz, 1H), 6.96 (s, 1H), 5.20 (s, 2H). |
| 2.19 | 158-159 | $^1$H NMR (400 MHz, DMSO-d$_6$) δ 8.24 (d, J = 2.1 Hz, 1H), 7.68 (d, J = 8.2 Hz, 1H), 7.55 (d, J = 8.2 Hz, 1H), 7.50 (d, J = 2.1 Hz, 1H), 7.37 (s, 1H), 6.83 (s, 2H), 3.93 (s, 3H). |
| 2.20 | | $^1$H NMR (400 MHz, CDCl$_3$) δ 8.22 (d, J = 8.3 Hz, 1H), 7.79 (dd, J = 12.0, 2.1 Hz, 2H), 7.38 (d, J = 8.3 Hz, 1H), 5.61 (s, 2H), 4.05 (s, 3H). |
| 2.21 | | $^1$H NMR (400 MHz, CDCl$_3$) δ 8.22-8.09 (m, 1H), 7.86 (d, J = 2.1 Hz, 1H), 7.77 (d, J = 2.1 Hz, 1H), 7.42-7.34 (m, 1H), 5.39 (s, 2H), 4.04 (s, 3H), 3.95 (s, 3H). |
| 2.22 | 204-206 | $^1$H NMR (400 MHz, DMSO-d$_6$) δ 8.22 (d, J = 2.1 Hz, 1H), 8.20 (d, J = 8.3 Hz, 1H), 8.00 (d, J = 2.1 Hz, 1H), 7.52 (d, J = 8.3 Hz, 1H), 7.42 (s, 1H), 3.78 (s, 3H). |
| 2.23 | 173-174.5 | $^1$H NMR (400 MHz, CDCl$_3$) δ 7.76 (d, J = 2.2 Hz, 1H), 7.61 (dd, J = 8.2, 2.1 Hz, 1H), 7.42-7.38 (m, 1H), 7.26-7.24 (m, 1H), 4.96 (s, 2H), 4.00 (s, 3H). |
| 2.24 | 167 | $^1$H NMR (400 MHz, CDCl$_3$) δ 7.68 (d, J = 2.2 Hz, 1H), 7.54 (d, J = 8.1 Hz, 1H), 7.37-7.34 (m, 1H), 6.93 (d, J = 2.2 Hz, 1H), 4.95 (s, 2H), 3.99 (d, J = 4.7 Hz, 3H). |
| 2.25 | 169 | $^1$H NMR (400 MHz, CDCl$_3$) δ 8.14 (d, J = 8.2 Hz, 1H), 7.75 (d, J = 10.0 Hz, 2H), 7.34 (d, J = 8.3 Hz, 1H), 6.97 (t, J = 8.0 Hz, 1H), 4.86 (s, 2H), 4.02 (s, 3H). |
| 2.26 | 178 | $^1$H NMR (400 MHz, CDCl$_3$) δ 8.09 (d, J = 8.2 Hz, 1H), 7.79 (d, J = 2.1 Hz, 1H), 7.32 (d, J = 8.3 Hz, 1H), 6.92 (d, J = 2.2 Hz, 1H), 5.44 (s, 2H), 4.04 (s, 3H), 3.96 (s, 3H). |
| 3.01 | 50-56 | $^1$H NMR (DMSO-d$_6$) δ 3.89 (s, 3H), 7.09 (s, 2H), 7.52-7.63 (m, 2H), 7.86 (d, J = 5.4 Hz, 1H), 8.07-8.17 (m, 2H). |
| 3.02 | 157-159 | $^1$H NMR (DMSO-d$_6$) δ 6.98 (s, 2H), 7.53-7.61 (m, 2H), 7.84 (d, J = 5.5 Hz, 1H), 8.06-8.13 (m, 2H), 13.70 (s, 1H). |
| 3.03 | 84-85 | $^1$H NMR (400 MHz, DMSO-d$_6$) δ 8.34 (s, 1H), 8.12 (d, J = 8.5 Hz, 1H), 7.87-7.78 (m, 2H), 7.60 (dd, J = 5.5, 0.6 Hz, 1H), 6.95 (s, 2H), 3.90 (s, 3H) |
| 3.04 | 149-150 | $^1$H NMR (400 MHz, DMSO-d$_6$) δ 8.36 (s, 1H), 8.11 (d, J = 8.5 Hz, 1H), 7.83 (t, J = 6.1 Hz, 2H), 7.58 (d, J = 5.4 Hz, 1H), 6.71 (s, 2H); |
| 3.05 | 142-144 | $^1$H NMR (400 MHz, DMSO-d$_6$) δ 8.41 (d, J = 1.7 Hz, 1H), 8.11 (d, J = 8.5 Hz, 1H), 7.82-7.88 (m, 2H), 7.51-7.72 (m, 3H), 7.39 (s, 1H), 3.92 (s, 3H) |
| 3.06 | 155-159 | $^1$H NMR (400 MHz, CDCl$_3$) δ 7.94-7.88 (m, 2H), 7.48 (d, J = 5.4 Hz, 1H), 7.41 (dd, J = 8.3, 1.7 Hz, 1H), 7.36 (dd, J = 5.4, 0.6 Hz, 1H), 4.83 (s, 2H), 3.96 (s, 3H), 2.19 (s, 3H) |
| 3.07 | 159-165 | $^1$H NMR (400 MHz, DMSO-d$_6$) δ 8.10 (d, J = 8.3 Hz, 1H), 7.97 (s, 1H), 7.85 (d, J = 5.4 Hz, 1H), 7.54 (d, J = 5.5 Hz, 1H), 7.44 (d, J = 8.3 Hz, 1H), 6.81 (s, 2H), 2.12 (s, 3H) |
| 3.08 | 125-127 | $^1$H NMR (DMSO-d$_6$) δ 3.76 (s, 3H), 3.92 (s, 3H), 7.40 (s, 2H), 7.60 (dd, J = 5.4, 0.7 Hz, 1H), 7.81 (d, J = 5.4 Hz, 1H), 8.06 (d, J = 8.6 Hz, 1H), 8.24 (dd, J = 8.5, 1.7 Hz, 1H), 8.73 (d, J = 1.5 Hz, 1H). |

TABLE 11-continued

Analytical Data for Compounds in Table 1

| C. No. | MP (° C.) | HNMR |
|---|---|---|
| 3.09 | 137-139 | $^1$H NMR (DMSO-d$_6$) δ 3.76 (s, 3H), 7.31 (s, 2H), 7.59 (d, J = 5.4 Hz, 1H), 7.81 (d, J = 5.4 Hz, 1H), 8.06 (d, J = 8.5 Hz, 1H), 8.26 (dd, J = 8.5, 1.7 Hz, 1H), 8.76 (d, J = 1.5 Hz, 1H), 13.54 (s, 1H). |
| 3.10 | 134-135 | $^1$H NMR (400 MHz, CDCl$_3$) δ 8.22-8.09 (m, 1H), 7.87 (d, J = 8.2 Hz, 1H), 7.66 (dd, J = 8.3, 1.6 Hz, 1H), 7.52 (d, J = 5.5 Hz, 1H), 7.36 (dd, J = 5.5, 0.6 Hz, 1H), 5.34 (s, 2H), 3.97 (s, 3H) |
| 3.11 | 239 (dec) | $^1$H NMR (400 MHz, DMSO-d$_6$) δ 8.22 (d, J = 0.7 Hz, 1H), 7.96 (d, J = 8.2 Hz, 1H), 7.88 (d, J = 5.4 Hz, 1H), 7.59 (dd, J = 8.3, 1.6 Hz, 1H), 7.53 (d, J = 5.4 Hz, 1H), 7.02 (s, 2H) |
| 3.12 | 185-189 | $^1$H NMR (400 MHz, CDCl$_3$) δ 8.48 (s, 1H), 7.95 (dt, J = 8.4, 1.6 Hz, 1H), 7.90 (d, J = 8.3 Hz, 1H), 7.54 (d, J = 5.4 Hz, 1H), 7.37 (d, J = 5.4 Hz, 1H), 4.91 (s, 2H), 4.01 (s, 3H). |
| 3.13 | 165-167 | $^1$H NMR (400 MHz, DMSO-d$_6$) δ 13.60 (s, 1H), 8.45 (d, J = 6.7 Hz, 1H), 7.99 (t, J = 7.0 Hz, 1H), 7.88 (dd, J = 13.5, 6.4 Hz, 2H), 7.52 (t, J = 4.7 Hz, 1H), 6.83 (d, J = 64.9 Hz, 2H). |
| 3.14 | 112 | $^1$H NMR (400 MHz, CDCl$_3$) δ 8.08 (d, J = 6.2 Hz, 1H), 7.60 (d, J = 5.5 Hz, 1H), 7.56 (s, 1H), 7.33 (s, 1H), 4.94 (s, 2H), 3.99 (s, 3H). |
| 3.15 | | $^1$H NMR (400 MHz, CDCl$_3$) δ 8.55-8.44 (m, 1H), 7.92-7.79 (m, 2H), 7.50 (d, J = 5.4 Hz, 1H), 7.34 (dd, J = 5.4, 0.7 Hz, 1H), 7.17 (s, 1H), 4.82 (s, 2H), 4.02 (s, 3H). |
| 3.16 | 176-177 | $^1$H NMR (400 MHz, DMSO-d6) δ 13.51 (s, 1H), 8.60-8.51 (m, 1H), 7.97 (d, J = 8.3 Hz, 1H), 7.91 (dd, J = 8.4, 1.6 Hz, 1H), 7.85 (d, J = 5.4 Hz, 1H), 7.51 (dd, J = 5.4, 0.6 Hz, 1H), 7.35 (s, 1H), 6.69 (s, 2H). |
| 3.17 | 70 | $^1$H NMR (400 MHz, CDCl$_3$) δ 8.53 (d, J = 7.0 Hz, 1H), 7.58 (d, J = 5.5 Hz, 1H), 7.55 (d, J = 7.1 Hz, 1H), 7.52 (s, 1H), 7.29 (d, J = 5.5 Hz, 1H), 4.81 (s, 2H), 4.02 (s, 3H). |
| 3.18 | 143-146 | $^1$H NMR (400 MHz, CDCl$_3$) δ 8.01-7.94 (m, 1H), 7.85 (d, J = 8.2 Hz, 1H), 7.49 (d, J = 5.4 Hz, 1H), 7.43 (dd, J = 8.2, 1.5 Hz, 1H), 7.36 (dd, J = 5.5, 0.6 Hz, 1H), 4.84 (s, 2H), 3.96 (s, 3H), 2.19 (s, 3H) |
| 3.19 | 157-162 | $^1$H NMR (400 MHz, DMSO-d$_6$) δ 8.11 (s, 1H), 7.97 (d, J = 8.2 Hz, 1H), 7.87 (d, J = 5.5 Hz, 1H), 7.54 (d, J = 5.4 Hz, 1H), 7.46 (dd, J = 8.2, 1.5 Hz, 1H), 6.86 (s, 2H), 2.12 (s, 3H) |
| 3.20 | 143-145 | $^1$H NMR (DMSO-d$_6$) δ 3.76 (s, 3H), 3.92 (s, 3H), 7.40 (s, 2H), 7.51 (d, J = 5.5 Hz, 1H), 7.88 (d, J = 5.4 Hz, 1H), 7.95 (d, J = 8.4 Hz, 1H), 8.26 (dd, J = 8.5, 1.5 Hz, 1H), 8.79 (d, J = 1.1 Hz, 1H). |
| 3.21 | 134-136 | $^1$H NMR (DMSO-d$_6$) δ 3.77 (s, 3H), 7.32 (s, 1H), 7.51 (dd, J = 5.4, 0.8 Hz, 1H), 7.88 (d, J = 5.4 Hz, 1H), 7.94 (d, J = 8.4 Hz, 1H), 8.28 (dd, J = 8.4, 1.5 Hz, 1H), 8.81-8.86 (m, 1H). |
| 3.22 | 168 | $^1$H NMR (400 MHz, CDCl$_3$) δ 8.44 (d, J = 6.8 Hz, 1H), 7.58 (t, J = 4.0 Hz, 1H), 7.54-7.52 (m, 1H), 7.30 (d, J = 5.4 Hz, 1H), 5.41 (s, 2H), 4.02 (s, 3H), 3.96 (s, 3H). |
| 3.23 | 219-221 | $^1$H NMR (400 MHz, CDCl$_3$) δ 8.01 (d, J = 1.7 Hz, 1H), 7.85 (ddt, J = 9.5, 7.3, 3.6 Hz, 2H), 7.43-7.33 (m, 2H), 4.93 (s, 2H), 4.02 (s, 3H) |
| 3.24 | 121-123 | $^1$H NMR (400 MHz, CDCl$_3$) δ 7.97-7.85 (m, 2H), 7.54 (d, J = 5.6 Hz, 1H), 7.47 (t, J = 7.7 Hz, 1H), 7.39 (d, J = 5.6 Hz, 1H), 4.96 (s, 2H), 4.04 (s, 3H) |
| 3.25 | 183-185 | $^1$H NMR (300 MHz, DMSO-d$_6$) δ 8.00 (dd, J = 7.9, 0.8 Hz, 1H), 7.87-7.82 (m, 1H), 7.80 (d, J = 5.5 Hz, 1H), 7.56-7.50 (m, 2H), 6.97 (s, 2H) |
| 3.26 | 181-184 | $^1$H NMR (600 MHz, CDCl$_3$) δ 8.05 (d, J = 7.5 Hz, 1H), 7.95 (d, J = 8.0 Hz, 1H), 7.58 (t, J = 7.8 Hz, 1H), 7.56 (s, 1H), 4.98 (s, 2H), 4.05 (s, 3H) |
| 3.27 | | $^1$H NMR (400 MHz, DMSO-d$_6$) δ 7.96 (dd, J = 7.8, 1.0 Hz, 1H), 7.76-7.84 (m, 2H), 7.53 (d, J = 7.7 Hz, 1H), 7.47-7.51 (m, 2H), 6.82 (s, 2H), 3.94 (s, 3H) |
| 4.01 | 188-190 | $^1$H NMR (300 MHz, CDCl$_3$) δ 10.09 (br s, 1H), 8.36 (s, 1H), 8.16 (s, 1H), 8.03 (dt, J = 9, 1.5 Hz, 1H), 7.57 (d, J = 9 Hz, 1H), 4.90 (br s, 2H), 4.00 (s, 3H) |
| 4.02 | 284-287 | $^1$H NMR (300 MHz, DMSO-d$_6$) δ 13.49 (br s, 1H), 13.19 (br s, 1H), 8.28 (s, 1H), 8.21 (s, 1H), 7.89 (dt, J = 9, 1 Hz, 1H), 7.66 (dt, J = 9, 1 Hz, 1H), 6.82 (br s, 2H) |
| 4.03 | 156-159 | $^1$H NMR (400 MHz, CDCl$_3$) δ 8.34 (m, 1H), 8.07 (d, J = 1 Hz, 1H), 8.03 (dt, J = 9, 1.5 Hz, 1H), 7.47 (dt, J = 9, 1 Hz, 1H), 4.89 (br s, 2H), 4.10 (s, 3H), 3.99 (s, 3H) |
| 4.04 | 186-188 | $^1$H NMR (400 MHz, DMSO-d$_6$) δ 13.53 (br s, 1H), 8.28 (s, 1H), 8.19 (s, 1H), 7.92 (d, J = 9 Hz, 1H), 7.75 (d, J = 9 Hz, 1H), 6.81 (br s, 2H), 4.10 (s, 3H) |
| 4.05 | 185-187 | $^1$H NMR (400 MHz, DMSO-d$_6$) δ 13.21 (br s, 1H), 8.16 (s, 1H), 8.01 (s, 1H), 7.88 (dd, J = 9, 1 Hz, 1H), 7.61 (dt, J = 9, 1.5 Hz, 1H), 6.96 (br s, 2H), 3.91 (s, 3H) |
| 4.06 | >300 | $^1$H NMR (400 MHz, DMSO-d$_6$) δ 13.20 (br s, 1H), 8.15 (s, 1H), 8.03 (s, 1H), 7.87 (d, J = 9 Hz, 1H), 7.64 (dt, J = 9, 1.5 Hz, 1H), 6.66 (br s, 2H) |
| 4.07 | 187-190 | $^1$H NMR (400 MHz, CDCl$_3$) δ 8.03 (d, J = 1 Hz, 1H), 8.00 (t, J = 1 Hz, 1H), 7.82 (dd, J = 9, 1 Hz, 1H), 7.72 (m, 1H), 4.94 (br s, 2H), 4.15 (s, 3H), 4.01 (s, 3H) |
| 4.08 | 182-184 | $^1$H NMR (400 MHz, DMSO-d$_6$) δ 13.68 (br s, 1H), 8.14 (d, J = 1 Hz, 1H), 8.06 (s, 1H), 7.89 (dd, J = 9, 0.5 Hz, 1H), 7.62 (dt, J = 9, 1 Hz, 1H), 6.88 (br s, 2H), 4.13 (s, 3H) |

TABLE 11-continued

Analytical Data for Compounds in Table 1

| C. No. | MP (° C.) | HNMR |
|---|---|---|
| 4.09 | 191-193 | $^1$H NMR (400 MHz, DMSO-d$_6$) δ 13.19 (s, 1H), 8.08 (d, J = 21.7 Hz, 2H), 7.84 (d, J = 8.5 Hz, 1H), 7.63 (d, J = 8.5 Hz, 1H), 7.38 (s, 1H), 6.76 (s, 2H), 3.91 (s, 3H) |
| 4.10 | 170-175 | $^1$H NMR (400 MHz, CDCl$_3$) δ 8.42 (s, 1H), 7.63 (dt, J = 5.8, 2.2 Hz, 1H), 7.53-7.45 (m, 2H), 4.96 (s, 2H), 4.12 (s, 3H), 4.01 (s, 3H) |
| 4.11 | 173-175 | $^1$H NMR (400 MHz, DMSO-d$_6$) δ 13.62 (s, 1H), 8.23 (s, 1H), 7.88-7.70 (m, 1H), 7.63-7.45 (m, 2H), 6.93 (s, 2H), 4.11 (d, J = 10.3 Hz, 4H) |
| 4.12 | 212-215 | $^1$H NMR (400 MHz, CDCl$_3$) δ 10.10 (s, 1H), 8.55 (s, 1H), 7.66 (dd, J = 7.2, 1.5 Hz, 1H), 7.59 (d, J = 8.4 Hz, 1H), 7.54-7.45 (m, 1H), 4.97 (s, 2H), 4.02 (s, 3H) |
| 4.13 | 207-210 | $^1$H NMR (400 MHz, CDCl$_3$) δ 12.67 (s, 1H), 8.23 (d, J = 7.5 Hz, 1H), 8.15 (d, J = 1.9 Hz, 1H), 7.89 (d, J = 8.0 Hz, 1H), 7.29 (d, J = 7.7 Hz, 1H), 5.02 (s, 2H), 4.12 (s, 3H) |
| 5.01 |  | $^1$H NMR (400 MHz, CDCl$_3$) δ 8.36 (d, J = 1.5 Hz, 1H), 8.16 (s, 1H), 8.06-7.98 (m, 1H), 7.68 (d, J = 8.6 Hz, 1H), 4.95 (s, 2H), 4.00 (s, 3H). |
| 6.01 | 216 | $^1$H NMR (400 MHz, DMSO-d$_6$) δ 9.48 (s, 1H), 8.49 (s, 1H), 8.30 (d, J = 8.8 Hz, 1H), 7.95 (d, J = 8.5 Hz, 1H), 6.99 (s, 2H), 3.91 (s, 3H) |
| 6.02 | 186-187 | $^1$H NMR (400 MHz, DMSO-d$_6$) δ 13.54 (s, 1H), 9.47 (s, 1H), 8.52 (s, 1H), 8.30 (d, J = 8.5 Hz, 1H), 7.98 (d, J = 8.5 Hz, 1H), 6.91 (s, 2H) |
| 7.01 | 219-221 | $^1$H NMR (300 MHz, DMSO-d$_6$) δ 8.31 (s, 1H), 8.04 (br s, 1H), 7.70 (br s, 2H), 6.92 (br s, 2H), 3.89 (s, 3H) |
| 7.02 | 218-220 | $^1$H NMR (300 MHz, DMSO-d$_6$) δ 8.28 (s, 1H), 7.97 (br s, 1H), 7.75 (d, J = 9 Hz, 1H), 7.68 (dt, J = 9, 1.5 Hz, 1H), 6.94 (br s, 2H), 3.90 (s, 6H) |
| 7.03 | 230-235 dec | $^1$H NMR (300 MHz, DMSO-d$_6$) δ 8.76 (s, 1H), 8.13 (s, 1H), 7.83 (s, 2H), 6.92 (br s, 2H), 3.98 (s, 3H) |
| 8.01 |  | $^1$H NMR (400 MHz, DMSO-d$_6$) δ 8.10 (t, J = 9.8 Hz, 1H), 7.89 (s, 1H), 7.70 (t, J = 8.2 Hz, 1H), 7.08 (s, 2H), 3.94-3.85 (m, 3H), 3.16 (s, 6H) |
| 9.01 | 129-33 | $^1$H NMR (400 MHz, DMSO-d6) δ) 15.84 (s, 1H), 8.35 (s, 1H), 7.98 (s, 2H), 7.41 (s, 1H), 6.79 (s, 2H), 3.91 (s, 3H). |

TABLE 12

Percent Control Rating Conversion Table

| Rating | % Control |
|---|---|
| A | 95-100 |
| B | 85-94 |
| C | 75-84 |
| D | 60-74 |
| E | 45-59 |
| F | 30-44 |
| G | 0-29 |

Example A

Evaluation of Postemergent Herbicidal Activity

Post-Emergent Test I

Seeds test species were obtained from commercial suppliers and planted into a 5"-round pot containing soil-less media mix (metro-mix 360®, Sun Gro Horticulture). Postemergence treatments were planted 8-12 days prior to application and cultured in a greenhouse equipped with supplemental light sources to provide a 16 h photoperiod at 24-29° C. All pots were surface irrigated.

Approximately 10 milligrams (mg) of each compound were dissolved in 1.3 mL acetone-DMSO (97:3, v/v) and diluted with 4.1 mL water-isopropanol-crop oil concentrate (78:20:2, v/v/v) containing 0.02% Triton X-155. Treatments were serial diluted with the above formulation solvent to provide 1.85, 0.926, 0.462 and 0.231 mg/mL of test compound delivered in 2.7 mL/pot (roughly equivalent to 4.0, 2.0, 1.0, and 0.5 kg/ha, respectively).

Formulated compounds were applied using a DeVilbiss® compressed air sprayer at 2-4 psi. Following treatment, pots were returned to the greenhouse for the duration of the experiment. All pots were sub-irrigated as need to provide optimum growing conditions. All pots were fertilized one time per week by subirrigating with Peters Peat-Lite Special fertilizer (20-10-20).

Phytotoxicity ratings were obtained 10 days after treatment postemergence applications. All evaluations were made visually on a scale of 0 to 100 where 0 represents no activity and 100 represents complete plant death. Visual assessments of plant injury were made based on growth reduction, discoloration, leaf deformity and necrosis Some of the compounds tested, application rates employed, plant species tested, and results are given in Table 13.

TABLE 13

Post-emergent Test I Herbicidal Activity on Key Broadleaf and Grass Weed as well as Crop Species

| Compound Number | Application Rate (Kg ai/ha) | Visual Growth Reduction (%) 10 Days After Application | | | | |
|---|---|---|---|---|---|---|
| | | AVEFA | ECHCG | HELAN | IPOHE | SETFA |
| 1.10 | 3.96 | G | G | A | F | G |
| 1.48 | 4 | G | G | C | n/a | G |
| 3.05 | 4 | C | A | B | B | A |

AVEFA: wild oats (*Avena fatua*)
ECHCG: barnyardgrass (*Echinochloa crus-galli*)
HELAN: sunflower (*Helianthus annuus*)
IPOHE: ivyleaf morningglory (*Ipomoea hederecea*)
SETFA: giant foxtail (*Setaria faberi*)
g ai/ha: grams active ingredient per hectare

Example B

Evaluation of Preemergent Herbicidal Activity

Pre-Emergent Test I

Seeds of test species were planted into round plastic pots (5-inch diameter) containing sandy loam soil. After planting, all pots were sub-irrigated 16 h prior to compound application.

Compounds were dissolved in a 97:3 v/v (volume/volume) mixture of acetone and dimethyl sulfoxide (DMSO) and diluted to the appropriate concentration in a final application solution containing water, acetone, isopropanol, DMSO and Agri-dex (crop oil concentrate) in a 59:23:15:1.0:1.5 v/v ratio and 0.02% w/v (weight/volume) of Triton X-155 to obtain the spray solution containing the highest application rate. The high application rate was serial diluted with the above application solution to provide delivery of the compound at rates 1/2×, 1/4× and 1/8× of the highest rate (equivalent to 4.0, 2.0, 1.0, and 0.5 kg/ha, respectively).

Formulated compound (2.7 mL) was applied pipetted evenly over the soil surface followed by incorporation with water (15 mL). Following treatment, pots were returned to the greenhouse for the duration of the experiment. The greenhouse was programmed for an approximate 15 h photoperiod which was maintained at about 23-29° C. during the day and 22-28° C. during the night. Nutrients and water were added on a regular basis through surface irrigation and supplemental lighting was provided with overhead metal halide 1000-Watt lamps as necessary.

Herbicidal effect ratings were obtained 14 days after treatment. All evaluations were made relative to appropriate controls on a scale of 0 to 100 where 0 represents no herbicidal effect and 100 represents plant death or lack of emergence from the soil. Some of the compounds tested, application rates employed, plant species tested, and results are given in Table 14.

TABLE 14

Pre-emergent Test I Herbicidal Activity on Key Broadleaf and Grass Weed as well as Crop Species

| Compound Number | Application Rate (Kg ai/ha) | AVEFA | ECHCG | HELAN | IPOHE | SETFA |
|---|---|---|---|---|---|---|
| 1.10 | 3.96 | G | F | G | G | G |
| 1.48 | 4 | G | G | C | D | G |
| 3.05 | 4 | F | A | F | A | A |

AVEFA: wild oats (*Avena fatua*)
ECHCG: barnyardgrass (*Echinochloa crs-galli*)
HELAN: sunflower (*Helianthus annuus*)
IPOHE: ivyleaf morningglory (*Ipomoea hederecea*)
SETFA: giant foxtail (*Setaria faberi*)
g ai/ha: grams active ingredient per hectare

Example C

Evaluation of Postemergent Herbicidal Activity

Post-Emergent Test II:

Seeds or nutlets of the desired test plant species were planted in Sun Gro Metro-Mix 360 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 d in a greenhouse with an approximate 15 h photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain 1/2×, 1/4×, 1/8× and 1/16× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Tables 15 and 16.

TABLE 15

Post-emergent Test II Herbicidal Activity on Key Broadleaf Weed and Crop Species

| C. No. | Application Rate (g ai/ha) | Visual Growth Reduction (%) 14 Days After Application | | | | | |
|---|---|---|---|---|---|---|---|
| | | ABUTH | AMARE | BRSNN | CHEAL | EPHHL | HELAN |
| 1.01 | 35 | G | n/a | G | G | A | G |
| | 70 | G | G | G | G | A | C |
| | 140 | F | E | G | G | A | C |
| 1.02 | 35 | G | n/a | G | C | E | E |
| | 70 | G | B | G | B | E | D |
| | 140 | G | B | G | A | D | D |
| 1.03 | 35 | G | n/a | G | B | A | G |
| | 70 | G | n/a | G | B | A | G |
| | 140 | C | B | G | A | B | E |
| 1.04 | 35 | E | D | F | E | A | E |
| | 70 | G | D | E | D | A | E |
| | 140 | G | D | E | D | A | B |
| 1.05 | 35 | E | D | F | B | F | A |
| | 70 | A | C | E | A | F | A |
| | 140 | B | A | D | A | E | A |

TABLE 15-continued

Post-emergent Test II Herbicidal Activity on Key Broadleaf Weed and Crop Species

| C. No. | Application Rate (g ai/ha) | ABUTH | AMARE | BRSNN | CHEAL | EPHHL | HELAN |
|---|---|---|---|---|---|---|---|
| 1.06 | 35 | G | A | C | B | G | G |
|  | 70 | G | B | B | A | G | G |
|  | 140 | G | C | B | A | G | G |
| 1.07 | 35 | G | B | G | B | D | A |
|  | 70 | G | A | G | B | D | A |
|  | 140 | G | A | G | B | D | A |
| 1.08 | 35 | B | A | E | A | A | B |
|  | 70 | A | A | C | A | A | A |
|  | 140 | A | A | B | A | A | A |
| 1.09 | 35 | A | A | A | A | B | A |
|  | 70 | A | A | A | A | A | A |
|  | 140 | A | A | A | A | A | A |
| 1.10 | 35 | G | G | G | A | G | G |
|  | 70 | G | B | G | A | G | G |
|  | 140 | G | A | G | A | G | E |
| 1.13 | 35 | G | G | G | D | G | E |
|  | 70 | G | F | G | C | G | D |
|  | 140 | G | F | F | B | F | D |
| 1.14 | 35 | G | C | E | D | G | D |
|  | 70 | G | B | D | D | G | C |
|  | 140 | G | B | C | C | D | C |
| 1.15 | 35 | A | A | C | A | A | A |
|  | 70 | A | A | A | A | A | A |
|  | 140 | A | A | A | A | A | A |
| 1.16 | 35 | B | A | A | A | A | A |
|  | 70 | A | A | A | A | A | A |
|  | 140 | A | A | A | A | A | B |
| 1.17 | 35 | E | A | A | A | A | A |
|  | 70 | E | A | A | A | A | A |
|  | 140 | D | A | A | A | A | A |
| 1.19 | 35 | A | A | A | A | A | D |
|  | 70 | A | A | A | A | A | C |
|  | 140 | A | A | A | A | A | A |
| 1.20 | 35 | E | C | A | A | A | A |
|  | 70 | D | B | A | A | A | A |
|  | 140 | D | A | A | A | A | A |
| 1.21 | 35 | D | G | G | E | C | E |
|  | 70 | D | G | G | B | B | C |
|  | 140 | D | E | D | B | A | C |
|  | 140 | G | G | G | G | G | G |
| 1.22 | 35 | G | C | E | G | E | C |
|  | 70 | G | C | D | G | C | B |
|  | 140 | G | B | D | G | B | B |
| 1.23 | 35 | A | A | D | A | A | D |
|  | 70 | A | A | C | A | A | C |
|  | 140 | A | A | B | A | A | B |
| 1.24 | 35 | B | A | B | B | A | D |
|  | 70 | A | A | E | A | A | C |
|  | 140 | A | A | A | A | B | B |
| 1.25 | 35 | G | C | D | G | G | G |
|  | 70 | G | B | C | D | G | G |
|  | 140 | F | A | B | D | F | G |
| 1.26 | 35 | G | C | B | G | G | G |
|  | 70 | G | B | A | F | F | G |
|  | 140 | G | A | A | F | E | G |
| 1.27 | 35 | D | D | B | B | A | G |
|  | 70 | B | A | A | B | A | G |
|  | 140 | B | A | A | B | A | G |
| 1.28 | 35 | B | G | C | E | G | A |
|  | 70 | B | G | B | D | G | A |
|  | 140 | A | D | B | D | G | A |
| 1.29 | 35 | G | E | C | E | G | D |
|  | 70 | G | G | C | E | G | D |
|  | 140 | G | G | B | C | G | C |
| 1.30 | 35 | G | G | E | F | G | G |
|  | 70 | G | C | E | F | E | G |
|  | 140 | C | D | D | E | D | G |
| 1.31 | 35 | E | D | B | A | A | F |
|  | 70 | D | A | A | A | A | E |
|  | 140 | D | A | A | A | A | D |
| 1.32 | 35 | G | G | F | G | G | E |
|  | 70 | G | F | E | G | D | D |
|  | 140 | G | D | D | C | B | C |
| 1.33 | 35 | G | D | A | G | E | D |
|  | 70 | G | D | A | E | D | D |
|  | 140 | G | C | A | D | C | C |
| 1.34 | 35 | G | G | C | G | G | B |
|  | 70 | G | G | B | E | G | A |
|  | 140 | G | F | A | D | D | A |
| 1.35 | 35 | G | C | A | G | C | F |
|  | 70 | G | B | A | G | C | D |
|  | 140 | G | A | A | B | B | A |
| 1.37 | 35 | G | G | F | G | G | G |
|  | 70 | G | G | D | G | G | G |
|  | 140 | G | G | C | G | G | G |
| 1.39 | 35 | G | A | C | A | B | G |
|  | 70 | G | A | B | C | C | G |
| 1.40 | 35 | G | n/a | G | G | G | G |
|  | 70 | G | A | G | G | G | F |
|  | 140 | G | n/a | G | G | G | E |
| 1.43 | 35 | G | A | G | C | G | D |
|  | 70 | G | A | G | B | G | C |
|  | 140 | D | A | G | B | F | C |
| 1.44 | 35 | G | B | G | B | E | G |
|  | 70 | C | A | G | B | C | G |
|  | 140 | B | A | F | A | B | G |
| 1.45 | 35 | G | G | G | G | G | G |
|  | 70 | G | G | G | G | G | G |
|  | 140 | G | E | G | G | G | F |
| 1.46 | 35 | G | G | G | C | G | G |
|  | 70 | G | G | G | B | G | F |
|  | 140 | G | D | G | A | G | E |
| 1.47 | 35 | G | G | G | C | G | G |
|  | 70 | G | G | G | C | G | G |
|  | 140 | G | F | G | B | G | E |
| 1.48 | 140 | G | G | G | D | G | C |
| 1.49 | 35 | B | G | G | B | G | G |
|  | 70 | B | F | G | B | G | G |
|  | 140 | B | G | G | A | G | E |
| 2.02 | 35 | E | C | G | A | C | C |
|  | 70 | B | A | F | A | A | B |
|  | 140 | B | A | F | A | A | A |
| 2.03 | 35 | A | D | G | B | E | G |
|  | 70 | A | B | G | A | C | D |
|  | 140 | A | B | G | A | C | C |
|  | 280 | A | A | F | A | B | B |
| 2.04 | 35 | C | A | G | A | A | G |
|  | 70 | B | A | G | A | A | G |
|  | 140 | A | A | F | A | A | F |
| 2.05 | 35 | G | B | G | G | F | G |
|  | 70 | G | C | G | G | F | G |
|  | 140 | G | A | G | E | E | F |
| 2.06 | 35 | G | C | F | D | F | D |
|  | 70 | G | A | D | C | C | C |
|  | 140 | C | A | B | B | A | B |
| 2.09 | 35 | B | B | D | A | A | D |
|  | 70 | B | A | C | A | A | C |
|  | 140 | B | A | B | A | A | B |
| 2.10 | 35 | D | B | F | B | A | C |
|  | 70 | D | A | D | A | A | B |
|  | 140 | B | A | C | B | A | A |
| 2.11 | 35 | A | A | C | A | A | E |
|  | 70 | A | A | B | A | A | D |
|  | 140 | A | A | A | A | A | C |
| 2.12 | 35 | B | A | C | A | A | F |
|  | 70 | A | A | B | A | A | D |
|  | 140 | A | A | A | A | A | D |
| 2.13 | 35 | A | D | A | A | A | C |
|  | 70 | A | A | A | A | A | B |
|  | 140 | A | A | A | A | A | A |

TABLE 15-continued

Post-emergent Test II Herbicidal Activity on Key Broadleaf Weed and Crop Species

| C. No. | Application Rate (g ai/ha) | Visual Growth Reduction (%) 14 Days After Application | | | | | |
|---|---|---|---|---|---|---|---|
| | | ABUTH | AMARE | BRSNN | CHEAL | EPHHL | HELAN |
| 2.14 | 35 | G | A | A | B | B | D |
| | 70 | G | A | A | A | A | B |
| | 140 | G | A | A | A | A | A |
| 2.15 | 35 | E | A | E | A | G | E |
| | 70 | C | A | C | A | G | C |
| | 140 | A | A | B | A | G | C |
| 2.16 | 35 | B | A | E | A | G | A |
| | 70 | A | A | D | A | G | A |
| | 140 | A | A | D | A | G | A |
| 2.17 | 140 | C | A | C | A | A | B |
| 2.18 | 35 | G | A | E | B | G | C |
| | 70 | G | A | D | B | G | C |
| | 140 | G | A | D | B | G | B |
| 2.19 | 35 | A | A | G | A | G | G |
| | 70 | A | A | D | A | G | C |
| | 140 | A | A | D | A | G | C |
| 2.20 | 35 | E | A | G | B | G | B |
| | 70 | D | A | G | A | G | A |
| | 140 | D | A | F | A | G | A |
| 2.21 | 35 | F | A | F | B | G | D |
| | 70 | D | A | F | B | G | C |
| | 140 | D | A | E | A | G | C |
| 2.22 | 35 | F | A | G | A | G | C |
| | 70 | F | A | E | A | G | B |
| | 140 | E | A | D | A | G | A |
| 2.23 | 35 | G | A | G | A | G | B |
| | 70 | G | A | G | A | G | A |
| | 140 | G | A | G | A | G | A |
| 2.24 | 35 | C | A | D | A | D | C |
| | 70 | C | A | C | A | C | C |
| | 140 | A | A | C | A | C | B |
| 2.25 | 35 | C | A | G | A | G | G |
| | 70 | C | A | E | A | C | F |
| | 140 | A | A | C | A | B | B |
| 2.26 | 35 | E | A | E | A | E | C |
| | 70 | D | A | D | A | D | A |
| | 140 | D | A | D | A | C | A |
| 3.01 | 35 | D | B | G | A | G | C |
| | 70 | D | A | G | A | G | C |
| | 140 | C | A | G | A | G | B |
| 3.02 | 35 | G | A | G | B | G | D |
| | 70 | G | A | G | B | G | C |
| | 140 | G | A | G | B | G | B |
| 3.03 | 35 | A | A | G | A | A | A |
| | 70 | A | A | D | A | A | A |
| | 140 | A | A | D | A | A | A |
| 3.05 | 35 | B | F | G | C | D | G |
| | 70 | B | E | G | B | D | G |
| | 140 | A | D | G | B | C | F |
| | 140 | E | A | A | A | G | B |
| | 280 | A | B | G | B | B | E |
| 3.06 | 35 | E | B | F | F | G | A |
| | 70 | D | B | F | D | G | A |
| | 140 | B | A | E | D | F | A |
| 3.07 | 35 | G | G | E | G | G | B |
| | 70 | G | D | D | G | G | B |
| | 140 | G | C | D | C | G | B |
| 3.08 | 35 | G | G | G | B | D | D |
| | 70 | F | F | G | B | C | C |
| | 140 | F | D | F | B | B | B |
| 3.09 | 35 | G | F | E | B | A | D |
| | 70 | G | C | B | B | A | C |
| | 140 | E | B | A | A | A | B |
| 3.10 | 35 | G | A | G | C | G | B |
| | 70 | G | A | G | C | G | B |
| | 140 | G | A | G | C | G | B |
| 3.11 | 35 | G | n/a | G | B | G | B |
| | 70 | G | n/a | G | B | G | B |
| | 140 | G | n/a | G | B | G | B |
| 3.12 | 35 | D | D | G | A | D | B |
| | 70 | A | D | G | A | D | B |
| | 140 | A | B | F | A | B | B |
| 3.13 | 35 | G | A | G | B | G | B |
| | 70 | G | A | G | A | G | B |
| | 140 | C | A | D | A | D | B |
| 3.14 | 35 | G | B | G | B | F | B |
| | 70 | G | A | G | B | F | B |
| | 140 | G | A | G | A | D | A |
| 3.15 | 35 | B | A | F | B | C | D |
| | 70 | A | A | E | B | C | D |
| | 140 | A | A | E | A | B | B |
| 3.16 | 35 | D | B | G | B | D | G |
| | 70 | D | A | G | B | D | G |
| | 140 | C | B | E | B | D | G |
| 3.17 | 35 | G | C | G | B | E | G |
| | 70 | E | A | G | A | D | G |
| | 140 | D | A | D | A | C | F |
| 3.18 | 35 | D | D | G | F | E | A |
| | 70 | C | C | G | D | G | A |
| | 140 | C | A | G | D | F | A |
| 3.19 | 35 | G | D | G | D | G | B |
| | 70 | G | A | G | D | G | B |
| | 140 | D | C | G | C | G | B |
| 3.20 | 35 | G | G | F | B | C | C |
| | 70 | G | D | D | A | A | B |
| | 140 | G | D | D | A | A | B |
| 3.21 | 35 | G | A | C | B | C | D |
| | 70 | F | A | B | B | B | D |
| | 140 | E | A | A | A | A | C |
| 3.22 | 35 | G | D | G | D | A | C |
| | 70 | G | A | F | C | A | B |
| | 140 | G | A | D | B | A | B |
| 3.23 | 35 | G | G | G | G | G | G |
| | 70 | G | G | G | E | G | G |
| | 140 | G | G | G | B | G | G |
| 3.24 | 35 | G | B | E | B | G | D |
| | 70 | G | B | E | A | G | D |
| | 140 | G | A | E | A | G | B |
| 3.25 | 140 | G | A | C | A | G | E |
| 3.27 | 35 | G | B | E | C | G | E |
| | 70 | G | A | D | B | G | D |
| | 140 | E | A | D | A | G | C |
| | 280 | C | A | B | A | G | B |
| 4.01 | 35 | G | G | G | G | G | G |
| | 70 | G | E | G | D | G | G |
| | 140 | G | D | G | D | G | G |
| 4.03 | 35 | G | G | G | A | E | G |
| | 70 | G | E | G | A | D | E |
| | 140 | G | C | G | A | C | D |
| 4.05 | 35 | G | G | G | B | D | D |
| | 70 | G | A | G | B | A | D |
| | 140 | E | A | E | A | A | A |
| 4.06 | 35 | G | C | D | G | E | E |
| | 70 | G | A | C | E | D | D |
| | 140 | G | A | B | A | B | C |
| 4.07 | 140 | E | n/a | E | G | D | A |
| 4.08 | 140 | G | n/a | D | A | G | B |
| 4.09 | 35 | G | G | G | E | G | G |
| | 70 | G | E | G | C | G | F |
| | 140 | G | B | D | B | G | E |
| 4.10 | 35 | G | G | G | G | G | G |
| | 70 | G | A | G | G | G | G |
| | 140 | G | A | G | G | G | E |
| 4.13 | 35 | G | n/a | G | G | G | G |
| | 70 | G | n/a | G | G | G | G |
| | 140 | G | n/a | G | D | G | G |
| 5.01 | 35 | D | C | B | D | n/a | B |
| | 70 | D | B | A | B | A | B |
| | 140 | D | B | A | B | n/a | A |

TABLE 15-continued

Post-emergent Test II Herbicidal Activity on Key Broadleaf Weed and Crop Species

| C. No. | Application Rate (g ai/ha) | ABUTH | AMARE | BRSNN | CHEAL | EPHHL | HELAN |
|---|---|---|---|---|---|---|---|
| 6.01 | 35 | B | B | A | A | G | B |
|  | 70 | B | A | A | A | B | B |
|  | 140 | B | A | A | A | A | B |
| 6.02 | 35 | B | A | A | A | A | A |
|  | 70 | B | A | A | A | A | A |
|  | 140 | B | A | A | A | A | A |
| 7.02 | 35 | G | G | G | G | G | G |
|  | 70 | G | G | G | C | G | G |
|  | 140 | G | G | G | A | G | G |
| 8.01 | 35 | G | G | G | G | G | G |
|  | 70 | G | G | G | G | G | G |
|  | 70 | A | E | G | B | A | A |
|  | 140 | G | G | G | G | G | G |
|  | 140 | A | D | G | A | A | A |

ABUTH: velvetleaf (*Abutilon theophrasti*)
AMARE: redroot pigweed (*Amaranthus retroflexus*)
BRSNN: oilseed rape, canola (*Brassica napus*)
CHEAL: lambsquarters (*Chenopodium album*)
EPHHL: wild poinsettia (*Euphorbia heterophylla*)
HELAN: sunflower (*Helianthus annuus*)
g ai/ha: grams active ingredient per hectare

TABLE 16

Post-emergent Test II Herbicidal Activity on Key Grass and Sedge Weeds as well as Grass Crops

| C. No. | Application Rate (g ai/ha) | CYPES | ECHCG | SETFA | ORYSA | TRZAS | ZEAMX |
|---|---|---|---|---|---|---|---|
| 1.01 | 35 | G | G | G | G | G | G |
|  | 70 | G | n/a | G | G | G | A |
|  | 140 | G | C | G | G | G | B |
| 1.02 | 35 | G | G | G | G | G | G |
|  | 70 | G | G | G | G | G | G |
|  | 140 | G | E | G | G | G | G |
| 1.03 | 35 | G | G | G | G | G | G |
|  | 70 | G | G | G | G | G | G |
|  | 140 | G | D | G | G | G | G |
| 1.04 | 35 | G | G | G | G | G | G |
|  | 70 | G | n/a | G | G | G | G |
|  | 140 | G | B | G | G | G | G |
| 1.05 | 35 | G | G | F | G | G | G |
|  | 70 | G | G | E | G | F | F |
|  | 140 | G | D | D | G | E | E |
| 1.06 | 35 | G | G | G | G | G | G |
|  | 70 | G | D | G | G | G | G |
|  | 140 | G | C | G | G | G | G |
| 1.07 | 35 | G | G | D | G | G | G |
|  | 70 | G | G | C | G | G | G |
|  | 140 | G | G | C | G | G | G |
| 1.08 | 35 | G | B | G | G | G | E |
|  | 70 | G | A | D | G | G | C |
|  | 140 | G | A | C | G | F | B |
| 1.09 | 35 | F | A | B | G | G | D |
|  | 70 | C | A | B | G | G | C |
|  | 140 | B | A | B | G | G | C |
| 1.10 | 35 | G | G | G | G | G | G |
|  | 70 | G | G | G | G | G | G |
|  | 140 | G | G | G | G | G | G |
| 1.12 | 35 | G | G | C | G | E | G |
|  | 70 | G | G | D | G | G | G |
|  | 140 | G | B | C | G | G | G |

TABLE 16-continued

Post-emergent Test II Herbicidal Activity on Key Grass and Sedge Weeds as well as Grass Crops

| C. No. | Application Rate (g ai/ha) | CYPES | ECHCG | SETFA | ORYSA | TRZAS | ZEAMX |
|---|---|---|---|---|---|---|---|
| 1.13 | 35 | G | G | G | G | G | G |
|  | 70 | G | G | G | G | G | G |
|  | 140 | G | G | G | G | G | G |
| 1.14 | 35 | G | G | G | G | G | G |
|  | 70 | G | G | G | G | G | G |
|  | 140 | G | G | G | G | G | G |
| 1.15 | 35 | G | C | D | G | E | G |
|  | 70 | D | B | D | G | D | F |
|  | 140 | E | A | B | F | D | D |
| 1.16 | 35 | G | C | D | F | F | G |
|  | 70 | D | B | C | D | D | F |
|  | 140 | B | A | B | D | D | D |
| 1.17 | 35 | E | B | C | G | D | D |
|  | 70 | E | B | B | G | D | C |
|  | 140 | E | B | B | G | D | C |
| 1.19 | 35 | B | B | D | F | D | D |
|  | 70 | C | B | C | E | C | D |
|  | 140 | A | A | B | D | C | B |
| 1.20 | 35 | G | G | E | G | G | F |
|  | 70 | G | D | C | G | E | E |
|  | 140 | G | C | B | G | D | D |
| 1.21 | 35 | G | G | n/a | G | G | G |
|  | 70 | G | G | n/a | G | G | G |
|  | 140 | G | G | n/a | G | G | G |
|  | 140 | G | C | G | G | G | G |
| 1.22 | 35 | G | G | G | G | G | G |
|  | 70 | G | G | D | G | G | G |
|  | 140 | G | G | B | G | G | G |
| 1.23 | 35 | G | G | G | G | G | G |
|  | 70 | G | G | G | G | G | G |
|  | 140 | G | D | D | G | F | G |
| 1.24 | 35 | G | G | G | G | G | G |
|  | 70 | G | G | E | G | F | G |
|  | 140 | G | G | D | G | E | G |
| 1.25 | 35 | G | G | G | G | G | G |
|  | 70 | G | G | G | G | G | G |
|  | 140 | G | G | G | G | G | G |
| 1.26 | 35 | G | G | G | G | G | G |
|  | 70 | G | G | G | G | G | G |
|  | 140 | G | G | G | G | G | G |
| 1.27 | 35 | G | G | G | G | G | G |
|  | 70 | G | G | G | G | G | G |
|  | 140 | G | G | G | G | G | G |
| 1.28 | 35 | G | G | G | G | G | G |
|  | 70 | G | G | G | G | F | G |
|  | 140 | G | G | G | G | F | G |
| 1.29 | 35 | G | G | G | G | G | G |
|  | 70 | G | G | G | G | G | G |
|  | 140 | F | G | G | G | G | G |
| 1.30 | 35 | G | G | G | G | G | G |
|  | 70 | G | G | G | G | G | G |
|  | 140 | G | G | G | G | G | G |
| 1.31 | 35 | G | C | D | G | C | G |
|  | 70 | G | C | C | G | G | G |
|  | 140 | G | B | B | G | F | G |
| 1.32 | 35 | G | G | G | G | G | G |
|  | 70 | G | G | G | G | G | G |
|  | 140 | G | G | G | G | G | G |
| 1.33 | 35 | G | G | G | G | G | n/a |
|  | 70 | G | G | G | G | G | n/a |
|  | 140 | G | G | G | G | F | n/a |
| 1.34 | 35 | G | G | G | G | G | G |
|  | 70 | G | G | G | G | G | G |
|  | 140 | G | G | D | G | F | G |
| 1.35 | 35 | G | G | G | G | G | G |
|  | 70 | G | G | G | G | F | G |
|  | 140 | G | G | G | G | E | G |
| 1.37 | 35 | G | G | G | G | G | G |
|  | 70 | G | G | G | G | G | G |
|  | 140 | G | G | G | G | G | G |

TABLE 16-continued

Post-emergent Test II Herbicidal Activity on Key Grass and Sedge Weeds as well as Grass Crops

| C. No. | Application Rate (g ai/ha) | CYPES | ECHCG | SETFA | ORYSA | TRZAS | ZEAMX |
|---|---|---|---|---|---|---|---|
| 1.39 | 35 | G | G | G | G | G | G |
|  | 70 | G | G | G | G | G | G |
| 1.40 | 35 | G | G | G | G | G | G |
|  | 70 | G | G | G | G | G | G |
|  | 140 | G | G | G | G | G | G |
| 1.43 | 35 | G | G | G | G | G | G |
|  | 70 | G | G | G | G | G | G |
|  | 140 | G | G | G | G | G | G |
| 1.44 | 35 | G | G | G | G | G | G |
|  | 70 | G | G | G | G | G | G |
|  | 140 | G | G | G | G | G | G |
| 1.45 | 35 | G | G | G | G | G | G |
|  | 70 | G | G | G | G | G | G |
|  | 140 | G | G | G | G | G | G |
| 1.46 | 35 | G | G | G | G | G | G |
|  | 70 | G | G | G | G | G | G |
|  | 140 | G | G | G | G | G | G |
| 1.47 | 35 | G | G | G | G | G | G |
|  | 70 | G | G | G | G | G | G |
|  | 140 | G | G | G | G | G | G |
| 1.48 | 140 | G | G | G | G | G | G |
|  | 35 | G | G | G | G | G | G |
|  | 70 | G | G | G | G | G | G |
|  | 140 | G | G | G | G | G | G |
| 2.02 | 35 | G | B | D | G | G | A |
|  | 70 | G | B | D | G | F | A |
|  | 140 | G | A | C | G | E | A |
| 2.03 | 35 | G | F | G | G | G | G |
|  | 70 | G | D | G | G | G | G |
|  | 140 | G | B | F | G | G | G |
|  | 280 | G | A | F | G | G | D |
| 2.04 | 35 | G | D | D | G | G | D |
|  | 70 | G | A | C | G | F | C |
|  | 140 | F | A | B | G | E | B |
| 2.05 | 35 | G | G | G | G | G | G |
|  | 70 | G | G | G | G | G | G |
|  | 140 | G | G | G | G | G | G |
| 2.06 | 35 | G | G | G | G | G | G |
|  | 70 | G | E | G | G | G | G |
|  | 140 | G | A | G | G | G | G |
| 2.08 | 35 | G | B | E | G | G | E |
|  | 70 | G | B | D | F | G | D |
|  | 140 | G | A | B | F | G | D |
| 2.09 | 35 | G | D | E | G | G | E |
|  | 70 | G | B | D | F | G | D |
|  | 140 | G | B | D | F | G | D |
| 2.10 | 35 | G | D | D | G | G | G |
|  | 70 | G | D | D | F | F | F |
|  | 140 | F | B | C | F | D | E |
| 2.11 | 35 | G | B | E | G | G | E |
|  | 70 | G | A | D | G | G | D |
|  | 140 | F | A | C | G | F | B |
| 2.12 | 35 | G | A | E | G | G | G |
|  | 70 | G | A | D | G | F | F |
|  | 140 | G | A | D | G | G | D |
| 2.13 | 35 | F | C | G | G | G | G |
|  | 70 | B | A | E | F | E | F |
|  | 140 | B | A | D | F | E | E |
| 2.14 | 35 | G | G | G | G | G | G |
|  | 70 | G | G | G | G | G | G |
|  | 140 | G | C | G | G | G | G |
| 2.15 | 35 | G | G | G | G | G | A |
|  | 70 | G | E | G | G | G | A |
|  | 140 | G | C | G | G | G | A |
| 2.16 | 35 | G | G | G | G | G | E |
|  | 70 | G | G | G | G | G | A |
|  | 140 | G | G | G | G | G | A |
| 2.17 | 140 | A | C | G | G | G | F |
| 2.18 | 35 | G | G | G | G | G | G |
|  | 70 | G | G | G | G | G | G |
|  | 140 | G | G | G | G | G | G |
| 2.19 | 35 | G | G | n/a | G | G | G |
|  | 70 | G | G | n/a | G | G | G |
|  | 140 | G | G | n/a | G | G | G |
| 2.20 | 35 | G | n/a | G | G | G | G |
|  | 70 | G | n/a | F | G | G | G |
|  | 140 | G | n/a | D | G | G | G |
| 2.21 | 35 | G | n/a | G | G | G | G |
|  | 70 | G | n/a | G | G | G | G |
|  | 140 | G | n/a | G | G | G | G |
| 2.22 | 35 | G | G | G | G | G | G |
|  | 70 | G | G | G | G | G | G |
|  | 140 | G | G | G | G | G | G |
| 2.23 | 35 | G | G | G | G | G | G |
|  | 70 | G | G | G | G | G | G |
|  | 140 | G | G | G | G | G | G |
| 2.24 | 35 | D | G | G | G | G | G |
|  | 70 | C | G | G | G | G | F |
|  | 140 | B | G | G | G | G | D |
| 2.25 | 35 | G | G | G | G | G | G |
|  | 70 | F | G | G | G | G | G |
|  | 140 | C | G | G | G | G | E |
| 2.26 | 35 | G | G | G | G | G | G |
|  | 70 | G | G | G | G | G | G |
|  | 140 | G | G | G | G | G | G |
| 3.01 | 35 | G | G | G | G | G | G |
|  | 70 | G | G | G | G | G | E |
|  | 140 | G | G | G | G | G | D |
| 3.02 | 35 | G | G | G | G | G | G |
|  | 70 | G | G | G | G | G | D |
|  | 140 | G | G | G | G | G | D |
| 3.03 | 35 | E | B | G | G | G | A |
|  | 70 | E | A | B | G | F | A |
|  | 140 | E | A | B | G | E | A |
| 3.05 | 35 | G | E | G | G | G | G |
|  | 70 | G | C | G | G | G | G |
|  | 140 | G | B | F | G | G | E |
|  | 280 | G | B | D | G | G | D |
| 3.06 | 35 | G | G | G | G | G | G |
|  | 70 | G | G | G | G | G | G |
|  | 140 | G | G | G | G | G | G |
| 3.07 | 35 | G | G | G | G | G | G |
|  | 70 | G | G | G | G | G | G |
|  | 140 | G | G | G | G | G | G |
| 3.08 | 35 | G | G | G | G | E | F |
|  | 70 | G | G | G | G | D | D |
|  | 140 | F | C | G | G | D | C |
| 3.09 | 35 | G | B | G | G | D | D |
|  | 70 | G | B | G | G | C | C |
|  | 140 | G | B | G | G | B | B |
| 3.10 | 35 | G | G | G | G | G | D |
|  | 70 | G | G | G | G | G | D |
|  | 140 | G | G | G | G | G | D |
| 3.11 | 35 | G | G | G | G | G | G |
|  | 70 | G | G | G | G | G | G |
|  | 140 | G | G | G | G | G | G |
| 3.12 | 35 | G | B | G | G | G | A |
|  | 70 | G | B | G | G | G | A |
|  | 140 | G | B | G | G | G | A |
| 3.13 | 35 | G | D | n/a | G | G | D |
|  | 70 | G | D | n/a | G | G | D |
|  | 140 | G | C | n/a | G | G | D |
| 3.14 | 35 | G | G | G | G | G | G |
|  | 70 | G | G | G | G | G | F |
|  | 140 | G | G | G | G | G | D |
| 3.15 | 35 | G | C | G | G | G | D |
|  | 70 | G | C | G | G | G | D |
|  | 140 | G | A | G | G | G | D |
| 3.16 | 35 | G | C | G | G | G | D |
|  | 70 | G | C | G | G | G | D |
|  | 140 | E | C | G | G | G | C |

TABLE 16-continued

Post-emergent Test II Herbicidal Activity on Key Grass and Sedge Weeds as well as Grass Crops

| C. No. | Application Rate (g ai/ha) | CYPES | ECHCG | SETFA | ORYSA | TRZAS | ZEAMX |
|---|---|---|---|---|---|---|---|
| 3.17 | 35 | G | E | G | G | G | F |
|  | 70 | G | D | G | G | G | D |
|  | 140 | G | A | F | G | G | C |
| 3.18 | 35 | G | G | G | G | G | G |
|  | 70 | G | G | G | G | G | G |
|  | 140 | G | G | G | G | G | G |
| 3.19 | 35 | G | G | G | G | G | G |
|  | 70 | G | G | G | G | G | G |
|  | 140 | G | G | G | G | G | G |
| 3.20 | 35 | F | G | G | G | G | G |
|  | 70 | F | E | G | G | G | C |
|  | 140 | B | D | D | G | F | B |
| 3.21 | 35 | G | C | G | G | F | F |
|  | 70 | G | B | F | F | F | D |
|  | 140 | G | B | D | F | E | C |
| 3.22 | 35 | G | G | G | G | G | G |
|  | 70 | G | G | G | G | G | G |
|  | 140 | G | G | G | G | G | G |
| 3.23 | 35 | G | G | G | G | G | G |
|  | 70 | G | G | G | G | G | G |
|  | 140 | G | G | G | G | G | G |
| 3.24 | 35 | G | G | G | G | G | G |
|  | 70 | G | G | G | G | G | G |
|  | 140 | G | G | G | G | G | G |
| 3.25 | 140 | G | G | G | G | G | G |
| 3.27 | 35 | G | G | G | G | G | G |
|  | 70 | G | G | G | G | G | G |
|  | 140 | G | G | G | G | G | G |
|  | 280 | G | G | G | G | G | G |
| 4.01 | 35 | G | G | G | G | G | G |
|  | 70 | G | G | G | G | G | G |
|  | 140 | G | G | G | G | G | G |
| 4.03 | 35 | G | D | n/a | G | G | G |
|  | 70 | G | C | n/a | G | G | G |
|  | 140 | G | C | n/a | G | G | G |
| 4.05 | 35 | G | n/a | n/a | G | G | G |
|  | 70 | G | n/a | n/a | G | G | D |
|  | 140 | G | B | A | G | G | D |
| 4.06 | 35 | G | G | G | G | G | G |
|  | 70 | G | E | G | G | G | G |
|  | 140 | G | C | E | G | G | G |
| 4.07 | 140 | G | G | G | G | G | G |
| 4.08 | 140 | G | G | G | G | G | G |
| 4.09 | 35 | G | G | G | G | G | G |
|  | 70 | G | G | G | G | G | G |
|  | 140 | G | G | G | G | G | G |
| 4.10 | 35 | G | G | G | G | G | G |
|  | 70 | G | G | G | G | G | G |
|  | 140 | G | G | G | G | G | G |
| 4.13 | 35 | G | G | G | G | G | G |
|  | 70 | G | G | G | G | G | D |
|  | 140 | G | G | G | G | G | G |
| 5.01 | 35 | n/a | C | G | G | G | G |
|  | 70 | n/a | C | G | G | G | G |
|  | 140 | n/a | B | G | G | G | G |
| 6.01 | 35 | E | G | G | G | G | G |
|  | 70 | E | E | G | G | G | G |
|  | 140 | E | D | G | G | G | G |
| 6.02 | 35 | E | C | G | G | G | G |
|  | 70 | E | C | E | G | G | G |
|  | 140 | E | B | D | G | F | G |
| 7.02 | 35 | G | G | n/a | G | G | G |
|  | 70 | G | G | n/a | G | G | G |
|  | 140 | G | G | n/a | G | G | G |
| 8.01 | 35 | G | G | G | G | G | G |
|  | 70 | G | G | G | G | G | G |
|  | 140 | G | G | G | G | G | G |
| 9.01 | 140 | A | A | G | G | G | D |

ECHCG: barnyardgrass (*Echinochloa crus-galli*)
CYPES: yellow nutsedge (*Cyperus esculentus*)
ORYSA: rice (*Oryza sativa*)
SETFA: giant foxtail (*Setaria faberi*)
TRZAS: wheat, spring (*Triticum aestivum*)
ZEAMX: maize, corn (*Zea mays*)
g ai/ha: grams active ingredient per hectare Example D Evaluation of Postemergent Herbicidal Activity in Wheat and Barley Post-Emergent Test III.

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days (d) in a greenhouse with an approximate 14 hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

A weighed amount, determined by the highest rate to be tested, of each test compound was placed in a 25 mL glass vial and was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Agri-Dex crop oil concentrate, and X-77 surfactant in a 48:39:10:1.5:1.5:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Agri-Dex crop oil concentrate, and X-77 surfactant in a 48:39:10:1.5:1.5:0.02 v/v ratio to obtain 1/2×, 1/4×, 1/8× and 1/16× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by subirrigation to prevent wash-off of the test compounds. After 21 d, the condition of the test plants as compared with that of the untreated plants was determined visually and scored on a scale of 0 to 100 percent where 0 corresponds to no injury and 100 corresponds to complete kill. By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_D$, $GR_{50}$, $GR_{80}$ and $GR_{90}$ values, which are defined as growth reduction factors that correspond to the effective dose of herbicide required to kill or control 20 percent, 50 percent, 80 percent or 90 percent, respectively, of a target plant.

Some of the compounds tested, application rates employed, plant species tested, and results are given in Table 17.

wherein
$R^{1'}$ is hydrogen, $C_1$-$C_8$ alkyl, or $C_7$-$C_{10}$ arylalkyl, or an agriculturally acceptable N-oxide or salt thereof.

2. The compound of claim 1, wherein $R^{1'}$ is hydrogen or $C_1$-$C_4$ alkyl.

3. The compound of claim 2, wherein $R^{1'}$ is hydrogen.

4. The compound of claim 3, wherein the compound is

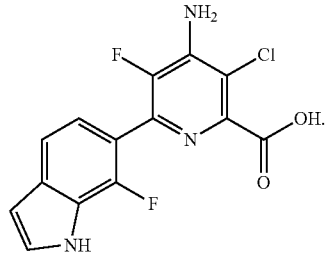

TABLE 17

Activity of Herbicidal Compounds in Wheat and Barley

| Compound No. | Application Rate (g ai/ha) | Visual Growth Reduction (%) 21 Days After Application | | | | | | | | | | |
|---|---|---|---|---|---|---|---|---|---|---|---|---|
| | | HORVS | TRZAS | CIRAR | GALAP | KCHSC | LAMPU | MATCH | PAPRH | SASKR | SINAR | VERPE | VIOTR |
| 1.15 | 17.5 | F | F | F | D | D | A | F | A | C | A | A | E |
| | 35 | E | E | D | B | B | A | E | A | C | A | A | D |
| | 70 | E | D | C | A | B | A | D | A | B | A | A | C |
| | GR20 | 8 | 13 | — | — | — | — | — | — | — | — | — | — |
| | GR50 | — | — | 30 | 9 | 6 | 0.10 | 45 | 0.06 | 7 | 4 | 0.28 | 22 |
| | GR80 | — | — | 70 | 23 | 28 | 1 | >140 | 1 | 30 | 8 | 2 | 63 |
| | GR90 | — | — | 109 | 37 | 67 | 2 | >140 | 2 | 95 | 12 | 6 | 111 |
| 1.16 | 17.5 | G | G | D | F | C | C | B | A | D | B | A | E |
| | 35 | G | G | B | E | B | A | A | A | C | A | A | D |
| | 70 | F | F | A | A | A | A | A | A | B | A | A | C |
| | GR20 | 44 | 41 | — | — | — | — | — | — | — | — | — | — |
| | GR50 | — | — | 9 | 26 | 7 | 3 | 3 | 0.0004 | 10 | 5 | 0.0004 | 19 |
| | GR80 | — | — | 25 | 34 | 20 | 10 | 9 | 0.0004 | 28 | 11 | 0.05 | 56 |
| | GR90 | — | — | 43 | 40 | 39 | 19 | 16 | 0.0004 | 78 | 17 | 1 | 99 |
| 1.23 | 17.5 | G | G | G | A | F | B | G | D | F | C | B | G |
| | 35 | G | G | G | A | E | A | G | A | E | C | B | E |
| | 70 | G | G | G | A | D | A | G | A | C | A | A | D |
| | GR20 | >140 | 66 | — | — | — | — | — | — | — | — | — | — |
| | GR50 | — | — | >140 | 1 | 35 | 3 | 0 | 11 | 29 | 3 | 1 | 44 |
| | GR80 | — | — | >140 | 4 | 110 | 6 | 0 | 17 | 90 | 14 | 8 | 119 |
| | GR90 | — | — | >140 | 7 | >140 | 9 | 0 | 22 | >140 | 32 | 21 | >140 |
| 2.24 | 17.5 | G | G | D | D | D | E | G | D | D | B | F | E |
| | 35 | G | G | C | B | C | D | G | D | B | A | D | D |
| | 70 | G | G | B | B | B | C | G | C | B | A | C | C |
| | GR20 | 66 | 52 | — | — | — | — | — | — | — | — | — | — |
| | GR50 | — | — | 14 | 7 | 4 | 15 | 114 | 24 | 3 | 6 | 30 | 24 |
| | GR80 | — | — | 35 | 23 | 33 | 93 | >140 | 52 | 28 | 13 | 66 | 78 |
| | GR90 | — | — | 57 | 44 | 103 | >140 | >140 | 77 | 95 | 19 | 100 | >140 |

What is claimed is:

1. A compound defined by the formula below

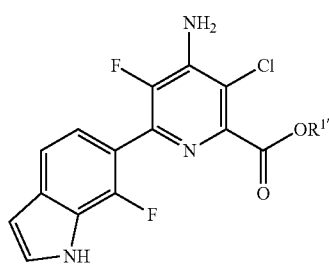

5. The compound of claim 2, wherein $R^{1'}$ is $C_1$-$C_4$ alkyl.

6. The compound of claim 5, wherein $R^{1'}$ is methyl.

7. The compound of claim 6, wherein the compound is

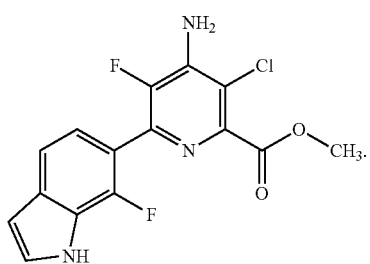 [SMILES: COC(=O)c1nc(-c2ccc3cc[nH]c3c2F)c(F)c(N)c1Cl]

8. The compound of claim 1, wherein $R^{1'}$ is a substituted or unsubstituted $C_8$ arylalkyl group.

9. The compound of claim 8, wherein $R^{1'}$ is a benzyl group.

10. A herbicidal composition comprising a compound of claim 1 and an agriculturally acceptable adjuvant or carrier.

11. The composition of claim 10, further comprising an additional herbicidal compound.

12. The composition of claim 10, further comprising a safener.

13. The composition of claim 10, wherein the compound is

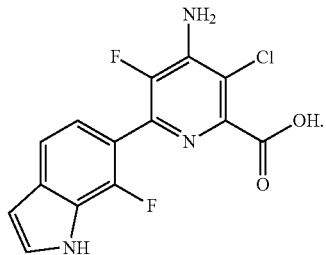 [SMILES: Nc1c(F)c(-c2ccc3cc[nH]c3c2F)nc(C(=O)O)c1Cl]

14. The composition of claim 10, wherein the compound is

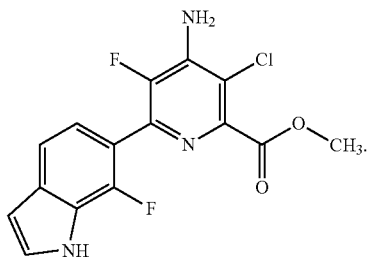 [SMILES: COC(=O)c1nc(-c2ccc3cc[nH]c3c2F)c(F)c(N)c1Cl]

15. A method of controlling undesirable vegetation comprising applying to vegetation or an area adjacent the vegetation or applying to soil or water to control the emergence or growth of vegetation a herbicidally effective amount of a compound of claim 1.

16. A method of controlling undesirable vegetation comprising applying to vegetation or an area adjacent the vegetation or applying to soil or water to control the emergence or growth of vegetation a herbicidally effective amount of a compound of claim 3.

17. A method of controlling undesirable vegetation comprising applying to vegetation or an area adjacent the vegetation or applying to soil or water to control the emergence or growth of vegetation a herbicidally effective amount of a compound of claim 6.

18. A method of controlling undesirable vegetation comprising applying to vegetation or an area adjacent the vegetation or applying to soil or water to control the emergence or growth of vegetation a herbicidally effective amount of a compound of claim 8.

19. A method of controlling undesirable vegetation comprising applying to vegetation or an area adjacent the vegetation or applying to soil or water to control the emergence or growth of vegetation a herbicidally effective amount of a composition of claim 10.

* * * * *